(12) United States Patent
Lee et al.

(10) Patent No.: US 11,037,676 B2
(45) Date of Patent: Jun. 15, 2021

(54) HEALTHCARE FACILITY PATIENT AND VISITOR EXPERIENCE MANAGEMENT AND OPTIMIZATION

(71) Applicants: University Hospitals Cleveland Medical Center, Cleveland, OH (US); LogicJunction, Inc., Beachwood, OH (US)

(72) Inventors: Kipum Michael Lee, Pepper Pike, OH (US); David Joseph Sylvan, Bratenahl, OH (US); Mark Samuel Jowell, Beachwood, OH (US); Michael Joseph Drozda, Aurora, OH (US)

(73) Assignees: UNIVERSITY HOSPITALS CLEVELAND MEDICAL CENTER, Cleveland, OH (US); LOGICJUNCTION, INC., Beachwood, OH (US)

( * ) Notice: Subject to any disclaimer, the term of this patent is extended or adjusted under 35 U.S.C. 154(b) by 302 days.

(21) Appl. No.: 16/156,410

(22) Filed: Oct. 10, 2018

(65) Prior Publication Data
US 2019/0108909 A1 Apr. 11, 2019

Related U.S. Application Data

(60) Provisional application No. 62/571,219, filed on Oct. 11, 2017.

(51) Int. Cl.
| | |
|---|---|
| *G16H 40/20* | (2018.01) |
| *G06Q 10/10* | (2012.01) |
| *G01C 21/36* | (2006.01) |
| *G01C 21/34* | (2006.01) |
| *G01C 21/20* | (2006.01) |
| *G16H 10/60* | (2018.01) |

(52) U.S. Cl.
CPC .......... *G16H 40/20* (2018.01); *G01C 21/206* (2013.01); *G01C 21/3484* (2013.01); *G01C 21/3679* (2013.01); *G01C 21/3697* (2013.01); *G06Q 10/1095* (2013.01); *G16H 10/60* (2018.01)

(58) Field of Classification Search
None
See application file for complete search history.

(56) References Cited

U.S. PATENT DOCUMENTS

| | | | |
|---|---|---|---|
| 9,574,884 B1* | 2/2017 | Nair | G01C 21/206 |
| 2015/0195810 A1* | 7/2015 | Sun | G01C 21/206 |
| | | | 455/456.1 |
| 2018/0358122 A1* | 12/2018 | Raghotham Venkat | |
| | | | G06Q 50/22 |

* cited by examiner

*Primary Examiner* — Kelly D Williams
(74) *Attorney, Agent, or Firm* — Amin, Turocy & Watson, LLP

(57) ABSTRACT

Systems, methods and computer readable media are provided that facilitate managing and optimizing the experience of patients and visitors in association with visiting a medical facility. In an embodiment, as system can include a receiving component that receives arrival data regarding an entity arriving at a healthcare facility. The system can further include a discovery component that determines intent information regarding intent of the entity at the healthcare facility, and analyzes the intent information to determine a destination location for the entity within the healthcare facility, and a wayfinding component that facilitates navigating the entity to the destination location by providing the entity, via a mobile device associated with the entity, with real-time navigation information to the destination location.

25 Claims, 23 Drawing Sheets

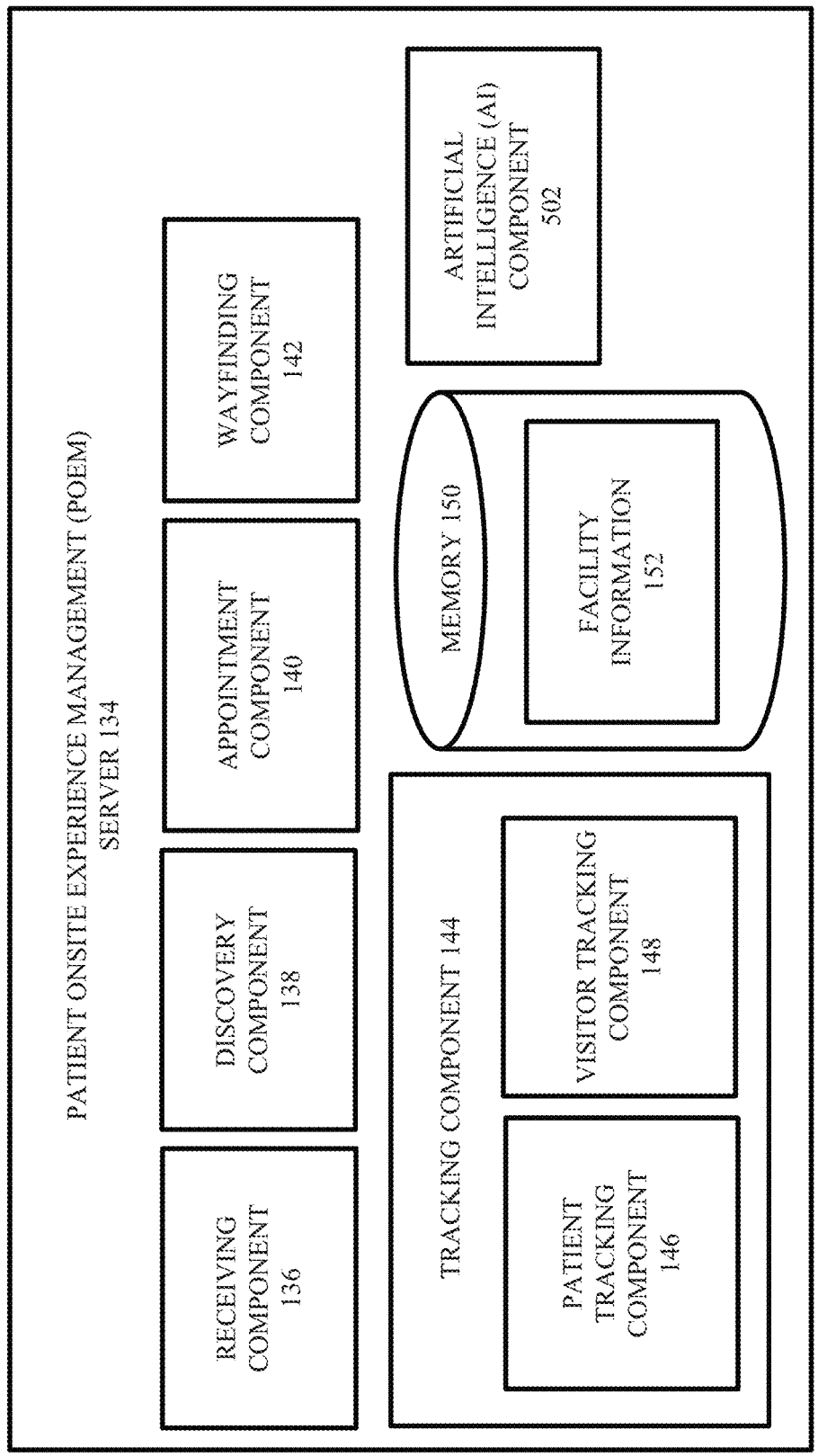

Appointments

Filter: _____

| Doctor | Patient | Date/Time | Patients in Queue | Avg. Appt Duration | State | | Actions |
|---|---|---|---|---|---|---|---|
| Andrew Sloan MD | Mike Orozda | 01/30/2017 at 10:00AM | 4 | 10 | | | |
| Warren Selman MD | Kip Lee | 02/01/2017 at 12:00PM | 1 | 15 | | | |
| Andrew Sloan MD | Malik Khan | 02/02/2017 at 11:00PM | 1 | 30 | | | |
| Julian Kim, MD | Mike Orozda | 02/02/2017 at 12:00PM | | | | | |

FIG. 19

HEALTHCARE FACILITY PATIENT AND VISITOR EXPERIENCE MANAGEMENT AND OPTIMIZATION

CROSS-REFERENCE TO RELATED APPLICATIONS

This application is a U.S. Non-Provisional Patent Application that claims the benefit of priority to U.S. Provisional Patent Application No. 62/571,219 filed Oct. 11, 2017 and titled "HEALTHCARE FACILITY PATIENT AND VISITOR EXPERIENCE MANAGEMENT AND OPTIMIZATION," the entirety of which application is hereby incorporated herein by reference.

TECHNICAL FIELD

This application generally relates to computer processing systems, computer-implemented methods, apparatus and/or computer program products that facilitate managing and optimizing the experience of patients and visitors in association with visiting a healthcare facility.

BACKGROUND

Whether visiting a healthcare facility as a patient or a visitor, most individuals' feelings about the visit are accompanied by some negative emotions, such as fear, worry, pain, dread, and the like. These negative emotions are often exacerbated when the healthcare facility itself is an intimidating environment due to its size, complexity and myriad of different individuals operating under high stress conditions. For example, many modern healthcare facilities encompass massive campuses with many different interconnected and disconnected buildings, floors, rooms, hallways, and the like spanning across large geographic areas, making them very difficult to navigate. The different buildings, floors, rooms and the like are generally dedicated to different medical purposes, such as different medical departments, different types of medical procedures, and the like. When visiting such a healthcare facility, determining exactly where to go, how to get there, what do when you get there and who to talk to can be a rather daunting task.

SUMMARY

The following presents a summary to provide a basic understanding of one or more embodiments of the invention. This summary is not intended to identify key or critical elements, or delineate any scope of the different embodiments or any scope of the claims. Its sole purpose is to present concepts in a simplified form as a prelude to the more detailed description that is presented later. In one or more embodiments described herein, systems, computer-implemented methods, apparatus and/or computer program products that facilitate managing and optimizing the experience of patients and visitors in association with visiting a medical facility.

According to an embodiment of the present invention, a system can comprise a memory that stores computer executable components and a processor that executes the computer executable components stored in the memory. The computer executable components can comprise a receiving component that receives arrival data regarding an entity arriving at a healthcare facility. The system can further include a discovery component that determines intent information regarding intent of the entity at the healthcare facility, and analyzes the intent information to determine a destination location for the entity within the healthcare facility, and a wayfinding component that facilitates navigating the entity to the destination location by providing the entity, via a mobile device associated with the entity, with real-time navigation information to the destination location. In some implementations, the wayfinding component determines position, orientation and elevation information in association providing the entity with the real-time navigation information. In one or more embodiments, the wayfinding component determines the elevation information based on electromagnetic information associated with a ground upon which one or more buildings of the healthcare facility are established. The wayfinding component can further determine a route to the destination location based on the current context of the entity and one or more personalized factors associated with the entity.

In some embodiments, the computer executable components further comprise an assistance component that determines whether a mental of physical condition of the entity indicates a need for physical assistance in association with the navigating and schedules appropriate medical personal or equipment to a current location of the entity accordingly. The computer executable components can also comprise an appointment component that interfaces with an appointment scheduling system associated with the healthcare facility and determines appointment information regarding one or more medical appointments scheduled for the entity at the healthcare facility based on the information identifying the entity, and wherein the discovery component determines the purpose information based on the appointment information. For example, in some implementations the entity comprises a patient, wherein the purpose of the entity at the healthcare facility comprises attending a medical appointment, and wherein the destination location comprises an appointment location at the healthcare facility where the medical appointment is scheduled. With these implementations, the computer executable components can further comprises a waiting time management component that determines an estimated time at which the medical appointment will commence based on a current schedule of a clinician with whom the appointment is scheduled, and wherein the wayfinding component determines a route for the entity from a current location of the entity to the destination location based on the estimated time at which the medical appointment will commence, one or more preferences of the entity, and one or more points of interest within the healthcare facility.

In some embodiments, the waiting time management component can determine and provide the patient, via the mobile device, with real-time updates regarding an estimated duration of a waiting period before the medical appointment will begin. The waiting time management component further provides the patient, via the mobile device, with relevant informative information associated with the medical appointment for viewing during the waiting period. For example, the waiting time management component can determine the relevant informative information based on the estimated duration of the waiting period. In another aspect, the waiting time management component can determines the relevant informative information based on one or more of: a purpose of the appointment, a preference of the patient, or a current mental state of the patient. Further in some implementations, the waiting time management component can suggests via the mobile device, one or more points of interest within the healthcare facility for visiting by the patient during the waiting period based in part on the estimated duration of the waiting period.

The computer executable components can further comprise an appointment preparation component that facilitates generating, prior to initiation of the medical appointment, one or more questions the entity has regarding the medical appointment for providing to a clinician involved with performing the medical appointment. In one implementation, the computer executable components further comprise a check-in component that facilities checking the patient into the medical appointment via the mobile device in response to a determination that the patient has arrived at the appointment location.

In some embodiments, elements described in connection with the disclosed systems can be embodied in different forms such as a computer-implemented method, a computer program product, or another form.

BRIEF DESCRIPTION OF THE DRAWINGS

Numerous aspects, embodiments, objects and advantages of the present invention will be apparent upon consideration of the following detailed description, taken in conjunction with the accompanying drawings, in which like reference characters refer to like parts throughout, and in which:

FIG. 5 illustrates an additional artificial intelligence component that can be employed by the POEM server to facilitate managing and optimizing the user experience at the medical facility in accordance with various aspects and embodiments described herein;

FIGS. 10 and 11 present example GUIs of the POEM application associated with the appointment management functionality in accordance with aspects and embodiments disclosed herein;

FIGS. 14A-14D present example GUIs that can be generated and presented by the POEM application to facilitate preparing a user for an upcoming appointment in accordance with aspects and embodiments disclosed herein;

FIG. 19 presents an example GUI associated with an appointment scheduling system in accordance with aspects and embodiments disclosed herein;

DETAILED DESCRIPTION

Figure 1:
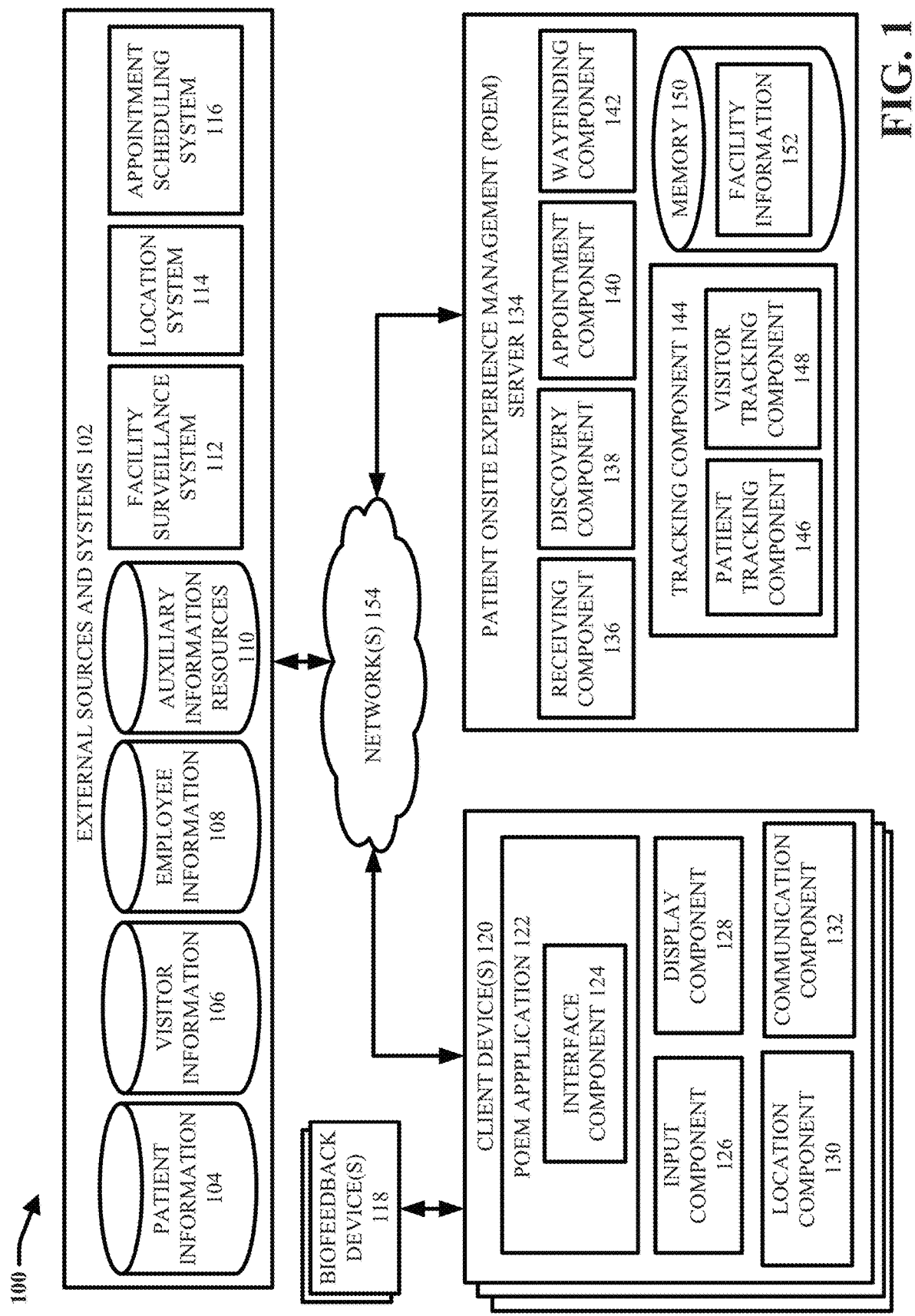
FIG. 1 illustrates an example system that facilitates managing and optimizing the experience of patients and visitors in association with visiting a healthcare facility in accordance with various aspects and embodiments described herein.

The following detailed description is merely illustrative and is not intended to limit embodiments and/or application or uses of embodiments. Furthermore, there is no intention to be bound by any expressed or implied information presented in the preceding Background section, Summary section, or in the Detailed Description section.

The subject disclosure is directed to computer processing systems, computer-implemented methods, apparatus and/or computer program products that facilitate enhancing the overall experience of patients and visitors in association with visiting a healthcare facility. In one or more embodiments, the disclosed computer implemented techniques can provide an intra-office patient navigation and information system that facilitates managing and optimizing hospital visits and stays. In some implementations, via a computing device associated with the patient or visitor (e.g., a personal mobile device of the patient or visitor such as smartphone or wearable head mounted device, a mobile device or the healthcare facility provided to the patient or visitor upon entry, and the like), the disclosed techniques can provide the patient or visitor with a greeting when the patient or visitor enters a defined geographical area (e.g., hospital campus) or even at the home of the patient or visitor on the day of or prior to a scheduled hospital visit (e.g., to attend a medical appointment, to visit an admitted patient, or the like). The system can further help navigate the patient or visitor to and through the healthcare facility using the mobile device by providing the patient or visitor with real-time navigation information at the mobile device. In one or more embodiments, the disclosed techniques can employ a unique location finding system that can identify not only a two-dimensional coordinate position of a user (e.g., the x and y location), patient but also the vertical elevation of the user relative to the ground (e.g., z-axis information, the floor level of a building with two or more floors, etc.). In some implementations, in addition to navigation information, the disclosed computer implemented techniques can provide the patient or visitor with information identifying and describing points of interests in the healthcare facility throughout the visit.

In one or more embodiments, the specific navigation route and point of interest information presented to a user can be personalized based on the context of the user. In this regard, the context of the user can relate to a reason for the visit, a destination location of the user within the facility, where and when the user enters the facility, a current time and a time factor associated with the visit (e.g., a scheduled appointment time, the clinician's actual workflow schedule, authorized visiting hours, progress of a procedure, etc.), and the like. For example, the state of the physician (e.g., ahead of schedule, backed up) with whom a patient has a scheduled medical appointment with can be factored by the system which can adjust provisioning of services. For instance, if the doctor is backed up by 30 minutes, the system can suggest going to a coffee shop in the building. The specific navigation route and point of interest information provided to the user can also be tailored to the user based on a current mental state of the user, a current physical state of the user (e.g., including any physical limitations of the user), preferences of the user, whether the user is alone or accompanied by one or more other individuals, and the like. For example, the navigation route can be tailored to account for the pace of the user, whether the user is able to climb stairs, whether the user prefers seeing certain points of interest along the route, etc. In some implementations, the disclosed techniques can also employ knowledge of the patient's medical history and current mental and physical state in connection with provisioning of resources. For example, if the patient needs a wheelchair or nurse assistances, a wheelchair and/or a nurse can be waiting for the patient upon arrival at the car port. In another embodiment, the system can communicate with a self-driving vehicle to provide instructions for patient drop-off, parking and pick-up.

The system can further facilitate managing and preparing a patient for medical appointments scheduled at the healthcare facility. For instance, in some embodiments, the disclosed techniques can interface with a scheduling system of the healthcare facility to facilitate checking a patient into and out of an appointment. For example, in one implementation, the system can provide a patient (or entity assisting the patient), with a mechanism to check-in and check-out of the appointment using an application executed on or accessed by a client device associated with the patient. In another example, the disclosed techniques can automatically check a patient into and out of an appointment based on monitoring the physical location of the patient (e.g., arrival at the doctor's office can result in automatic check in while exiting the office and remaining outside the office for a defined time period can result in automatic check out). The system can also provide a patient, via a client device associated with the patient, with questionnaires at appropriate times to facilitate check-in and check-out and to increase the overall efficiency, quality and productivity of the appointment. For example, the disclosed techniques can involve providing the patient, via the client device, with medical forms that the patient is required to fill out prior to the appointment. The questionnaires can also include questions related to the visit that can facilitate preparing the patient for the appointment. For example, the questionnaires can provide the patient with questions and corresponding answers that are likely to be asked by the patient during the appointment, thereby minimizing the amount of time that the clinician would have otherwise spent answering patient questions during the appointment. The questions and answers can be based on historical analysis of past patient appointments and frequently asked questions and answers. The questions and answers can also be tailored to respective patients (using machine learning) based on the personalized factors associated with the context of the patients, the patients' condition, the current mental state of the patients, preferences of the patients, an educational level of the patients, and the like. In another implementation, the questionnaires can facilitate preparing the patient with pertinent questions to ask the clinician during the appointment. For example, the pertinent questions can include those for which the patient does not understand a machine generated answer or would like additional explanation for by the clinician during the appointment. In another example, the pertinent questions can include those for which a machine generated answer is not available. The system can also provide a patient with other forms of informative or entertaining content that pertains to their upcoming medical appointment that the patient can view prior to the appointment (e.g., in the waiting room). For example, oftentimes, doctors provide a same speech regarding a procedure to multiple patients. The system can present prepared videos regarding such information so that the physician does not have to, thus improving overall all patient throughput. The system can also provide entertainment or informational content to the patients and visitors at appropriated times throughout their visit (e.g., while in the waiting room) as a function of user preference and state.

The terms healthcare facility or medical facility as used herein can refer to any physical location (e.g., building, building complex, campus, etc.) where healthcare is provided. Healthcare facilities can range from small clinics and doctor's offices to urgent care centers and large hospitals with elaborate emergency rooms and trauma centers. Although many embodiments of the subject disclosure are described in association with managing and optimizing the user experience at large and complex healthcare facilities, it should be appreciated that the disclosed techniques can be applied to any type of healthcare environment, including but not limited to: a hospital, an ambulatory surgical center, a doctor's office, an urgent care clinic, and a nursing home. Further, various embodiments of the disclosed techniques refer to assisting patients and visitors in association with visiting a healthcare facility. In this regard, a patient generally refers to an individual that visits the healthcare facility to receive medical treatment while a visitor refers to an individual that does not work at the healthcare facility and visits the healthcare facility for any other purpose aside from receiving medical treatment. For example, a visitor can include an individual that accompanies a patient to the healthcare facility, an individual the goes to the healthcare facility to see an admitted patient, an individual that visits the healthcare facility for a job interview, an individual that visits the healthcare facility to see or perform an exhibition held at the healthcare facility, and the like. However, it should be appreciated that various aspects of the disclosed techniques can be applied to other types of users and application of the disclosed techniques are not limited to healthcare facility patients and visitors. For example, the disclosed techniques can be employed to facilitate optimizing the experience of employees of the healthcare facility, as well as non-human entities (e.g., computing devices, machines, self-driving vehicles, self-driving wheelchairs, robots, and other intelligent machines).

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Aspects of systems, apparatuses or processes explained in this disclosure can constitute machine-executable components embodied within machine(s), e.g., embodied in one or more computer readable mediums (or media) associated with one or more machines. Such components, when executed by the one or more machines, e.g., computer(s), computing device(s), virtual machine(s), etc. can cause the machine(s) to perform the operations described.

Referring now to the drawings, FIG. 1 presents an example system that facilitates facilitate managing and optimizing the experience of patients and visitors in association with visiting a healthcare facility in accordance with various aspects and embodiments described herein. System 100 can include various external sources and systems 102, one or more client devices 120, one or more biofeedback device 118, and a patient onsite experience management (POEM) server 134. The server is referred to as a patient onsite experience management (POEM) server to indicate the POEM server 134 provides various features and functionalities associated with managing and enhancing the experience of a patient when onsite or otherwise physically located at the site of a healthcare facility. However, the name of the server is not intended to limit its functionality. For example, as described herein, the POEM server 134 can also provide various features and functionalities to other entities in addition to patients (e.g., visitors, employees, intelligent machines, etc.). Further, the features and functionalities of the POEM server 134 can also facilitate improving an entities' upcoming experience at the healthcare facility before the entity arrives at the healthcare facility (e.g., at home the day before a scheduled visit, on the route to the healthcare facility, etc.).

In accordance with various embodiments, the POEM server 134 can be configured to provide information and services that facilitate managing and optimizing the experience of users (e.g., patients and visitors) at a healthcare facility. The information and services provided by the POEM server 134 can be facilitated by various computer executable components provided at the POEM server 134, including but not limited to, the receiving component 136, the discovery component 138, the appointment component 140, the wayfinding component 142, the tracking component 144 and the facility information 152 stored in memory 150 of the POEM server 134. In some implementations, the information and services provided by the POEM server 134 can also include information and services provided by or facilitated by one or more external sources and systems 102 that are accessible to the POEM server 134 via one or more networks 154. With these embodiments, a user (e.g., a patient, a visitor, a healthcare facility employee, an intelligent machine, etc.) can access and receive the information and services provided by the POEM server 134 using a client device 120. For example, with respect to patients and visitors, in some implementations, the client devices 120 can include mobile devices that the patients or visitors can wear or carry (e.g., a smartphone, a tablet personal computer (PC), a heads-up display (HUD) device, a head mounted device, a wearable augmented reality device such as goggles or glasses, a wearable virtual reality device, etc.). In accordance with these embodiments, the POEM server 134 and the respective client devices 120 can be configured to operate in a server/client relationship, wherein the POEM server 134 provides the respective client devices 120 access to the information and services provided by the POEM server 134 via a network accessible platform (e.g., accessible via one or more networks 154) that facilitates communication can coordinated processing of information shared between devices (e.g., the client devices, 120 the POEM server 134, the biofeedback device 118, and the one or more external sources and systems 102). For example, the network accessible platform can include a mobile application based platform (e.g., a thin client application, a thick client application, a web-application, a hybrid application), a website platform, or another suitable network based platform.

For example, in the embodiment shown, the client devices 120 can respectively include a POEM application 122 that can be configured to facilitate accessing and employing the information and services provided by the POEM server 134. According to this embodiment, the POEM application 122 can include interface component 124 to interface with the POEM server 134 to facilitate accessing and employing the information and services provided by the POEM server 134. In some implementations, the interface component 124 can generate various graphical user interfaces (GUI)s that facilitate receiving user input in association with accessing and employing the information and services provided by the POEM server 134. Some examples of such GUIs are presented infra with reference to FIGS. 6-19. In another embodiment, the POEM server 134 can provide a website based platform that can be accessed by the respective client devices using a suitable browser. In either of these embodiments, the information and services provided by the POEM server 134 can be accessed and received by a client device 120 when the POEM application 122 and/or the client device 120 is connected to the POEM server 134, a scenario often referred to as being "connected" or "online." However, in some implementations, at least some of the information and services provided by the POEM server 134 discussed herein can be stored at and executed by the client device 120 via the POEM application 122 when the client device is disconnected form the POEM server 134, a scenario often referred to as being "disconnected" or "offline."

It should be appreciated however that system 100 is not limited to this architectural configuration. For example, in some embodiments, one or more components of the POEM server 134 described herein can be provided at the client device 120. In other embodiments, one or more of the external sources and systems 102 can be stored at or executed by the POEM server 134. In another embodiment, one or more of the external sources and systems 102 can be stored at or executed by a client device 120. In some embodiments, the POEM server 134 and/or one or more components of the POEM server 134 and the external information sources and systems 102 can be included in a cloud-computing network. "Cloud computing" is a kind of network-based computing that provides shared processing resources and data to computers and other devices on-demand via a network (e.g., one or more networks 154). It is a model for enabling ubiquitous, on-demand access to a shared pool of configurable computing resources (e.g., networks, servers, storage, applications and services), which can be rapidly provisioned and released with minimal management effort. Cloud computing and storage solutions provide users and enterprises with various capabilities to store and process their data in third-party data centers.

Depending on the system architecture employed (which is not limited that shown in FIG. 1 as described above), the various devices, systems/sources, and components of system 100 can be connected either directly or via one or more networks 154. Such network(s) can include wired and wireless networks, including but not limited to, a wide area network (WAN), (e.g., the Internet, a facility Intranet, and the like), a local area network (LAN), and/or a personal area network (PAN). For example, the one or more networks 154 can include but are not limited to: cellular networks, femto networks, picocell networks, microcell networks, Internet protocol (IP) networks Wi-Fi service networks, broadband service network, enterprise networks, cloud based networks, and the like. In an aspect, one or more devices or components of system 100 can be configured to interact via disparate networks. For example, a client device 120 can communicate with the POEM server 134, a biofeedback device 118, one or more external sources and systems 102, (and vice versa), using virtually any desired wired and wireless technology. These wired and wireless technologies can include but are not limited to: Universal Mobile Telecommunications System (UMTS) technologies, LTE technologies, advanced LTE technologies (including voice over LTE or VoLTE), narrowband IoT (NB-IoT), Code Division Multiple Access (CDMA) technologies, Time Division Multiple Access (TDMA) technologies, Orthogonal Frequency Division Multiplexing (OFDN) technologies, Filter Bank Multicarrier (FBMC) technologies, Wireless Fidelity (Wi-Fi) technologies, Worldwide Interoperability for Microwave Access (WiMAX) technologies, General Packet Radio Service (GPRS) technologies, Enhanced GPRS, technologies, Third Generation Partnership Project (3GPP) technologies, Fourth Generation Partnership Project (4GPP) technologies, Fifth Generation Partnership Project (5GPP) technologies, Ultra Mobile Broadband (UMB) technologies, High Speed Packet Access (HSPA) technologies, Evolved High Speed Packet Access (HSPA+), High-Speed Downlink Packet Access (HSDPA) technologies, High-Speed Uplink Packet Access (HSUPA) technologies, ZIGBEE® technologies, or another IEEE 802.XX technology, BLUETOOTH® technologies, BLUETOOTH® low energy (BLE) technologies, near field communication (NFC), RF4CE, WirelessHART, 6LoWPAN, Z-Wave, ANT, and the like.

The one or more client device 120 can include any suitable computing device configured to facilitate accessing and employing the information and services provided by the POEM server 134. For example, the one or more client device 120 can include a desktop computer, a laptop computer, a television, an Internet enabled television, a mobile phone, a smartphone, a tablet personal computer (PC), a personal digital assistant PDA, a wearable device (e.g., a HUD device, an AR device, a VR device, smart classes, googles, an earpiece, etc.), a vehicle (including a self-driving vehicle), and the like.

The respective client devices 120 can include suitable hardware and software that facilitates receiving and interpreting user input, displaying or rendering information, and communicating with other devices (e.g., the POEM server 134, one or more biofeedback devices 118 and the like). For example, the respective client devices 120 can include an input component 126 to facilitate receiving and interpreting user input. The input component 126 can include various suitable input hardware, including but not limited to: a touchscreen, hard or soft buttons, a keyboard, a keypad, a mouse, a joystick, voice input, motion/gesture input, image input and the like. The respective client devices 120 can include a display component 128 that can be configured to display various types of data including text, media, and rich media and the like (e.g., via a GUI rendered on a display screen or another suitable medium). One or more of the client devices 120 can also include a location component 130 to facilitate determining a location of the client device 120. In some implementations, location information determined by the location component 130 can be provided to the POEM server 134 to facilitate navigating a user of the client device 120, (or the client device itself in implementations in which the client device comprises a self-driving vehicle or robot), to and/or throughout the healthcare facility. The respective client devices 120 can also include a communication component 132 configured with suitable communication hardware and software (e.g., a central processing unit (CPU), a transmitter, a receiver, a transceiver, a decoder/encoder, etc.) to facilitate wired or wireless communication between the client device 120 and other devices (e.g., the POEM server 134, a biofeedback device 118, other external devices and the like).

The POEM server 134 and the one or more client devices 120 can respectively comprise at least one processor (not shown) and at least one memory (e.g., memory 150 and not shown in the client device 120) that stores executable instructions that, when executed by the processor, facilitate performance of operations. For example, with respect to the POEM server, these components can include but are not limited to: the receiving component 136, the discovery component 138, the appointment component 140, the way-finding component 142, and the tracking component 144. In another example, with respect to the one or more client devices 120, these components can include the POEM application 122. In some embodiments, at least some (software) features and functionalities of the input component 126, the display component 128, the location component 130 and the communication component 132 can also be stored in memory of the client device 120 and executed by a processor of the client device. Examples of said processors and memories, as well as other suitable computer or computing-based elements, can be found with reference to FIG. 22 and can be used in connection with implementing one or more of the systems or components shown and described in connection with FIG. 1 or other figures disclosed herein.

Various embodiments of the disclosed techniques for managing and optimizing the experience of a user in association with visiting a healthcare facility are described wherein the POEM server 134 provides the user (e.g., via a client device 120 associated the user) with access to information and services that facilitate managing and optimizing the user experience. In some implementations, the information and services provided by the POEM server 134 can also include information and services provided by or facilitated by one or more external sources and systems 102 that are accessible to the POEM server 134 via one or more networks 154. For example, these external sources and systems 102 can include data sources including but not limited to: patient information 104, visitor information 106, employee information 108, and auxiliary information resources 110.

The patient information 104 can include information identifying current and past patients of the healthcare facility and associating various types of known information about the respective patients that can be used by the POEM server 134 to provide personalized information and services to the respective patients. For example, the patient information 104 can include information identifying a patient (e.g., the patient's name) as well as information that can be used to identify the patient online (e.g., in association with access of or connection to the network accessible platform of the POEM server 134 using a client device 120) and/or in person (e.g., in association with arrival at a physical location of the healthcare facility). For instance, information that can be used to identify a patient in association with usage of a network accessible platform (e.g., a mobile application, a website, etc.) of the POEM server 134 can include but is not limited to: a device identifier (e.g., phone number, serial number, IMEI, etc.) associated with the client device 120, a username, a password, biometric information, and the like. Information that can be used to identify a patient in person can include information identifying a device worn by or carried by the patient (e.g., a client device 120, a radio frequency identifier (RFID) device, an electronic key card, etc.), biometric information for the patient that can be used in association with allowing a user access to the healthcare facility (e.g., to open a door, to pass through a secure barrier, etc.), facial recognition information, and the like. In addition to information identifying a patient and information that can be used by the POEM server 134 to determine the identity of a patient online and/or in-person, the patient information 104 can also include additional rich information about the patient. This additional information can include but is not limited to: demographic information (e.g., age, gender, cultural background, primary language spoken, etc.), historical health information (e.g., the patient's electronic medical record (EMR), information regarding the patient's preferences, and the like. In some implementations, with respect to current patients, the patient information 104 can include real-time or regularly updated information regarding the location of the patient, the status of the patient (e.g., in surgery, in recovery, waiting to be seen by Dr. Johnson in room 203, etc.).

The visitor information 106 can also include information identifying current and past visitors of the healthcare facility and associating various types of known information about the respective visitor that can be used by the POEM server 134 to provide personalized information and services to the respective visitors. In this regard, the visitor information 106 can include same or similar types of information described above with respect to the patient information 104 that can identify or be used to identify the respective visitors online or in person. The visitor information can also additional rich information about the respective visitors that can be used by the POEM server 134 to tailor or personalize information and services provided to the visitor. For example, this additional visitor information can include but is not limited to: information regarding any known relationships of a visitor with current and past patients (e.g., visitor Jane Doe is the mother of patient John Doe), demographic information, preference information, historical information regarding past visits to the healthcare facility, and the like.

The employee information 108 can also include information identifying current employees (e.g., clinicians, administrative employees, custodial employees, etc.) of the healthcare facility and associating various types of known information about the respective employees that can be used by the POEM server 134 to provide personalized information and services to the respective employees, patients and visitors. For example, the employee information 108 can be used by the POEM server 134 to distinguish between users that are employees, visitors and patients. The employee information can also be employed to facilitate provisioning of services to patients and visitors by the respective employees (e.g., directing a particular nurse located in the vicinity of a patient to assist the patient, and the like). In this regard, the employee information 108 can include same or similar types of information described with respect to the patient information 104 that can identify the respective employees and/or that can be used to identify the respective employees online or in person. The employee information 108 can also include additional rich information about the respective employees. For example, this additional employee information can include but is not limited to: information regarding their relationships with current and past patients (e.g., patient John Doe is being treated by Dr. Johnson), demographic information, preference information, information identifying and describing their role at the healthcare facility, information identifying or describing their qualifications, and the like.

The auxiliary information resources 110 can include various types of informative and/or entertaining literature and media (e.g., audio, video, still images, etc.) that can be provided to patients and visitors to enhance their experience at the healthcare facility. For example, in one or more embodiments, the POEM server 134 can provide relevant auxiliary information to patients and visitors (e.g., that is relevant to the purpose of their visitors) in association with their visit at appropriate times to improve their experience. For example, while a visitor is waiting to pick-up a patient from surgery and take the patient home, the visitor can be provided with auxiliary information (e.g., videos, articles, etc.), that inform the visitor how to care for the patient post surgery at home). In another example, while a patient is waiting for an upcoming medical appointment to begin, the patient can be provided with information describing what to expect during the appointment. In this regard, the auxiliary information resources 110 can include informative medical information regarding different medical conditions and diagnosis, medical procedures, types of medical appointments and the like. In some implementations, the auxiliary information resources 110 can also include question and answer information regarding known medical questions and corresponding answers, questionnaire information, survey information, patient intake forms, and the like. The auxiliary information resources 110 can also include entertaining media (e.g., movies, video clips, television shows, news articles, etc.), games and the like that can be accessed by and/or provided to patients and visitors in association with their visit to the healthcare facility.

In addition to the various data sources described above, the external information sources and systems 102 can also include (but are not limited to) a facility surveillance system 112, a location system 114 and an appointment scheduling system 116. The facility surveillance system 112 can include a surveillance or security system of the healthcare facility that can provide real-time information regarding user activity at the healthcare facility. For example, the facility surveillance system 112 can include a sensor network comprising sensory devices distributed at various strategic locations within and around the healthcare facility that can monitor and detect movement of people and devices about the healthcare facility, such as entry and exit of people and devices at defined physical locations (e.g., property lines, building, rooms, hallways, etc.). For example, the sensor network can include cameras, motion sensor devices, acoustic sensors, and the like. In some implementations, the facility surveillance system 112 can also determine the identity of entities in association with their presence and/or movement at various locations of a healthcare facility (e.g., using patient information 104, visitor information 106 and employee information 108). For example, using facial recognition techniques, the facility surveillance system 112 can identify patients, visitors and employees captured in image data via one or more cameras of the facility surveillance system 112. Accordingly, in some embodiments, the facility surveillance system 112 can provide the POEM server 134 with information regarding the identity of an entity at the healthcare facility, the location of the entity relative to the healthcare facility, and movement of the entity at the healthcare facility.

The location system 114 can include an internal location system associated with the healthcare facility that can be used to determine precise locations of entities relative to the healthcare facility. The location system 114 can employ one or more location determination techniques to identify locations of entities (e.g., people, objects and devices), relative to the healthcare facility, including precise locations of the entities in both indoor and outdoor environments of the healthcare facility. In some implementations, the location system 114 can determine the locations of entities based on determination of the location of a client device 120 (or anther detectable device such as an RFID device or another type of signal transmitting device) that is attached to or carried by the entity. With these implementations, the location system 114 can communicate with the client device 120 (or the other type of device) to receive wireless signals (e.g., radio frequency (RF) signals, optical signals, acoustic signals, etc.) from the client device 120 that can facilitate determining the location of the client device 120 using one or more ranging and/or angulating methods (e.g., angle of arrival, line-of-sight, time of arrival, multilateration, time-of-flight, two-way ranging and the like). Alternatively, the location system 114 can determine the actual location of non-transmitting objects (e.g., the patients and the visitors themselves), using various optical ranging and positioning capture devices (e.g., a light detection and ranging (LIDAR) device) and one or more ranging and/or angulating methods.

In one or more embodiments, the location system 114 can be particularly configured to determine not only the x, and y coordinate location of a user or a device within the healthcare facility, but also the vertical elevation of the user relative to the ground. In this regard, the location system 114 can determine what floor or level of a building a user or device is located, as well as elevations between floors associated with movement on an elevator between floors or movement of a user or device up and down stairs or the like. In some embodiments, the location system 114 can determine the elevation information for a user or device based on electromagnetic information associated with a ground upon which one or more buildings of the healthcare facility are established.

In some embodiments, in order to determine the precise location of a user or device relative to a healthcare facility, the location system 114 can correlate position measurements (e.g., x, y and z measurements) determined for a user or device with facility information that provides precise information identifying the relative locations, sizes and shapes of physical structures of the healthcare facility (e.g., buildings, walkways, points of interest, halls, rooms, walls, floors, elevators, stairs, escalators, fixtures, etc.) in three-dimensional space. For example, this facility information can be included in memory 150 (e.g., as facility information 152) or otherwise accessible to the location system 114. In some implementations, the facility information can include a three-dimensional model of the healthcare facility. The facility information can also include a two-dimensional map of the healthcare facility, including a two-dimensional map of respective levels or floors of the healthcare facility at different elevations.

In other embodiments, in addition or alternative to location information regarding a current location of a patient, visitor or other entity relative to the healthcare facility determined and/or provided to the POEM server 134 by the facility surveillance system 112 and/or the location system 114, the client device 120 can provide the POEM server 134 with information regarding the location of the client device 120 as determined via the location component 130. With these embodiments, the client device 120 can be held, worn, carried or otherwise physically attached to an entity (e.g., a patient, visitor, employee, device, etc.). For example, the location component 130 of the client device 120 can determine location information identifying a current location of the client device 120 using one or more of the various location determination techniques described herein, a global positioning system (GPS), and other potential location determination techniques. The POEM application 122 can further provide the POEM server 134 with the location information (e.g., as authorized by the user of the client device 120) when the POEM application is connected to the POEM server 134.

Appointment scheduling system 116 can include one or more medical appointment scheduling systems employed by the healthcare facility to schedule and manage medical appointments. In some implementations, the appointment scheduling system 116 can include a universal system that manages medical appointment scheduling for all medical departments at the healthcare facility. In other implementations, the appointment scheduling system 116 can include two or more separate scheduling systems employed by different departments. The appointment scheduling system can maintain information identifying scheduled appointments, including the patient scheduled, the time and date of the appointment, the medical clinician or department with which the appointment is scheduled, the location of the appointment, the type of the appointment, information regarding the purpose of the appointment, information regarding medical forms and things recommended or required for the patient to bring to the appointment or otherwise do to prepare for the appointment, and the like. In some embodiments, the appointment scheduling system 116 can also track and update information regarding the progress of medical appointments, including information identifying whether a patient is checked into the medical appointment, whether the medical appointment is currently in progress, a current timeline of the medical appointment (e.g., tracking real-time duration of the medical appointment), whether the patient has check out of the medical appointment, and the like.

In some embodiments, the POEM server 134 can tailor information and services provided to a user based on the current mental and physical state of the user. In some implementations, the POEM server 134 can receive real-time information regarding the current mental and/or physical state of the user captured from one or more biofeedback devices 118 associated with the user. For example, the biofeedback devices 118 can include various types of devices that are worn by or implanted within a person and configured to capture various biofeedback measurements that can be sent to and POEM server 134 (e.g., in real-time or substantially real-time as they are captured). Such biofeedback measurements can be correlated to one or more health states of a patient. For example, the biometric measurements can include but is not limited to, information regarding the user's heart rate, respiratory rate, muscle tension, and hormone levels (e.g., cortisol, oxytocin, acetylcholine, dopamine, serotonin, gaba, glutamine, blood pressure level, glucose level endorphin, epinephrine, norepinephrine, and glutamate). In the embodiment shown, a biofeedback device 118 can be communicatively coupled to the client device 120 (e.g., via a short range communication technology) and the client device 120 can receive the biofeedback information from biofeedback device 118 and provide it to the POEM server 134 (e.g., via the POEM application 122). In other embodiments, the biofeedback device can be included with the client device or the biofeedback device can provide biofeedback measurements directly to the POEM server 134. The POEM server 134 can also determine information regarding a user's mental state based on feedback information including one or more facial expressions of the user, speech of the user, and/or motion of the user.

The POEM server 134 can include receiving component 136 to receive the various types of information discussed herein that can be provided by or determined by the one or more external sources and systems 102, the one or more client devices 120 and the biofeedback devices 118. In some embodiments, some of this information can be automatically provided to or pushed to the receiving component 136 by the POEM application 122 (e.g., location information determined by the location component 130, biofeedback information), and the external sources and systems 102. In other embodiments, the receiving component 136 can access, retrieve or request such information as needed.

Various embodiments of the subject disclosure are directed to enhancing the user experience associated with visiting a healthcare facility from the time the user arrives to the time the user leaves. In some implementations discussed infra, this can involve helping the user find the healthcare facility, helping the user determine where to park if driving, directing a user or a self-driving vehicle where to drop-off and pick-up a patient or visitor and the like. Further in one or more additional implementations, system 100 can provide for preparing a patient or visitor with information regarding an upcoming visit to the healthcare facility prior to day or time of the visit.

In many of these embodiments, the discovery component 138 can be configured to determine information regarding the intent or purpose of an entity at a healthcare facility in association with arrival of the entity at the healthcare facility. For example, the discovery component 138 can determine whether an entity arriving at a healthcare facility is a patient that is attending a medical appointment at the healthcare facility, a friend or family member of the patient that is assisting or supporting the patient, a visitor intending to visit an admitted patient (in implementations in which the healthcare facility is a hospital), an employee at the healthcare facility arriving for work, and the like. In this regard, the discovery component 138 can be configured to determine information including but not limited to, when an entity arrives at the healthcare facility, where the entity has arrived, who the entity is (e.g., by name, identification number or the like), and the purpose of their visit to the healthcare facility. With respect to the purpose of an entities' visit for example, the discovery component 138 can determine information regarding one or more destination locations within the healthcare facility that the entity should visit and when (e.g., the particular room where their medical appointment is scheduled, the laboratory where the patient is to have bloodwork done post appointment, the room where a visitor should go to visit an admitted patient, the gift shop, etc.). In some implementations, the discovery component 138 can also determine one or more actions the entity should perform in association with navigating to or arriving at the one or more destination locations (e.g., where and how to check into an appointment, whether to fill out any intake forms, etc.). The discovery component 138 can employ various techniques to determine information regarding when an entity arrives at the healthcare facility, where they have arrived, who the entity is, and the purpose of their visit to the healthcare facility based on information accessed and/or received by the POEM server 134 via the receiving component 136. These techniques and additional features and functionalities of the discovery component 138 are discussed infra with reference to FIG. 2.

The appointment component 140 can provide various services associated with attending a medical appointment at the healthcare facility in implementations in which the purpose or intent of the entity arriving at the healthcare facility involves attending one or more medical appointments. In this regard, the entity can include a patient or an individual (e.g., a friend, a family member, a caregiver) that is assisting or supporting the patient in association with the medical appointment. For example, in one or more embodiments, the appointment component 140 can determine, based on information identifying the entity arriving at the healthcare facility and appointment scheduling information provided by the appointment scheduling system 116, if the entity or a patient associated with the entity has a scheduled medical appointment at the healthcare facility on arrival date. If the entity or a patient associated with the entity has a scheduled appointment, the appointment component 140 can further determine (e.g., based on scheduling information provided by the appointment scheduling system 116) information including but not limited to: when the appointment is scheduled (e.g., the scheduled appointment time), where the appointment is scheduled (e.g., building and room number), the clinician with whom the appointment is scheduled, the type of appointment, an expected duration of the appointment, pre-appointment preparations to be performed by the patient, and the like. The appointment component 140 can also provide various services related to the appointment via the POEM application 122 of the client device employed by the entity. For example, the appointment component 140 can facilitate checking the patient into the appointment, providing the patient with real-time updated information regarding an expected waiting time, facilitate filling out and receiving intake information, and facilitate preparing questions for the patient to ask during the appointment.

In some implementations, the appointment component 140 can also intelligently and efficiently manage the usage of an estimated waiting time period between the time of arrival of the patient and the estimated time the appointment will commence (e.g., based on real-time updated information regarding the current backlog of the clinician with whom a patient is scheduled). For example, the appointment component 140 can provide the patient with informative material (e.g., literature, video content, audio content, etc.), regarding the appointment, the condition of the patient, and the like for the patient to review while waiting for the appointment to commence. In other implementations, the appointment component 140 can provide the patient with entertainment material (e.g., not related to the appointment). In other implementations, the appointment component 140 can suggest places or points of interests at the healthcare facility for the patient to visit during the waiting period (e.g., the gift shop, the cafeteria, an art exhibit in the west wing, the botanical garden in the east wing, etc.). The particular material recommended to the patient or activity suggested can be based on various factors personalized to the patient's context, preferences, condition, appointment restrictions mental state, estimated duration of the waiting time period and the like. For example, if the patient is nervous or stressed about the upcoming appointment (e.g., based on feedback received from the patient directly and/or based monitored physiological parameters, monitored facial expressions, gestures, etc.) the patient can be provided with funning videos to distract the patient and put the patient at ease. In another example, if the patient isn't allowed to eat N hours before the appointment the appointment component 140 would not recommend visiting the snack bar around the corner. In addition to optimizing patient waiting time, the appointment component 140 can provide similar services to facilitate optimizing the waiting time for individuals assisting or accompanying a patient on their medical appointment. For example, in a scenario wherein an individual that accompanies a patient to an appointment cannot stay with the patient for the entire duration of the appointment (e.g., a surgical procedure), the appointment component 140 can efficiently manage the waiting time of the individual until the individual can be reunited with the patient. In this regard, the appointment component 140 can provide the individual with relevant material (e.g., informative material instructing the individual how to care for the patient at home post appointment), suggest points of interest at the healthcare facility or events/activities at the healthcare facility to attend (e.g., a health cooking demonstration) based on the amount of time the individual will be waiting, and the like. Additional features and functionalities of the appointment component 140 are discussed in greater detail infra with reference to FIG. 3.

The wayfinding component 142 can facilitate navigating an entity to and about a healthcare facility. In particular, many modern healthcare facilities encompass massive campuses with many different interconnected and disconnected buildings, floors, rooms, hallways, and the like spanning across large geographic areas, making them very difficult to navigate. Although GPS technology can facilitate navigating to a mapped coordinate position of the healthcare facility while outdoors, GPS technology cannot provide indoor navigation once within the healthcare facility. Further, GPS is limited in its ability to facilitate differentiating and navigating between complex campuses that consist of several different disconnected and interconnected buildings that are associated with a single medical facility. The wayfinding component 142 can be configured to provide users with real-time navigation information via their respective client devices 120 to guide them through the physical environment of a healthcare facility and to enhance their understanding and experience of the space. In this regard, the wayfinding component 142 can facilitate navigating indoors within a building including between different rooms, floors and points of interest in the building as well as between two or more different buildings of the medical facility based in part on facility information 152 that provides an accurate mapping of indoor and outdoor space of the healthcare facility.

For example, in one or more embodiments, based on information determined by the discovery component 138 identifying a destination location for an entity that has arrived at the healthcare facility, the wayfinding component 142 can facilitate navigating the entity to the destination location by providing the entity, via a mobile device associated with the entity (e.g., a phone, a tablet, a headset, etc.), with real-time navigation information to the destination location. According to this example, if for example the entity is a patient with an appointment with Dr. Rogers in building A, sector 9, floor 3 room 302, the wayfinding component 142 can determine an appropriate route form the patient's current location to the appointment location and provide the patient with real-time navigation information along the route to guide the patient to the destination location. In some implementations for example, the real-time navigation information can include a visual map and/or audile cues directing the patient where to go each step of the way. The wayfinding component 142 can further seamlessly transition between navigating indoors and outdoors, thereby enabling accurate navigating to a particular area of a healthcare facility from an outdoor environment and navigating between different buildings or areas of a healthcare facility that are physically disconnected by an indoor passageway. For example, in some implementations, the wayfinding component 142 can direct a user where to park, and where to be dropped off depending on the particular destination location within the healthcare facility where the user is determined to be going. Once the user has parked or has arrived at an outdoor area of the healthcare facility, the wayfinding component 142 can further guide the user whether to enter the building and where to go once inside the building.

In one or more embodiment, the wayfinding component 142 can facilitate navigating about a healthcare facility based in part on facility information 152 that provides an accurate mapping of the indoor and outdoor space of the healthcare facility and location tracking information that accurately identifies a current location of an entity relative to the physical space of the healthcare facility. In this regard, the facility information 152 can provide precise information identifying the relative locations, sizes and shapes of physical structures of the healthcare facility (e.g., buildings, walkways, points of interest, halls, rooms, walls, floors, elevators, stairs, escalators, fixtures, etc.) in three-dimensional space. In some implementations, the facility information 152 can include a three-dimensional model of the healthcare facility. The facility information 152 can also include a two-dimensional map of the healthcare facility, including a two-dimensional map of respective levels or floors of the healthcare facility at different elevations.

The facility information 152 can also identify additional pertinent information about the various physical structures of the healthcare facility, including information identifying the physical structure (e.g., by a name, a room number, a building number, etc.), the purpose of the physical structure, a description of the physical structure, historical information associated with the structure, current events or activities associated with the structure, and the like. The wayfinding component 142 can further providing a user with relevant information about the structure as it pertains to the user in association with navigating the facility. For example, if a user has an appointment at the imaging department to have an imaging study performed at a future point in time (e.g., later in the afternoon after a first medical appointment scheduled for the patient that day, next week, etc.), the wayfinding component 142 can provide the user with information (e.g., in an audible format, it a visual format, in a text format, etc.), noting that the patient is passing by the imaging department where the user is scheduled to have an imaging study done later. In another example, if the user has an interest in art, the wayfinding component 142 can point out and describe notable artworks on in the facility as the user passes by them. On the other hand, if the user is more of a history buff, the wayfinding component 142 can provide historical information regarding notable events and occurrences associated with different areas of the healthcare facility as the user passes by.

The wayfinding component 142 can employ various techniques to regularly (or continuously) receive or determine location information identifying a current location of an entity relative to the physical space of a healthcare facility. The location information can identify a current position, orientation (or direction the entity is facing or moving), and elevation of the entity relative to the physical space of the healthcare facility. In this regard, the location information can provide a three-dimensional coordinate position of the entity and provide for determining what floor or level of a building the entity is located. In some embodiments, the wayfinding component 142 can receive location information identifying the current location of an entity (e.g., wherein the location includes position, orientation and elevation information) about or within a healthcare facility from the location system 114. In one implementation of these embodiments, as discussed above the location system 114 can determine, (or provide the wayfinding component 142 with raw data to determine), the elevation information based on electromagnetic information associated with a ground upon which one or more buildings of the healthcare facility are established. In another embodiment, the wayfinding component 142 can include the location system 114 or vice versa. In another embodiment, the wayfinding component 142 can receive information regarding a current location of a user from the facility surveillance system 112. In another embodiment, the wayfinding component 142 can receive location information regarding a current location of an entity directly from the client device 120 associated with the entity (e.g., as determined by the location component 130). Additional features and functionalities of the wayfinding component 142 are discussed in greater detail infra with reference to FIG. 4.

The tracking component 144 can further monitor changes in location information associated with an entity to track the movement of the entity about a healthcare facility. The wayfinding component 142 can further employ information identifying the movement and direction of travel of an entity about the healthcare facility to map the entities location in real-time as the entity moves about the environment and to further dynamically adapt navigational cues to account for changes in the entities' location. In this regard, the tracking component 144 can determine a direction of travel, a speed of travel, an elevation of travel, and the like of an entity as the entity moves throughout the healthcare facility. In the embodiment shown, the tracking component 144 can include patient tracking component 146 that can be tailored to track information regarding location and movement of a patient and visitor tracking component 148 that can be tailored to track information regarding location and movement of a visitor. continue to track a location of an identified entity. Additional features and functionalities of the tracking component 144 are discussed in greater detail infra with reference to FIG. 5.

Figure 2:
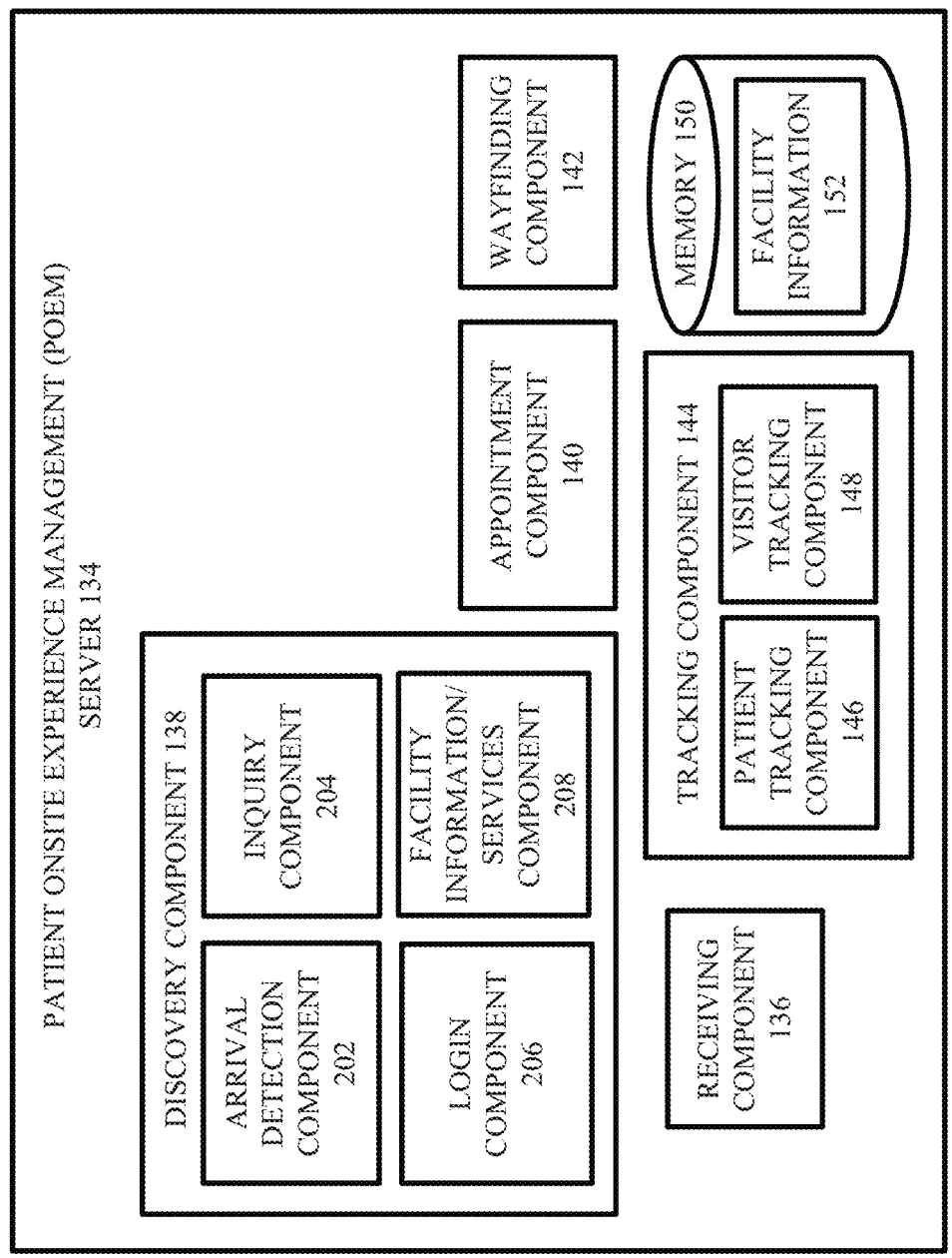
FIG. 2 illustrates some example components associated with the patient onsite experience management (POEM) server that facilitate discovering the intent of entities arriving at a medical facility in accordance with various aspects and embodiments described herein.

FIG. 2 illustrates some example components associated with the POEM server 134 that facilitate discovering the intent of entities arriving at a medical facility by the discovery component 138 in accordance with various aspects and embodiments described herein. In the embodiment shown, these components are associated with the discovery component 138 and include arrival detection component 202, inquiry component 204, login component 206, and facility information/services component 208. One or more of the arrival detection component 202, the inquiry component 204, the login component 206 and the facility information/services component 208 can facilitate determining information regarding when an entity arrives at the healthcare facility, where they have arrived, who the entity is, and the purpose or intent of their visit to the healthcare facility. Repetitive description of like elements employed in respective embodiments is omitted for sake of brevity.

With reference to FIGS. 1 and 2, in one or more embodiments, the arrival detection component 202 can be configured to determine information regarding when an entity arrives at the healthcare facility and where they arrive based on location information determined and/or provided by the facility surveillance system 112, the location system 114 and/or a client device 120 associated with the user (e.g., as determined by the location component 130). For example, the receiving component 136 can be configured to receive and/or regularly pull location information from the facility surveillance system 112, the location system 114, and/or the client devices 120 (e.g., via the location component 130) to determine when and where an entity arrives at the healthcare facility. In some embodiments, the arrival detection component 202 can also determine the identity of an entity arriving at the healthcare facility. For example, in one implementation, the arrival detection component 202 can determine the identity of an entity arriving at the healthcare facility based on information provided by the client device 120 that identifies the client device 120 (e.g., a client device identifier) and information included in patient information 104, the visitor information 106 or the employee information associates the client device identifier with the entity identity. According to this implementation, via the POEM application 122, the user of the client device can authorize tracking of the location of the client device 120 by the POEM server 134 in association with receiving services from the POEM server 134.

In another implementation, the arrival detection component 202 can be configured to determine the identity of the entity based on information provided by the facility surveillance system 112 that can be used to determine the identity of the entity (e.g., a facial image, biometric information, and the like) based on corresponding information included in the patient information 104, the visitor information 106 or the employee information. For instance, in some implementations in which the facility surveillance system 112 employs various sensors to monitor passage of entities through defined physical locations (e.g., doors, property lines, etc.), the receiving component 136 can receive information indicating and potentially identifying the entity at the respective physical locations. The information identifying the entity can be based on facial recognition (e.g., in implementations in which the facility surveillance system 112 employs video or camera surveillance techniques), usage of a key, access code or other form of authorization information that is tied to entity identification information (e.g., in the patient information 104, the visitor information 106, or the employee information 108), or the like. In other embodiments, the facility surveillance system 112 can determine the identity of the entity and provide the arrival detection component 202 with information identifying the entity arriving at the healthcare facility.

The inquiry component 204 can be configured to provide various features and functionalities associated with determining the purpose or intent of an entity that arrives at the healthcare facility. In various embodiments, based on detection of an entity arriving at the healthcare facility by the arrival detection component 202, the inquiry component 204 can be configured to generate a greeting that welcomes the entity to the healthcare facility. The client device 120 can further render the greeting to the user. For example, in various embodiments, the client device 120 can receive the information and services provided by the POEM server via the POEM application 122. With these embodiments, the client device 120 can receive and/or render the greeting via the POEM application 122 when the POEM application is open or otherwise activated or running at the client device 120. If the identity of the entity is known, the greeting can welcome the entity by name. In some embodiments, if the client device 120 does not have the POEM application 122, based on detecting the arrival of the entity at the healthcare facility, the inquiry component 204 can generate and send the client device with a prompt directing the client device 120 to download and activate the POEM application to receive the information and services provided by the POEM server 134. In other implementations, the client device 120 can be configured to automatically download and/or activate the POEM application 122 in response to detection of arrival of a user associated with client device 120 at the healthcare facility.

In some embodiments, the POEM application 122 can be configured to provide users with information and services of the POEM server 134 based on establishment and login to a user account for the user. With these embodiments, the login component 206 can facilitate establishing and logging a user into their account with the POEM server 134. For example, the login component 206 can allow patients, visitors, employees and the like that desire to receive the information and services provided by the POEM server 134 to initially access the POEM server using the POEM application 122 on their respective client devices 120 and register or otherwise establish a user account with the POEM server 134. For instance, in order to establish a user account, the user can set up a profile or account name (e.g., username) and account access information (e.g., password). The information received by the login component 206 in association with establishing a patient account can further be stored by the POEM server 134 (e.g., in memory 150 as user account information) or associated with the user identity in the patient information 104, the visitor information 106 or the employee information (e.g., depending on whether the user registers as patient, visitor, or employee). With these embodiments, based on activation and login of a user to the POEM application 122 at a client device 120 in association with arrival of a user of the client device 122 at the healthcare facility, the inquiry component 204 can determine the identity of the user arriving at the healthcare facility based on information associating the user identity with the corresponding account.

In embodiments in which the inquiry component 204 receives information identifying an entity arriving at the healthcare facility or otherwise determines the identity of an entity arriving at the healthcare facility, the inquiry component 204 can be configured to initially access and evaluate the information provided by the one or more external sources and systems 102 to determine or infer (e.g., based on machine learning analysis of historical data) the purpose or intent of the entity at the healthcare facility. For example, based on information identifying a user, the inquiry component 204 can be configured to access the patient information 104, the visitor information 106 and the employee information 108 to determine additional information about the user that may be associated with the user in the patient information 104, the visitor information 106 or the employee information, respectively. In some implementations in which the entity is a patient of the healthcare facility, the inquiry component 204 can be configured to access and evaluate the appointment scheduling system 116 to determine if the patient has any upcoming appointments scheduled. If the patient has an upcoming appointment scheduled at the healthcare facility on the day the patient has arrived, the inquiry component 204 can determine or infer (e.g., based on machine learning analysis of historical data) that the reason for the patient's visit to the healthcare facility is to attend the medical appointment. The inquiry component 204 can further determine the particular location of the medical appointment and any relevant information about the medical appointment using the information provided by the appointment scheduling system 116 (e.g., the purpose of the appointment, relevant preparations the patient should perform for the appointment and the like).

If the entity arriving at the healthcare facility is a known visitor for which information is provided in the visitor information 106, the inquiry component 204 can be configured to evaluate the visitor information 106 to determine any relationships between the visitor and a current patient of the healthcare facility. For example, the inquiry component 204 can determine if the visitor is related to (e.g., as a friend or family member, as a primary caretaker or guardian, or the like) a patient of the healthcare facility and the status of the patient. For example, regarding the status of the patient, the inquiry component 204 can determine if the patient is a current admitted patient of the healthcare facility, a patient that is located at the healthcare facility for a medical appointment, a patient that is currently undergoing a medical procedure, a patient that is checked into a medical appointment, and the like. The inquiry component 204 can further determine or infer (e.g., based on machine learning analysis of historical data) the intent of the visitor at the healthcare facility based on the status of a patient related to the visitor. For example, if the visitor is related to an admitted patient, the inquiry component 204 can determine or infer (e.g., based on machine learning analysis of historical data) that the visitor has come to the healthcare facility to visit the admitted patient. The inquiry component 204 can further determine the location of the admitted patient at the healthcare facility and other relevant information associated with visiting the patient (e.g., visiting hours, the current medical status of the patient, and the like).

In some embodiments, the inquiry component 204 can be configured to generate and provide the user with questions via the POEM application to facilitate determining the intent of the user in association with arriving at the healthcare facility. For example, the questions can be presented to the user in the form of a prompt or questionnaire. In another example, the inquiry component 204 can include or provide a chat-bot that provides machine learning based conversation functionality to automatically receive and respond to user input in association with determining the user's purpose at the healthcare facility and providing the user with relevant information to enhance the user's experience at the healthcare facility. The inquiry component 204 can further determine or infer the intent of the user based on the user's responses to the questions. For example, in one implementation, in association with greeting the user upon arrival, the inquiry component 204 can generate a prompt that directly asks the user why the user is visiting the healthcare facility today. The prompt can allow the user to provide input answering the question in free form or allow the user to select one or more options from a predefined list. In some implementation, the specific questions asked by the inquiry component 204 can be tailored based on known information associated with the user (e.g., provided by the one or more external sources and systems 102) and the user's previous responses to questions asked. For example, based on information indicating a user arriving at the healthcare facility is a visitor, the inquiry component 204 can if the user is here to see a particular patient that the visitor has a known relationship with.

In some embodiments, the POEM application 122 can facilitate finding and accessing information about the healthcare facility via the facility information/services component 208. For example, the facility information/services component 208 can provide users access to information about the healthcare facility regarding can points of interest at the healthcare facility (e.g., medical departments and offices, clerical departments and offices, dining facilities, shopping facilities, exercise facilities, etc.), events at the healthcare facility, services provided at the healthcare facility, physicians employed by the healthcare facility, and the like. This information can be stored in memory 150 (e.g., as facility information 152) or otherwise accessible to the facility information/services component 208. With these embodiments, the inquiry component 204 can further determine information regarding an intent of a user at the healthcare facility based on user interaction with the POEM application 122 in association with selecting and accessing information regarding the healthcare facility information/services of the healthcare facility. For example, based on selection of a point of interest at the healthcare facility, the inquiry component 204 can determine that the user is interested in visiting the point of interest or other points of interest that are related to the point of interest. In some embodiments, based on selection of a particular point of interest and a request to navigate to the point of interest, the wayfinding component 142 can provide the user with real-time navigation information that navigates the user to the selected point of interest.

Figure 3:
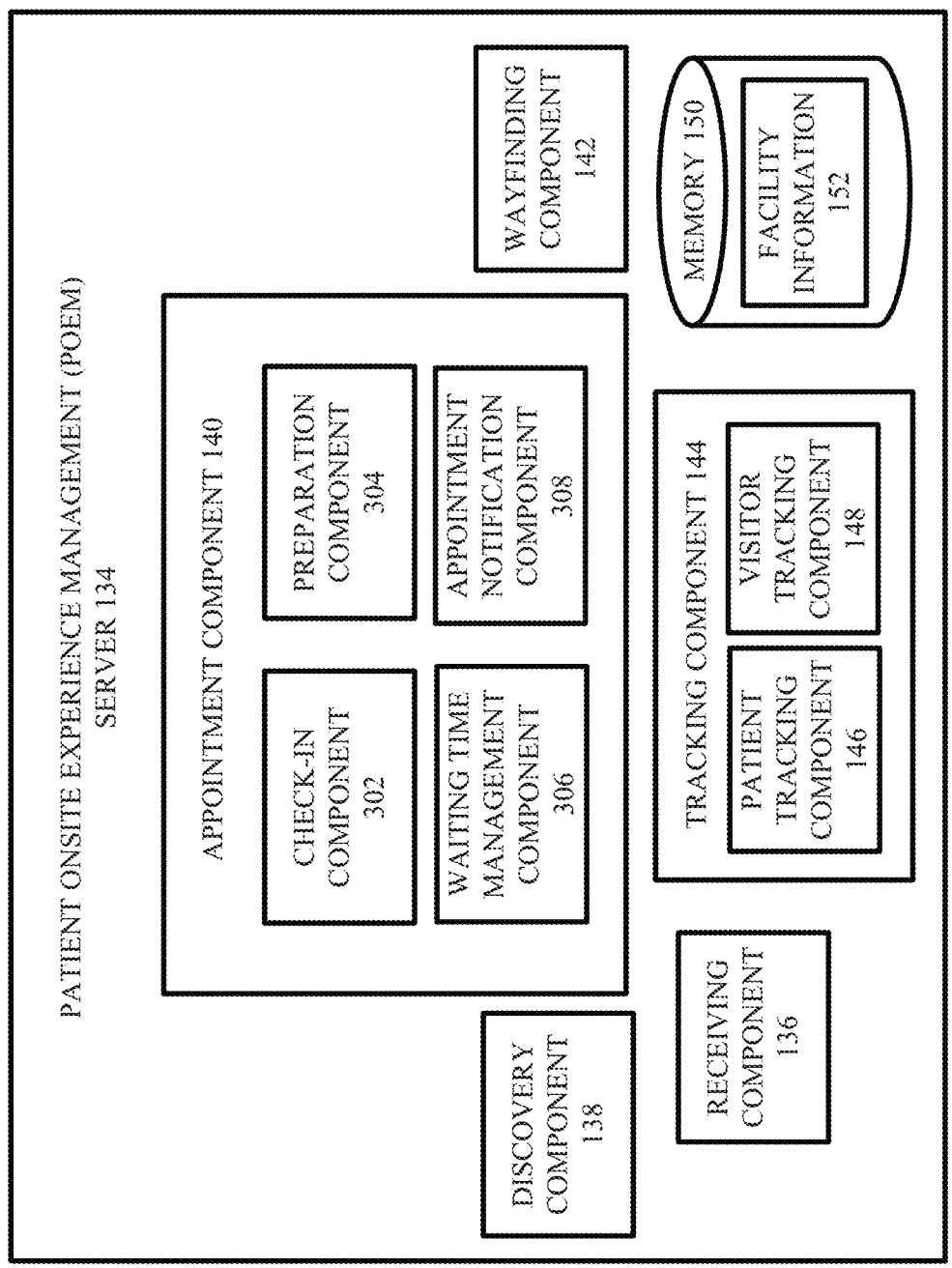
FIG. 3 illustrates some example components associated with the POEM server that facilitate managing and optimizing the user experience at a medical facility in association with attending medical appointments at the healthcare facility in accordance with various aspects and embodiments described herein.

FIG. 3 illustrates some example components associated with the POEM server 134 that facilitate managing and optimizing the user experience at a medical facility in association with attending medical appointments at the medical facility in accordance with various aspects and embodiments described herein. In the embodiment shown, these components are associated with the appointment component 140 and can include check-in component 302, preparation component 304, waiting time management component 306, and the appointment notification component 308. Repetitive description of like elements employed in respective embodiments is omitted for sake of brevity.

With reference to FIGS. 1 and 3, in one or more embodiments, the check-in component 302 can be configured to facilitate checking a patient into a medical appointment at the healthcare facility. In some implementations, the appointment component 140 can provide a patient (or authorized agent assisting the patient) with information identifying upcoming medical appointments scheduled for the patient. The appointment information can be presented to the user at the client device 120 via a GUI that allows the user to select an appointment to view information regarding the appointment and to provide input that results in checking into the appointment. In this regard, based on reception of user input requesting to check into an upcoming appointment, the check-in component 302 can interface with the appointment scheduling system 116 to change the patient's status to being checked into the medical appointment with the appointment scheduling system 116.

In some implementations, the check-in component 302 can restrict the ability for a patient to check into a medical appointment based on time and/or location. For example, in one implementation the check-in component 302 can restrict check-in ability to a defined time window prior to the scheduled time of the medical appointment (e.g., 24 hours, 2 hours, 1 hour, 30 minutes, etc.). In another implementation, the check-in component 302 can restrict check-in based on the location of the patient relative to the location of the medical appointment location. In this regard, the check-in component 302 can restrict check-in ability to enable patients to only check in when located within a defined distance relative to the medical appointment location. For example, the defined distance can be based on the patient being located anywhere at the medical facility (e.g., check-in ability can be activated based on the patient arriving at the healthcare facility), based on the patient being at the actual location of the medical appointment within the medical facility (e.g., check-in ability can be active based on the patient arriving at the appointment location within the medical facility), and the like. In some embodiments, the check-in component 302 can generate and/or otherwise cause a prompt or notification to be presented to the patient at the client device 120 (e.g., via the POEM application) when check-in ability is activated. For example, the prompt can prompt or remind the patient to check into the appointment and facilitate receiving user input that results in checking the patient into the appointment.

The appointment component 140 can also track the progress of a patient's medical appointment from initiation to check-out and update the appointment scheduling system 116 accordingly. For example, in some embodiments, the appointment component 140 can determine when the medical appointment actually begins based on location information indicating the patient has moved from the waiting room into the area where the patient will be seen or treated by the clinician (e.g., the exam room, the procedure room, etc.). The appointment component 140 can further automatically update the patient's status with the appointment scheduling 116 to indicate the patient is currently participating in the medical appointment. In another implementation, a clinician, technician or another appropriate entity responsible for calling a patient into the medical appointment to begin the medical appointment can interface with the appointment scheduling system 116 to change the patient's status to being currently participating in the medical appointment.

The appointment component 140 can also facilitate updating the appointment scheduling system 116 to indicate when the patient has checked-out of or otherwise completed a medical appointment. In some implementations, the appointment component 140 can automatically check a patient out of an appointment based on the location of the patient exiting the exam room or moving out of a defined distance from the appointment location and remaining outside the defined distance for a defined period of time (e.g., 15 minutes, 30 minutes, etc.). In another implementation, the check-in component 302 can also allow the patient to provide input via the POEM application 122 marking the patient's status to being checked out of an appointment and update the patient's status with the appointment scheduling system 116 accordingly. In yet another implementation, a clinician, technician or another appropriate entity responsible for managing checking patients out of the medical appointment can interface with the appointment scheduling system 116 to change the patient's status to being currently participating in the medical appointment to being check out.

The preparation component 304 can facilitate preparing a patient for an upcoming medical appointment using the POEM application 122. In some embodiments, prior to the timing of a scheduled medical appointment, the preparation component 304 can determine preparation information regarding things the patient should and should not do to prepare for the appointment, things the patient should bring to the appointment (e.g., insurance cards, medications, imaging study reports, etc.), and the like. For example, the preparation component 304 can determine information regarding how a patient should prepare for an upcoming appointment based on information included in the auxiliary information resources 110 defining or indicating preparation requirements for different types of medical appointments, medical procedures, medical conditions and the like. The preparation component 304 can further provide the patient with this preparation information via the POEM application 122 at appropriate times leading up to the time of the scheduled medical appointment. For example, if a patient should stop drinking liquids two hours prior to the appointment time, the preparation component 304 can inform the patient accordingly. In some implementation, the preparation component 304 can generate and provide the patient with a notification (e.g., at the client device via the POEM application 122) at the two hour mark prior to the appointment that reminds the patient not to drink any liquids. The preparation component 304 can also facilitate providing the healthcare facility with the appropriate patient information needed prior to the appointment (e.g., health record information, insurance information etc.). For example, the preparation component 304 can provide the patient with an electronic version of the patient intake forms needed for an appointment and direct the patient to fill out and submit the intake form using the POEM application 122 prior to the appointment. In some embodiments, the preparation component 304 can determine or infer a subset of questions that are relevant to the patient to include on the patient intake form based on information associated with the patient (e.g., in the patient information 104) regarding the patient's condition or diagnosis, the reason for the appointment, the patient's EMR, the patient's demographics (e.g., age, occupation, etc.), the patient's preferences, the patient's current mental and physical state, and the like.

In some embodiments, the preparation component 304 can facilitate preparing the patient with appropriate questions to ask the clinician during an upcoming medical appointment. The preparation component 304 can further automatically provide the prepared questions to the clinician prior to or during the appointment. Alternative, the preparation component 304 can facilitate storing (e.g., at the client device 120 or at the POEM server 134) the list of prepared questions for easy access by the patient during the medical appointment to facilitate ensuring the patient does not forget to ask the clinician the prepared questions. For example, based on information indicating the type of medical appointment, the condition or diagnosis of the patient, and the like, the preparation component 304 can present the patient with known medical questions that are frequently asked by other similar patients that have attended same or similar medical appointments. In some embodiments, the preparation component 304 can determine or infer a subset of questions that are relevant to the patient based on information associated with the patient (e.g., in the patient information 104) regarding the patient's condition or diagnosis, the reason for the appointment, the patient's EMR, the patient's demographics (e.g., age, occupation, etc.), the patient's preferences, the patient's current mental and physical state, and the like. The preparation component 304 can also determine or infer a subset of relevant questions that are relevant to a particular medical appointment based on the skillset or expertise of the clinician or clinicians that will perform the medical appointment. The patient can further provide input selecting one or more of the questions that the patient would like to have the clinician answer in-person during the actual appointment. In some embodiments, the preparation component 304 can automatically provide the patient with predefined or machine generated answers to selected questions. If the patient is satisfied with a predefined or machine generated answer to a question, the patient can eliminate the question from the list of potential questions to ask the clinician during the appointment.

The waiting time management component 306 can facilitate determining and optimizing the waiting time period for a scheduled medical appointment. For example, although most medical appointments are initially scheduled for a specific time, the actual time at which the patient is seen can vary depending on the events of the day and the clinician's schedule. In some scenarios, the clinician may be ahead of schedule and can see a patient earlier than the scheduled appointment time, while in others, the clinician may be behind schedule resulting in an extended wait time.

In one or more embodiments, the waiting time management component 306 can determine an estimated waiting time period based on scheduling information provided by the appointment scheduling system 116 that tracks (e.g., in real-time or substantially real time) the status of patients (e.g., checked-in, in-progress, and checked-out) with respect to an appointment schedule for a clinician. The waiting time management component 306 can also determine or infer the estimated wait time based on information indicating the approximate durations of the scheduled appointments, real-time information regarding changes in the clinician's schedule, and the like. In one implementation, in association with determining and providing a user within an estimated duration of the wait time, the waiting time management component 306 can determine and provide the user with information regarding the number of patients to be seen before the user (e.g., where the user is in the queue). For example, the waiting time management component 306 can monitor the appointment scheduling system 116 to determine an estimated time at which a patient's scheduled medical appointment will begin based on the number of people be seen before the patient, the nature of those patients' appointments, and the schedule of the clinician. The waiting time management component 306 can also determine and provide the patient with real-time updates regarding changes to the estimated waiting time period.

In some implementations, the waiting time management component 306 can be configured to determine and provide a patient with real-time updates regarding the estimated duration of the patient's waiting time period in response to the patient checking into the appointment. In another implementation, the waiting time management component 306 can determine and provide a patient with real-time updates regarding the estimated duration of the patient's waiting time period in response to arrival of the patient at the healthcare facility. In other embodiments, the waiting time management component 306 can be configured to monitor a clinician's schedule and inform a patient regarding significant delays or changes to the patient's scheduled appointment time the day of the appointment. In this regard, the waiting time management component 306 can provide the patient with notifications regarding significant delays or changes so that the patient can adapt accordingly (e.g., leave the house to head to the appointment an hour later based on a notification indicating the clinician is an hour behind schedule).

In addition to determining and informing a user regarding an estimated waiting time period for a medical appointment, the waiting time management component 306 can further facilitate optimizing usage of the waiting time period to improve clinical efficiency and performance of the healthcare facility and improve the overall experience of the user at the healthcare facility. For example, the waiting time management component 306 can facilitate directing a patient to perform appropriate preparations for the medical appointment during the waiting time period, facilitate entertaining the user, facilitate reducing or minimizing stress or anxiety of the user associated with the medical appointment, and the like. For example, in some implementations, the waiting time management component 306 can prompt the user to prepare for the appointment during the waiting time using one or more of the features and functionalities of the preparation component (e.g., filling out intake forms, generating a list of questions to ask the clinician during the appointment, and the like). In another implementation, the waiting time management component 306 can determine and provide the user with relevant auxiliary information selected from the auxiliary information resources 110. For example, the relevant auxiliary information can include informative information regarding the patient's condition, diagnosis and/or describing what to expect during the appointment. In another example, the auxiliary information can include entertaining media (e.g., videos, news articles, games and the like). Still in other implementations, the waiting time management component 306 can determine or infer suggested points of interest, activities, events and the like at the healthcare facility that for the user to visit or attend during the waiting time period. For example, the waiting time management component 306 can suggest a user visit the gift shop, visit the art exhibit in the West wing, attend the community yoga class, etc.

In various embodiments, the waiting time management component 306 can determine or infer appropriate and relevant information to provide a user and/or appropriate actions for performance by the user during a waiting time period based on the current context and one or more personalized factors associated with the user. In this regard, the context can relate to the duration of the waiting time, the type of appointment, preparations and/or restrictions associated with the appointment, the location of the appointment in the healthcare facility, the current time of day, and the like. Personalized factors associated with the user can include but are not limited to: the medical history of the user, a medical condition/diagnosis of the user, a current mental/physical state of the user, demographic characteristics of the user, preferences of the user and the like. For example, with respect to the duration of the waiting time period, the waiting time management component 306 can determine first information and/or actions if the waiting time period is first duration, second information and/or actions if the waiting time period is second duration, third information and/or actions if the waiting time period is third duration and the like. For example, the waiting time management component 306 can determine an appropriate length version of an instructional video about the appointment to provide to the user prior to the appointment based on the duration of the waiting time (e.g., if waiting time is less than 15 minutes, the waiting time management component 306 can provide the user with the short version of the video as opposed to the full length version).

The appointment notification component 308 can be configured to notify a patient when their appointment is about to begin. In this regard, based on scheduling information indicating the patient is next in the queue or the appointment will begin in less than a defined duration (e.g., five minutes), the appointment notification component 308 can generate and send the user a notification at their client device 120 (e.g., via the POEM application) instructing the user that their appointment is about to begin. In some implementations, in which the patient has left the appointment location to go to a point of interest at the healthcare during the waiting time period, the appointment notification component 308 can factor in the patient's current location relative to the appointment location, the user's pace and other potential information that can have an impact on the amount of time it will take the patient to return to the appointment location, when notifying the user. In this regard, the appointment notification component 308 can determine an amount of time it will take the user to return to the appointment location and generate and send a notification to the user prompting the user to return to the appointment location based on the amount of time. For example, if the user is ten minutes away from the appointment location, the appointment notification component 308 can be configured to notify the user at about fifteen minutes prior to when their appointment is about to begin and instruct the user to return to the appointment location so that the user has enough time to return to the appointment location.

Figure 4:
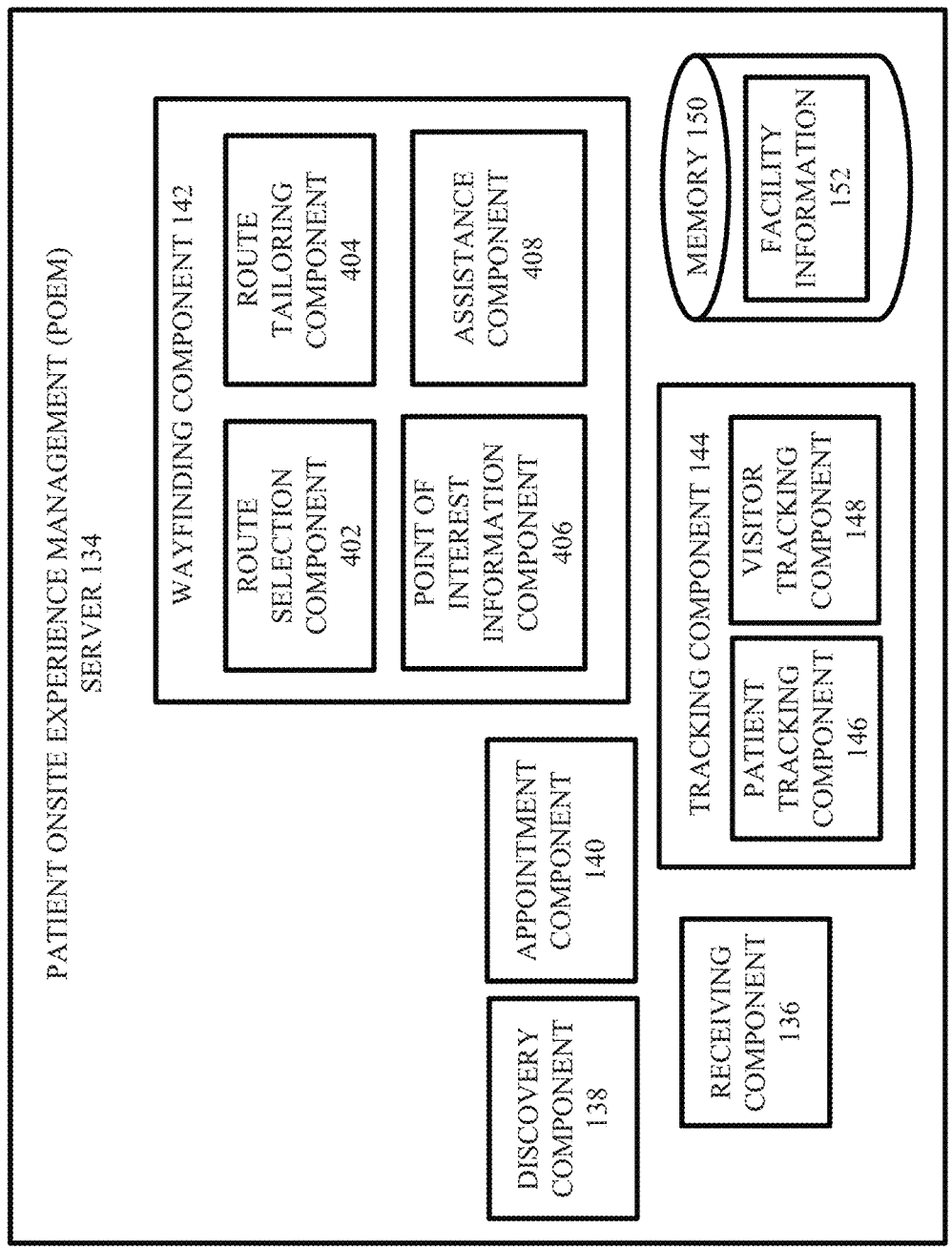
FIG. 4 illustrates some example components associated with the POEM server that facilitate managing and optimizing the user experience at a medical facility in association navigating throughout the healthcare facility in accordance with various aspects and embodiments described herein.

FIG. 4 illustrates some example components associated with the POEM server that facilitate managing and optimizing the user experience at a medical facility in association navigating throughout the medical facility in accordance with various aspects and embodiments described herein. In the embodiment shown, these components are associated with the wayfinding component 142 and can include route selection component 402, route tailoring component 404, point of interest information component 406 and assistance component 408. Repetitive description of like elements employed in respective embodiments is omitted for sake of brevity.

With reference to FIGS. 1 and 4, in one or more embodiments, the route selection component 402 can be configured to determine a route between two or more points of interest relative to the healthcare facility for following by an entity (e.g., a patient, a visitor, an intelligent machine, a self-driving vehicle, etc.). In some implementations, the route selection component 402 can determine a route that directs a user from a current location to a determined or selected destination location at or within the healthcare facility. For example, in association with determination of a destination location within a healthcare facility based on arrival of an entity at the healthcare facility, the route selection component 402 can determine a route from the entities' arrival location to the destination location. In other implementations, the route selection component 402 can determine route information between two or more locations that do not include a current location of the user. For example, the route selection component 402 can determine a route between an two or more anticipated points of interest that the user may visit at the healthcare facility.

In some embodiments, the route selection component 402 can select a route from a set of predefined routes included in the facility information 152. According to these embodiments, the facility information 152 can include predefined routes between various locations and points of interest at the healthcare facility. In other embodiments the route selection component 402 can determine the route based on facility information providing an accurate three-dimensional model or map of the healthcare facility, including the relative locations of physical structures (e.g., walls, doors, rooms, elevators, staircases, buildings, etc.). In some implementations, the route selection component 402 can be configured to select the quickest route, the easiest route, or another predefined type of route by default.

The route tailoring component 404 can be configured to tailor one or more aspects of a route selected or determined by the route selection component 402 based on a current context and/or one or more personalized factors associated with the entity. For example, the route tailoring component 404 can adapt or change a route based on an estimated wait time prior to initiation of an appointment, based on one or more events or occurrences at the healthcare facility, based on a current mental or physical state of the user, based on a physical disability of the user, based on preferences of the user, based on interests of the user, based on restrictions associated with an upcoming medical appointment, based on the pace of the user, etc.

The point of interest information component 406 can be configured to facilitate providing a user with relevant information regarding one or more points of interest at the healthcare facility in association with navigation about the healthcare facility. For example, in some implementations, the point of interest information component 406 can determine and provide the use with information regarding points of interest as the user passes by. The specific information and the specific points of interest that are called out can be based on the current context associated with the entities intent at the healthcare facility as well as one or more personalized factors known about the entity.

The assistance component 408 can be configured to determine information regarding whether a mental or physical condition of the arriving at the healthcare facility need for physical assistance in association with the navigating and schedule appropriate medical personal or equipment to a current location of the entity accordingly. For example, the assistance component 408 can determine if an entity arriving or about to arrive at the healthcare facility needs a wheelchair and schedule one to be delivered to the entity. In another example, the assistance component 408 can determine based on monitored biofeedback information for a patient (e.g., received from one or more biofeedback devices 118) if the patient needs immediate clinical attention and respond with medical personnel accordingly.

FIG. 5 illustrates an additional artificial intelligence component 502 that can be employed by the POEM server 134 to facilitate managing and optimizing the user experience at the medical facility in accordance with various aspects and embodiments described herein. Repetitive description of like embodiments employed in respective embodiments are omitted for sake of brevity.

Various components of the POEM server 134 can employ AI component 502 to perform one or more machine learning techniques to facilitate making inferences regarding association with managing and optimizing the experiences of entities at the healthcare facility. For example, the discovery component 138 can employ the AI component 502 to facilitate determine information regarding an intent of an entity at the healthcare facility. The appointment component 140 can employ AI component 502 to facilitate determine information regarding an estimated wait time and information regarding information and activities to suggest during the waiting period. In another example, the wayfinding component 142 can employ AI component 502 to facilitate determining an optimal and personalized route in association navigation about a healthcare facility. Machine learning is a type of AI that provides computers with the ability to learn without being explicitly programmed. In order to provide for or aid in the numerous inferences described herein, the AI component 502 examine the entirety or a subset of the data to which it is granted access and can provide for reasoning about or infer states of the system (e.g., system 100 and the like), environment, etc. from a set of observations as captured via events and/or data. An inference can be employed to identify a specific context or action, or can generate a probability distribution over states, for example. The inference can be probabilistic (e.g., the computation of a probability distribution over states of interest can be based on a consideration of data and events). An inference can also refer to techniques employed for composing higher-level events from a set of events and/or data. Such an inference can result in the construction of new events or actions from a set of observed events and/or stored event data, whether or not the events are correlated in close temporal proximity, and whether the events and data come from one or several event and data sources. Various classification (explicitly and/or implicitly trained) schemes and/or systems (e.g., support vector machines, neural networks, expert systems, Bayesian belief networks, fuzzy logic, data fusion engines, etc.) can be employed in connection with performing automatic and/or inferred action in connection with the claimed subject matter.

Figure 6:
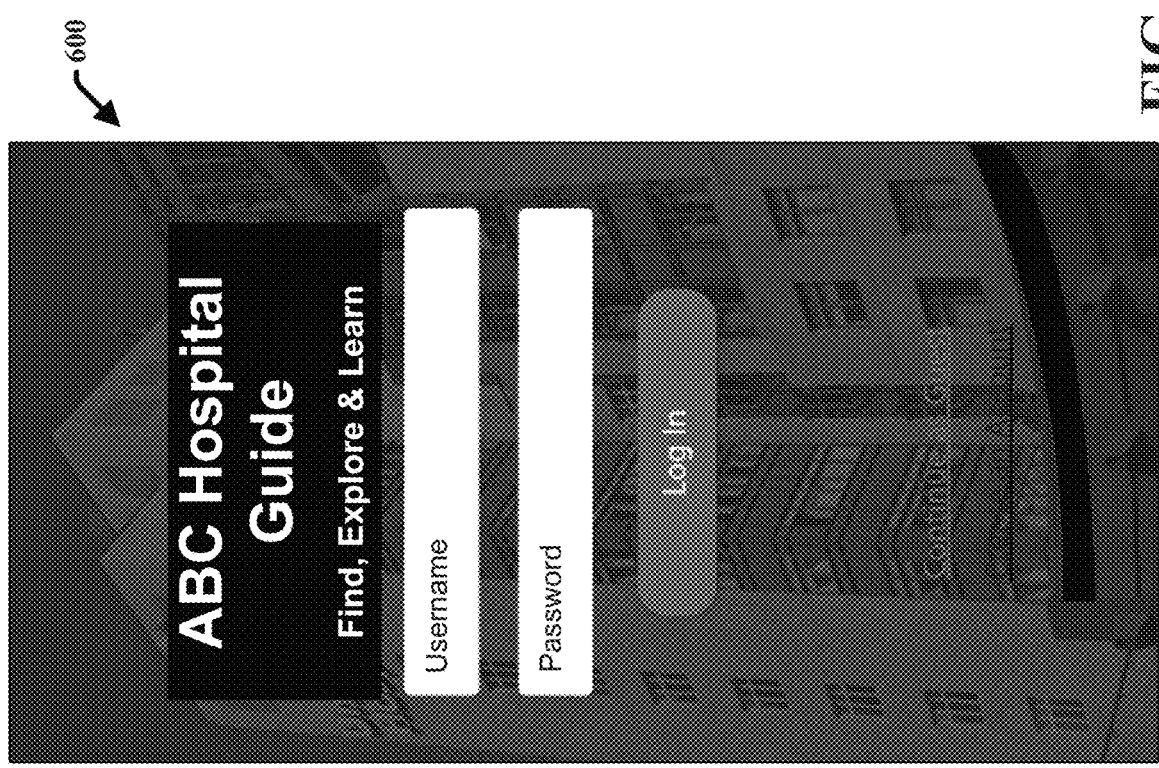
FIG. 6 presents an example login graphical user interface (GUI) that facilitates accessing the features and functionalities of a POEM application either as a user with an established account or as guest in accordance with aspects and embodiments disclosed herein.

A classifier can map an input attribute vector, x=(x1, x2, x4, x4, xn), to a confidence that the input belongs to a class, such as by f(x)=confidence(class). Such classification can employ a probabilistic and/or statistical-based analysis (e.g., factoring into the analysis utilities and costs) to prognose or infer an action that a user desires to be automatically performed. A support vector machine (SVM) is an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority Referring now to FIGS. 6-19, presented are example GUIs illustrating some the features and functionalities of system 100 described with reference to FIGS. 1-5. In one or more embodiments, FIGS. 6-19 present example GUIs that can be generated by the POEM application 122 (e.g., via interface component 124) of a client device 120 to facilitate managing and optimizing the experience of a user of the client device 120 at a medical facility (e.g., ABC hospital) in accordance with various aspects and embodiments described herein. In the embodiments shown in FIGS. 6-16, the GUIs correspond to mobile application GUIs that can be generated and displayed at client device that is a smartphone or tablet type of device. However, it should be appreciated the appearance of the GUIs and the type of client device at which the GUIs are displayed can vary. Repetitive description of like elements employed in respective embodiments is omitted for sake of brevity With reference now to FIG. 6, presented is an example login GUI 600 that facilitates accessing the features and functionalities of the POEM application 122 either as a user with an established account or as guest. In some implementations, the login GUI 600 can be initially presented to a user in association with activating or opening the POEM application 122 if the user is logged out of their account or does not have an established account. In one embodiment, a user with an established account can access personalized features and functionalities of the POEM application 122 provided in association with an established account based on reception of the correct login information (e.g., username and password). If the user does not have an account, the user can continue to the POEM application as guest based on selection of the "continue as guest" option at the bottom of the login GUI 600. In other implementations, if the user does not have an established account, the user can create an account based on selection of the "create an account" option at the bottom of the GUI 600.

Figure 7:
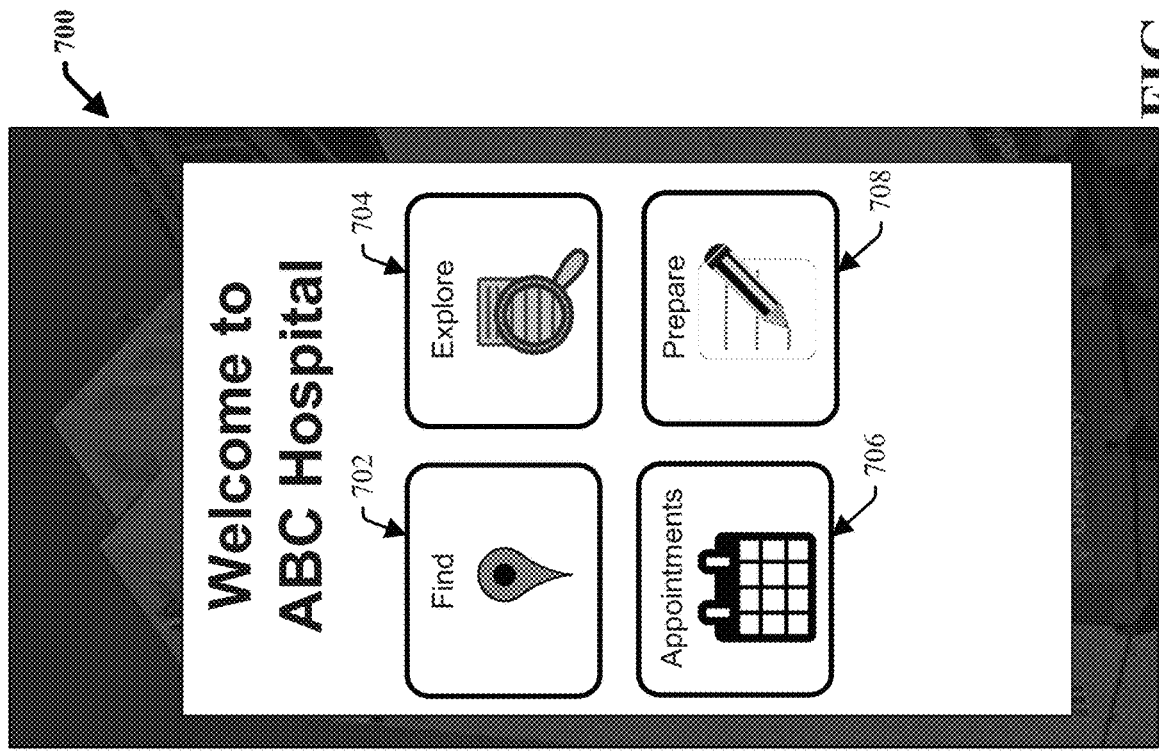
FIG. 7 presents an example main menu or home screen GUI 700 that facilitates selecting one or more functions of the POEM application in accordance with aspects and embodiments disclosed herein.

FIG. 7 presents an example main menu or home screen GUI 700 that can be presented the POEM application 122 that facilitates selecting one or more functions of the POEM application 122, including a find function 702, an explore function 704, an appointments function 706, and an appointment preparation function 708. In one or more embodiments, the find function 702 can facilitate finding places or points of interest associated with physical locations at or within the healthcare facility. In various embodiments, the find function 702 employ or provide features and functionalities of the wayfinding component 142 by allowing users to select a point of interest and receive navigation information to the selected point of interest. The explore function 704 can facilitate exploring and learning information about points of interest, events, and services the healthcare facility offers. In some implementation, the explore function 704 can facilitate learning information (e.g., by the discovery component 138) regarding the intent of a user at the healthcare facility. The explore function 704 can also facilitate accessing informative and entertainment information and media offered by the POEM server 134. The appointments function 706 can provide one or more features and functionalities of the appointment component 140 and the appointment preparation function 708 can provide one or more features and functionalities of the preparation component 304.

Figure 8:
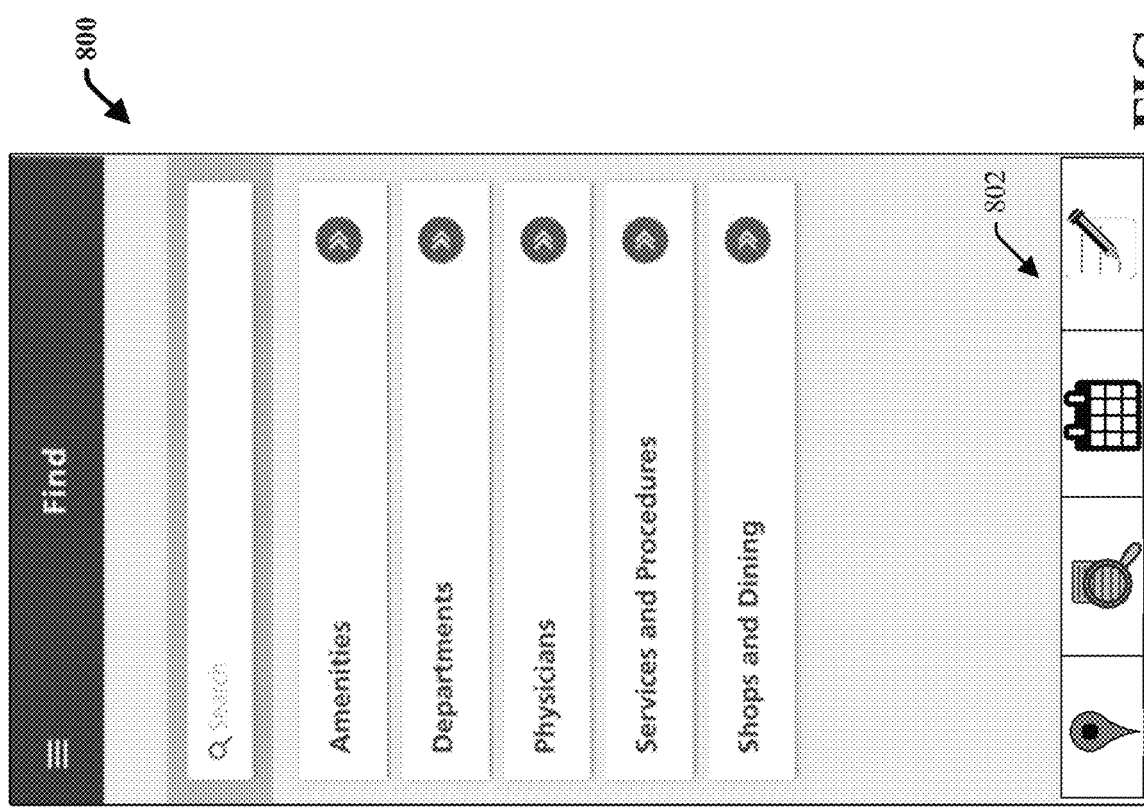

FIG. 8 presents an example find function GUI 800 that can be presented by the POEM application 122 in response to selection of the find function 702 from GUI 700. In some implementations, the POEM application 122 can be configured to generate and render GUI 800 in response to selection of the "continue as guest" option from GUI 600. In the embodiment shown, the find function GUI 800 includes several menu categories providing different types of points of interest that a user can select to find additional information about and to receive information that facilitates navigating the user to a selected particular point of interest. For example, these different categories include amenities, departments, physicians, services and procedures, and shops and dining. The find function GUI 800 also includes a search bar that can search for a particular point of interest based on received user input providing search terms. The find function GUI 800 can also include a lower menu bar 802 that includes hyperlinks to the other functions provided by the POEM application (e.g., the explore function, the appointment function, and the appointment preparation function).

Figure 9:
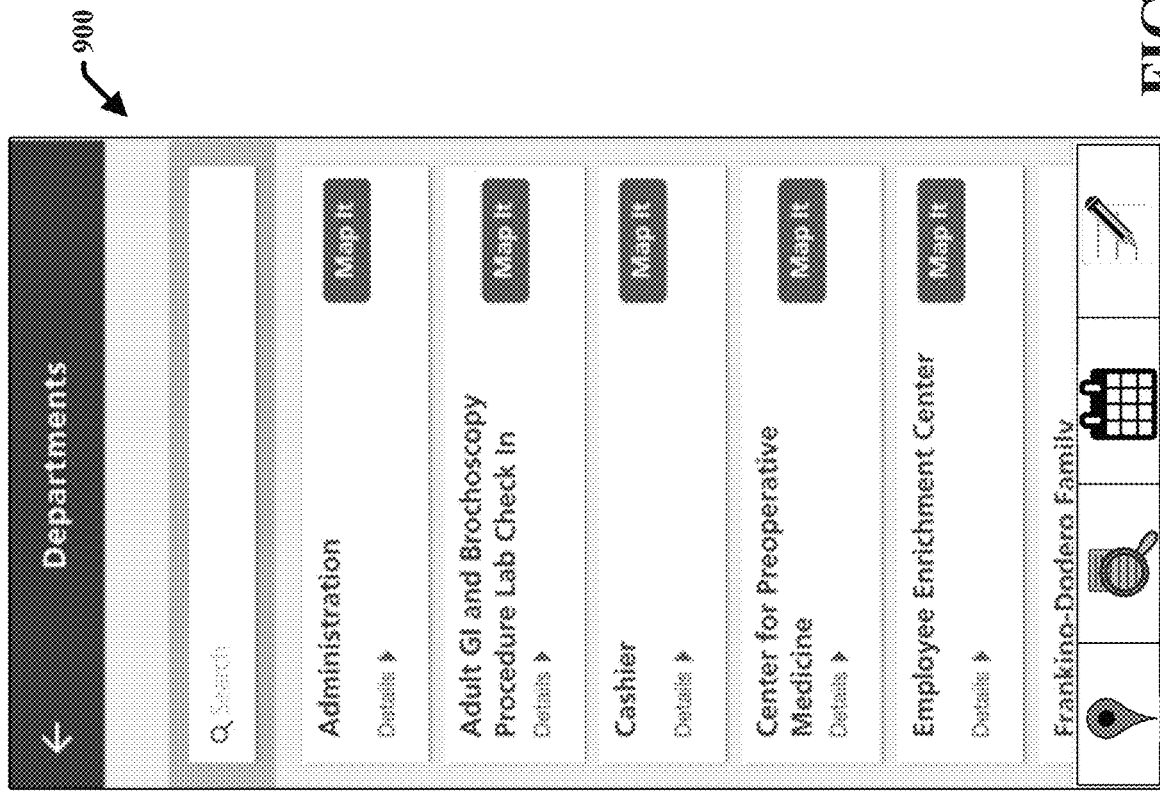
FIGS. 8 and 9 present example GUIs of the POEM application that facilitate selecting points of interest in accordance with aspects and embodiments disclosed herein.

FIG. 9 presents an example departments GUI 900 that can be generated and presented by the POEM application 122 in response to selection of the departments category from the find function GUI 800. In the embodiment shown, different departments of the healthcare facility can be listed in alphabetical order. Each of the departments are associated with a "map it" icon. In various embodiments, selectin of a "map it" icon associated with a place of interest, such as a particular department, can activate the wayfinding functionality of the wayfinding component 142 and provide the user with navigation information for the corresponding point of interest. Additional detailed information about the respective points of interest can also be provided to the user in response to selection of the "details" icon associated therewith.

Figures 10, 11:
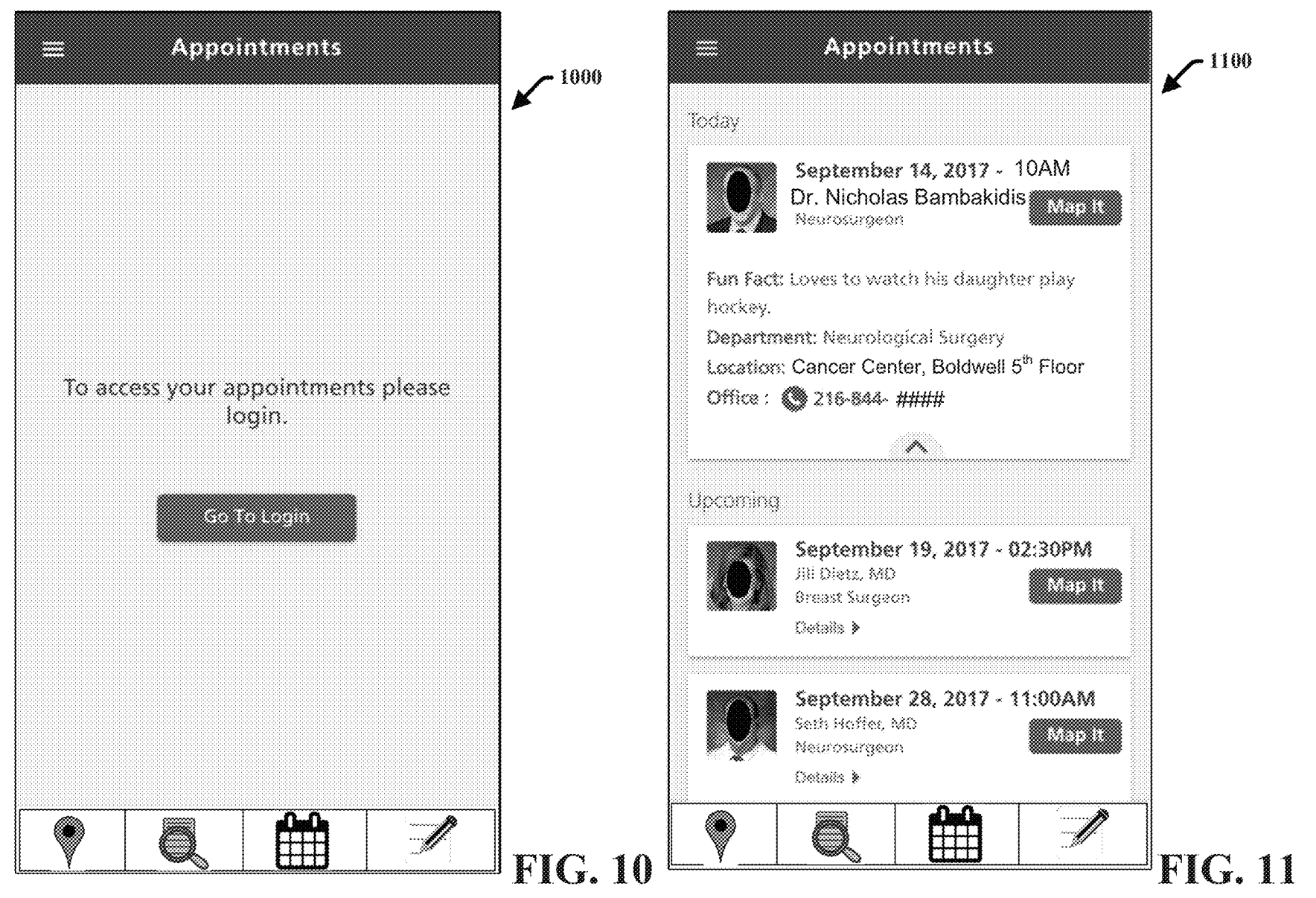

FIG. 10 presents an example appointments function GUI 1000 that can be generated and presented by the POEM application 122 in response to selection of the appointments function 706 from GUI 700. In some implementations, the POEM application 122 can be configured to generate and render the appointments function GUI 1000 in response to selection of the appointments function 706 if the user is not logged into their account. In this regard, the POEM application 122 can restrict access to personal appointment information for a patient to only those authorized to access the appointment information.

FIG. 11 presents another example appointments function GUI 1100 that can be generated and presented by the POEM application 122 to facilitate managing and attending appointments at the healthcare facility. In some implementations, the appointments function GUI 1100 can be generated and presented in response to selection of the appointments function 706 from GUI 700 if the user is logged into their account. For example, in the embodiment shown, the logged in user can include a person that is a patient or an authorized agent for the patient. If the patient has any scheduled appointments, the appointments function can list them in chronological order. For example, in the embodiment shown, the user has one appointment scheduled for the current day and two additional upcoming appointments scheduled for later days. The scheduled appointments can also include a "map it" icon associated therewith. In various embodiments, selection of the map it icon associated with an appointment can activate the functionality of the wayfinding component 142 and result in the provision of navigation information to the location of the appointment, including real-time navigation information to the appointment location.

For example, FIGS. 12A-12F present example GUIs that can be generated and presented by the POEM application 122 in association with providing one or more features and functionalities of the wayfinding component 142 to facilitate real-time navigation of a user to a selected destination location. In the example shown in FIGS. 12A-12F, the destination location is the appointment location of the appointment scheduled for the patient on the current day with Dr. Nicholas Bambakidis. For example, as shown in GUI 1100, the appointment location is the Cancer Center, Boldwell building, $5^{th}$ Floor. In one or more embodiments, the POEM application 122 can generate the GUIs shown in FIGS. 12A-12F in response to selection of the "map it" icon associated with the corresponding appointment from GUI 1100.

Figure 12A:
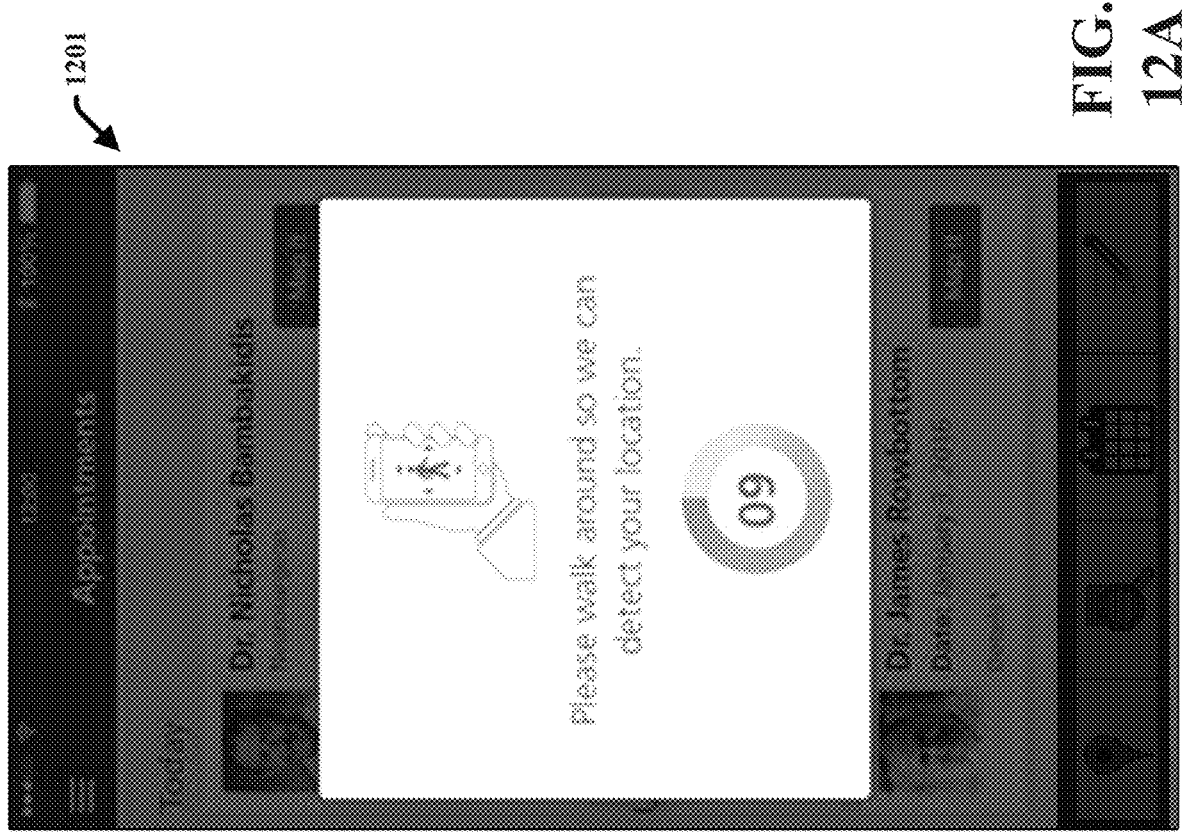
FIGS. 12A-12F present example GUIs of the POEM application associated with the wayfinding functionality in accordance with aspects and embodiments disclosed herein.

With reference to FIG. 12A, presented is a GUI 1201 that can be initially presented to the user to facilitate determining the precise current location of the user and/or client device 120 (e.g., by the wayfinding component 142). As shown in GUI 1201 in order to facilitate determining the current location, the user can be instructed to walk or move around for a defined period of time (e.g., 10 seconds).

Figure 12B:
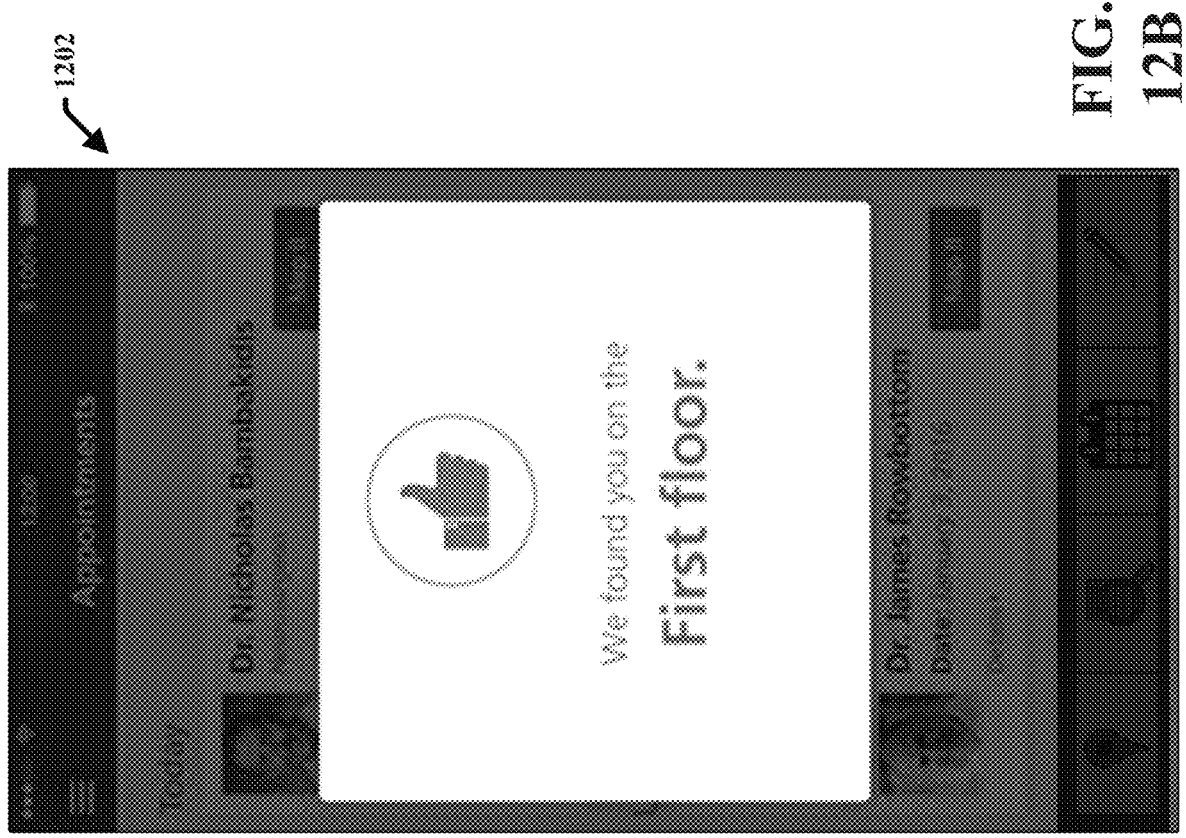

FIG. 12B presents an example GUI 1202 including a prompt that can be presented at the client device 120 when the current floor of the user/client device is determined (e.g., using one or more of the position elevation determination techniques described herein). For example, in the embodiment shown, the POEM application is 122 is notifying the user that they have been found on the first floor.

Figure 12D:
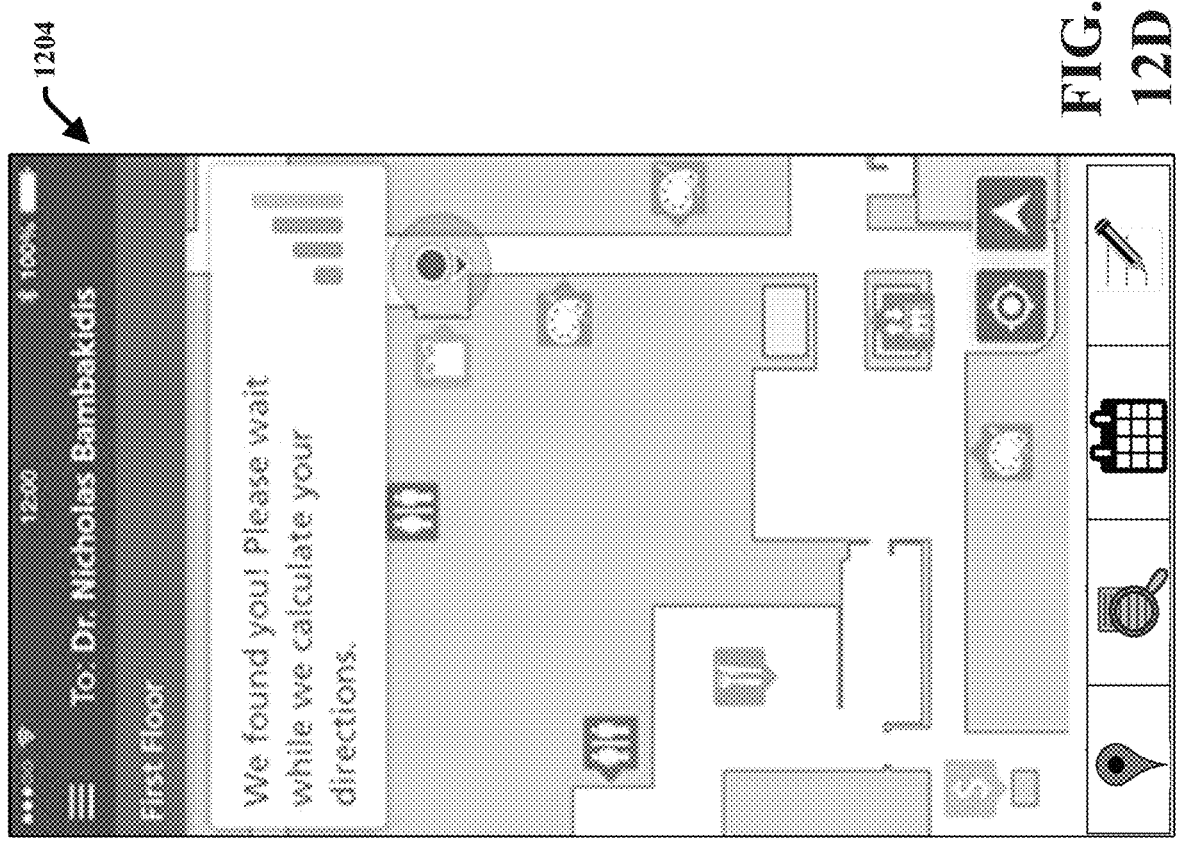
Figure 12C:
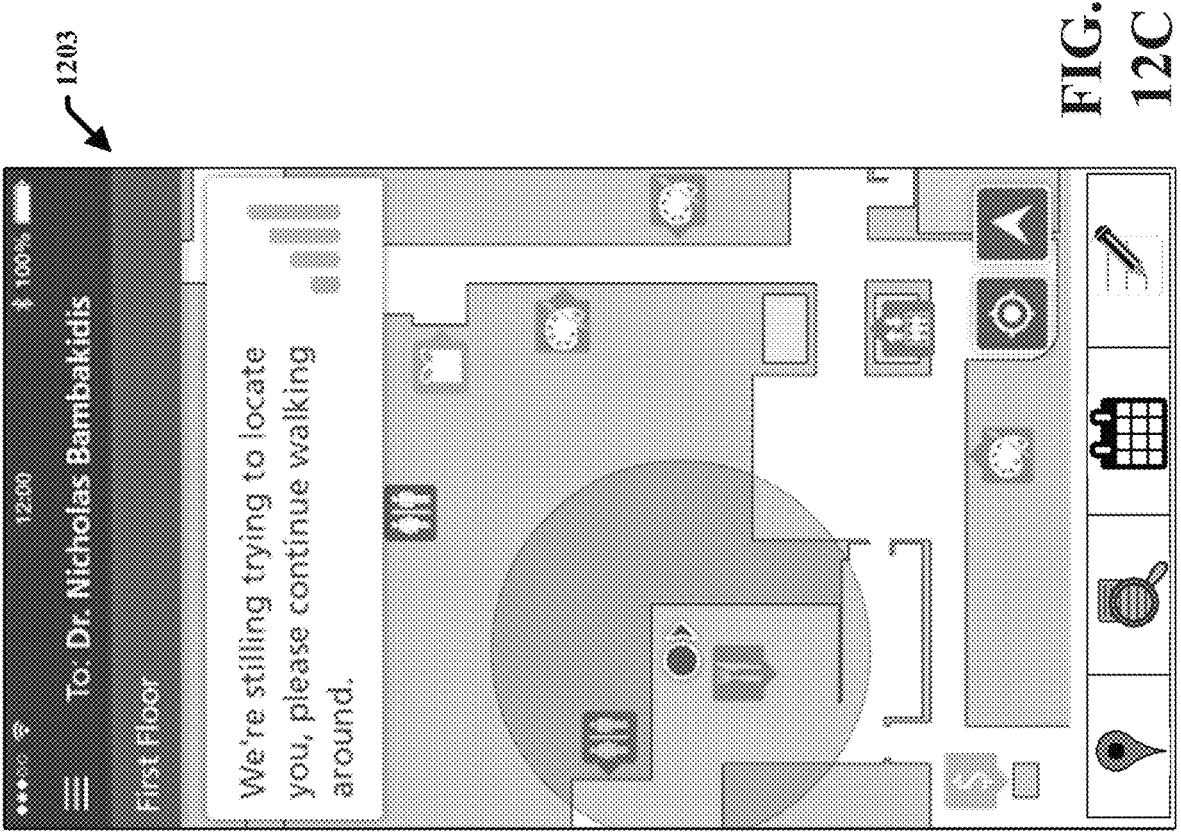

FIG. 12C presents an example GUI 1203 including a map of the healthcare facility on the first floor where the user/client device was found. In the embodiment shown, the user is being instructed to continue walking around as the wayfinding component 142 is still trying to pinpoint the user's exact location. The area where the user/client device is potentially located can be represented by a large circle while the center of the circle indicates an exact or precise location of the user/client device.

FIG. 12D presents an example GUI 1204 that can be presented the user when the wayfinding component 142 has determined (or received information identifying) the exact location of the user/client device relative to the healthcare facility. Once the user's exact location is found, the user can be instructed to wait while the wayfinding component 142 determines the best navigation route (e.g., the directions) to the user's appointment location.

Figure 12F:
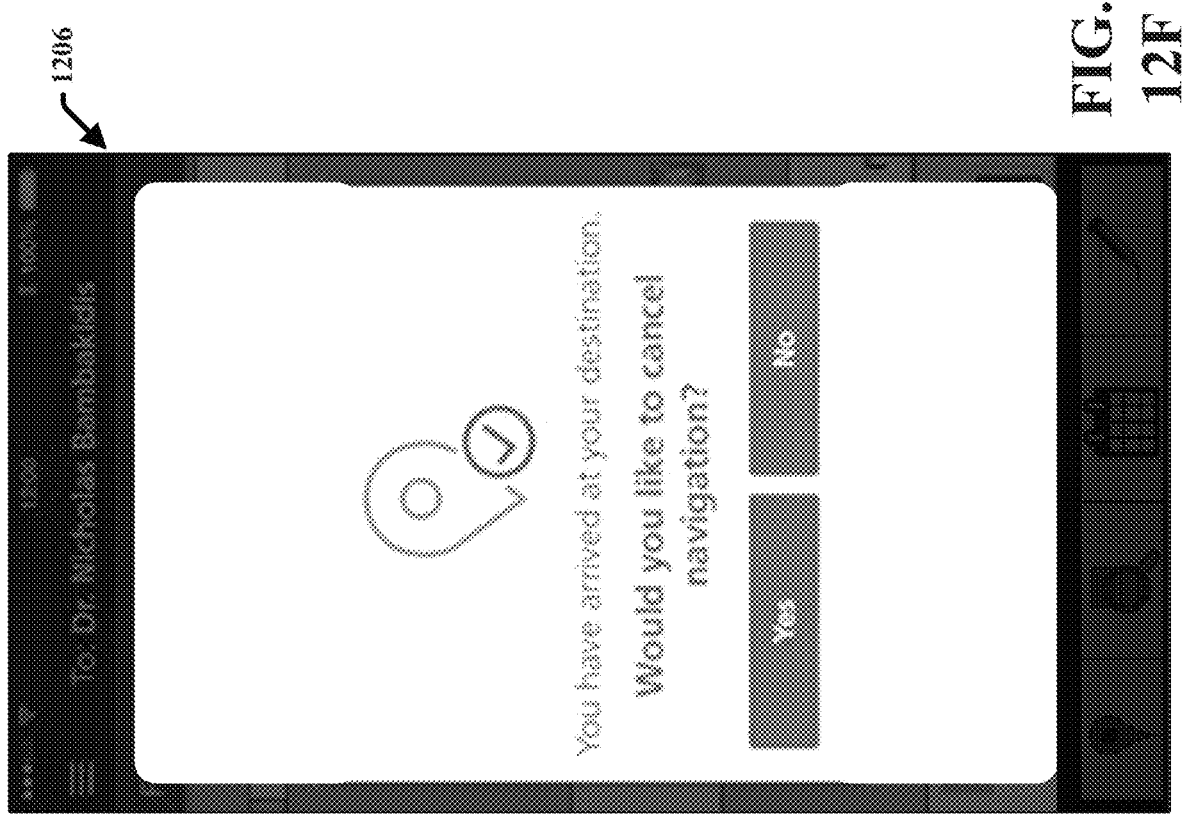
Figure 12E:
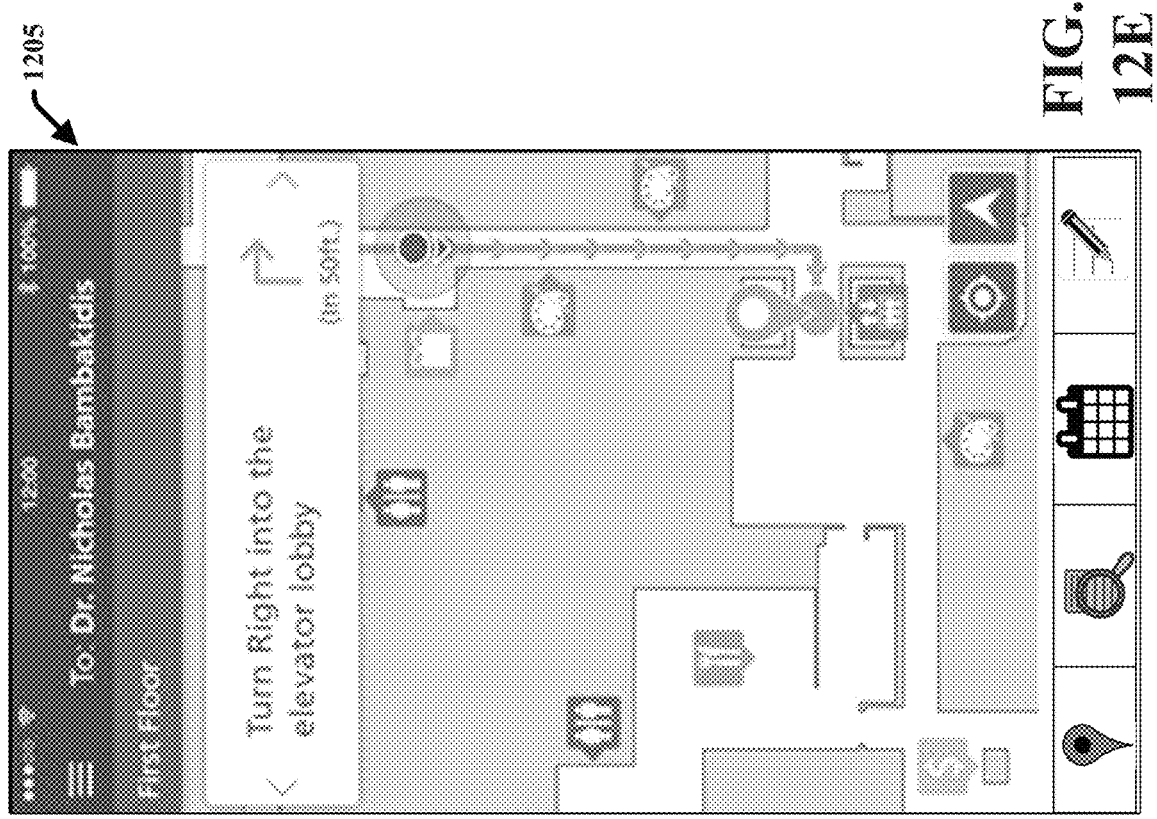

FIG. 12E presents an example GUI 1205 demonstrating example navigation instructions that can be presented to the user in association with providing real-time navigation to the destination location. In accordance with the example use case, the destination location is the patient's appointment scheduled at the Cancer Center, Boldwell building, 5$^{th}$ Floor. As shown in GUI 1205, the initial navigation instructions direct the user from the user's current first floor location to the nearest elevator lobby where the user can catch an elevator to the 5$^{th}$ floor. FIG. 12F presents an example GUI 1206 that can be presented once the user has reached their destination location.

Figure 13B:
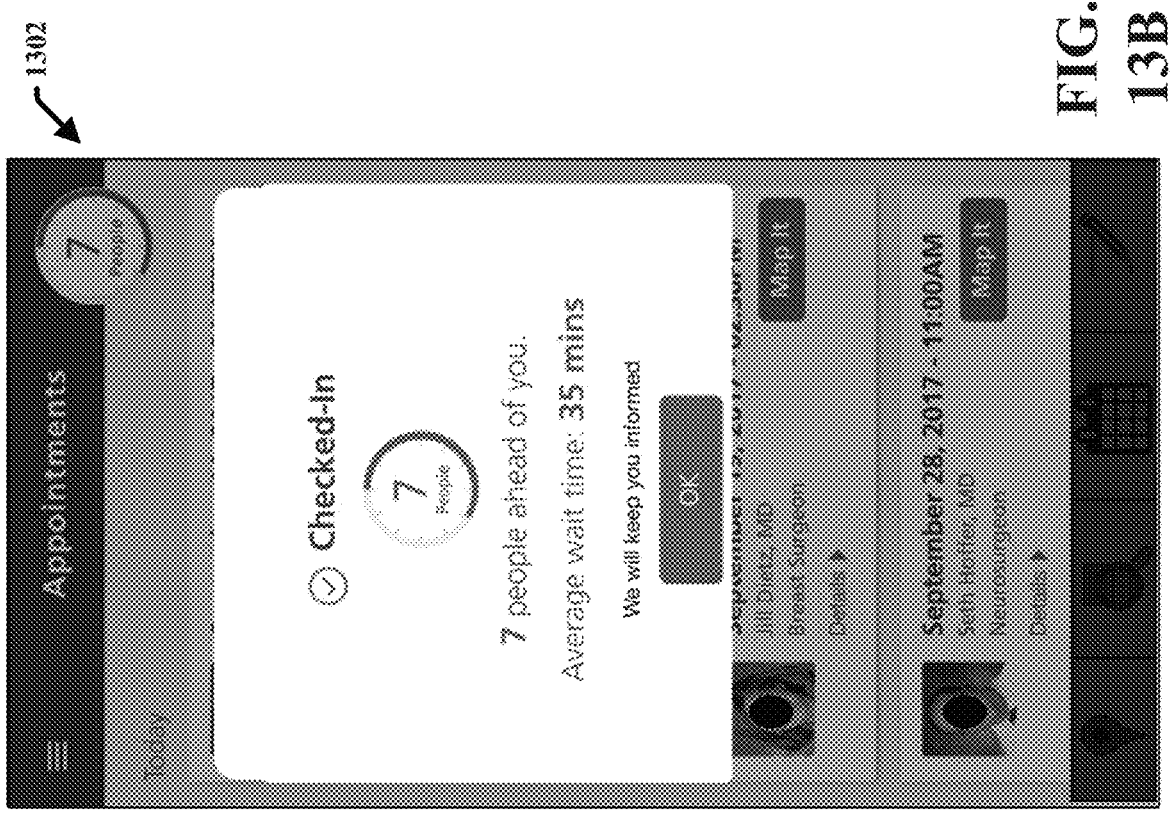
FIGS. 13A and 13B present example GUIs that can be generated and presented by the POEM application in association with checking into a medical appointment in accordance with aspects and embodiments disclosed herein.
Figure 13A:
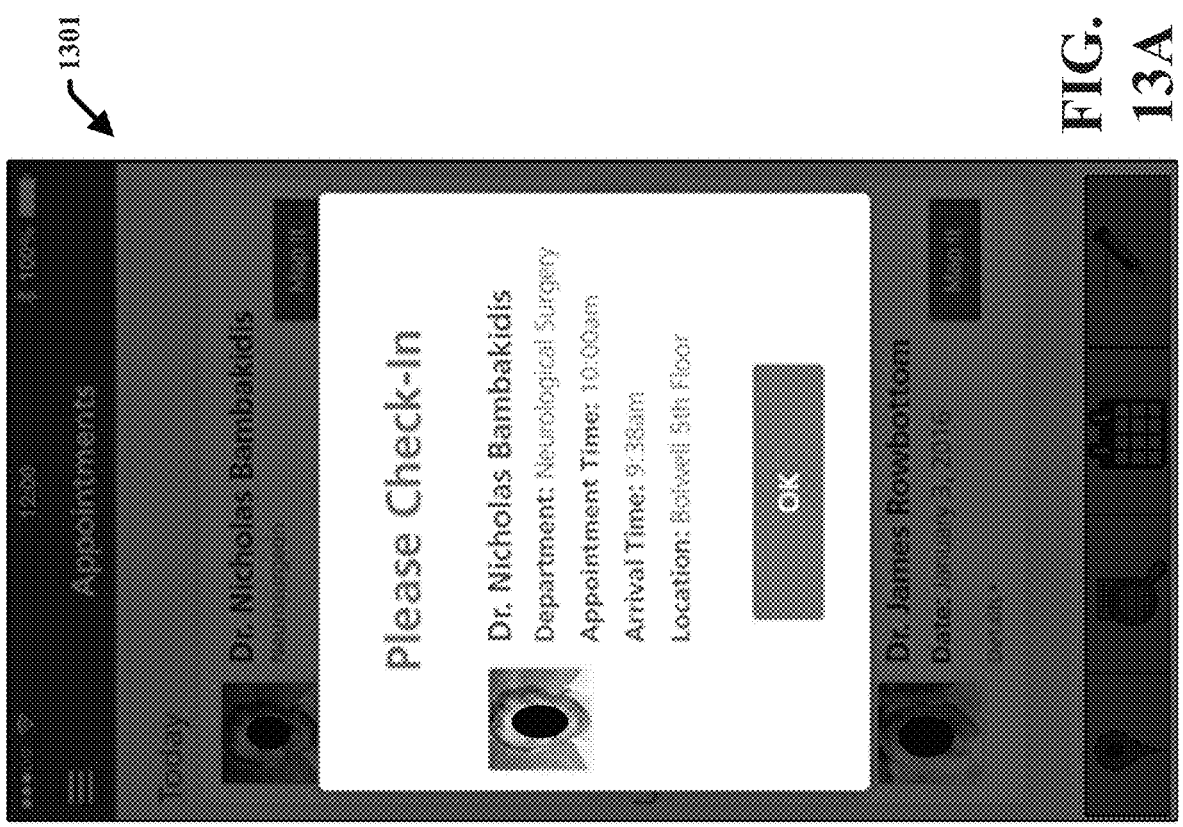

FIGS. 13A and 13B present example GUIs that can be generated and presented by the POEM application 122 in association with checking into a medical appointment. FIG. 13A depicts an example GUI 1301 including a prompt asking the user to check into an upcoming appointment. In some implementations, the POEM application 122 can be configured to generate GUI 1301 in response to arrival of the patient at the appointment location. For example, as shown in GUI 1301, the arrival time is indicated as 9:38 am. In this example, selection of the "OK" icon from GUI 1301 can result in checking the user into the appointment.

FIG. 13B depicts an example GUI 1302 that can be generated and presented to a user in response to check-in (e.g., in response to selection of the "OK" icon in GUI 1301). As shown in GUI 1302, after a user checks into an appointment, the user can be presented with a prompt confirming the user is checked-in. The prompt can also identify the estimated wait time (e.g., as determined by the waiting time management component 306) which in this case is 35 minutes. The prompt can also identify the number of patients in the queue that are ahead of the patient which in this case is currently 7.

Figure 14B:
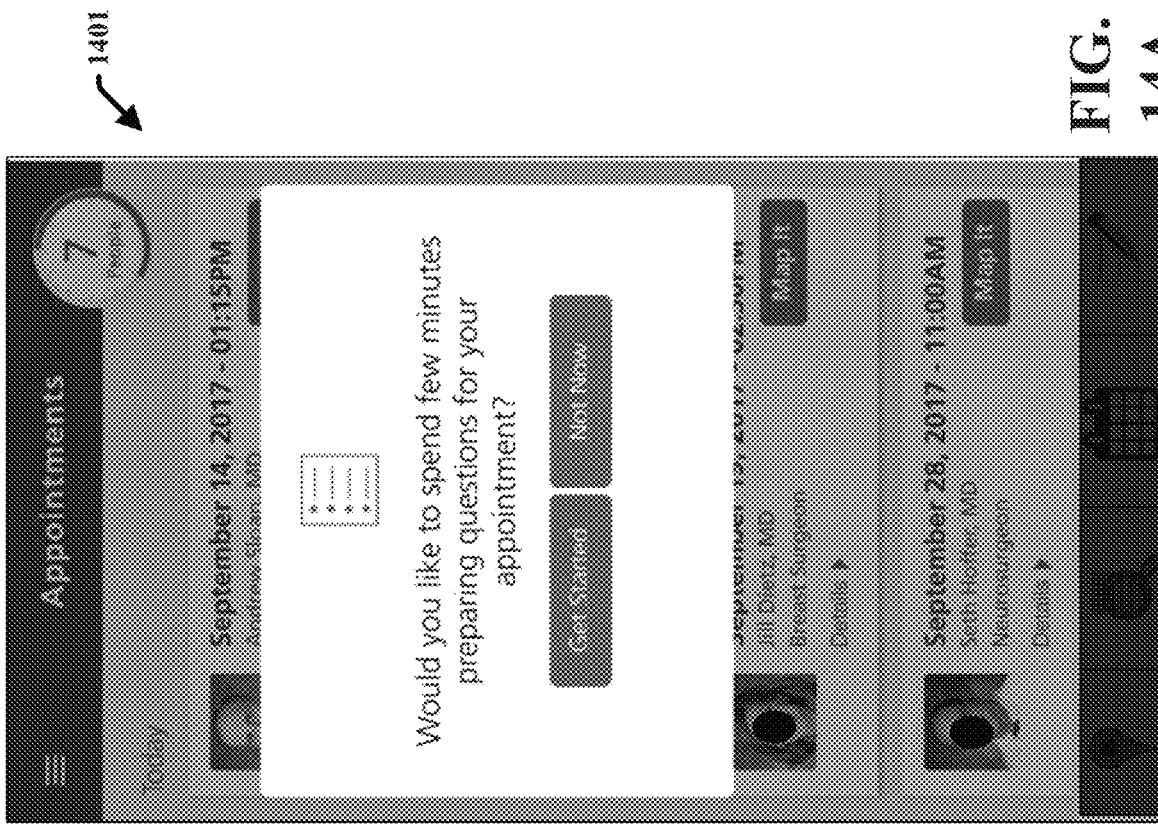
Figure 14A:
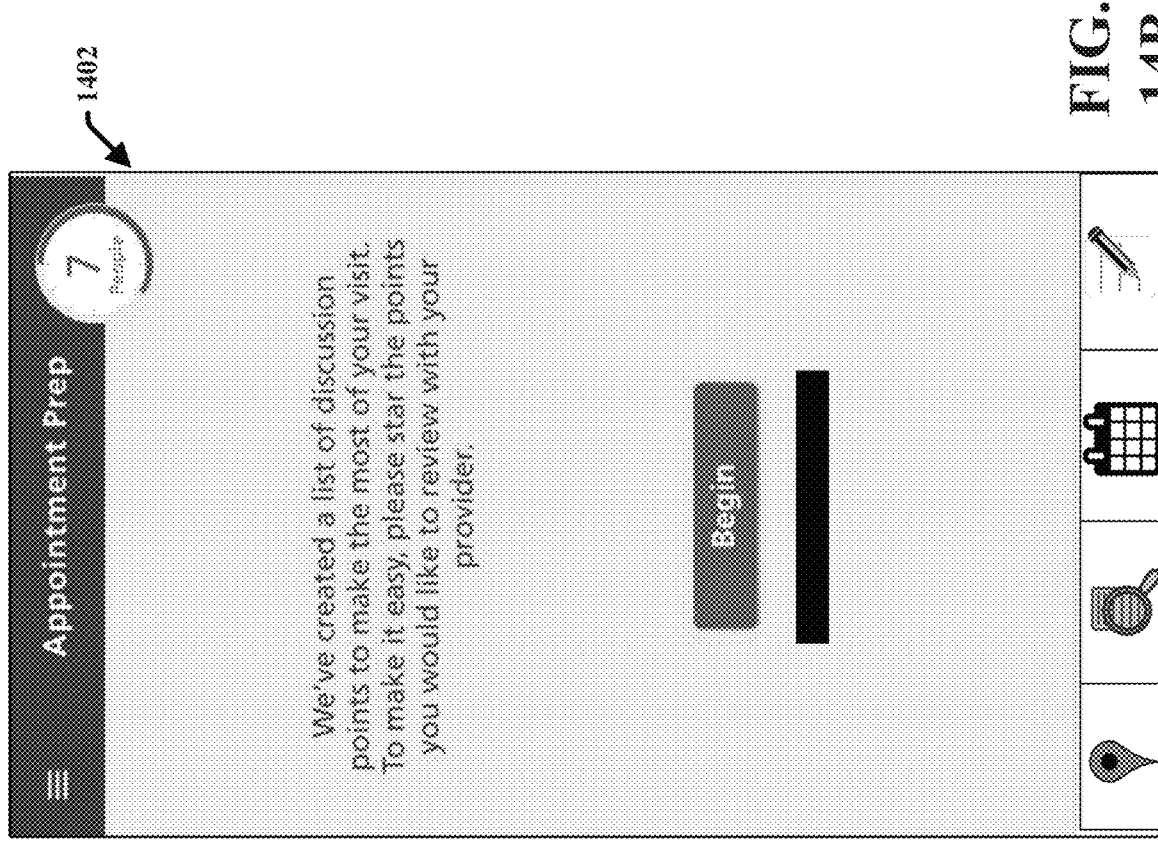
Figures 14C, 14D:
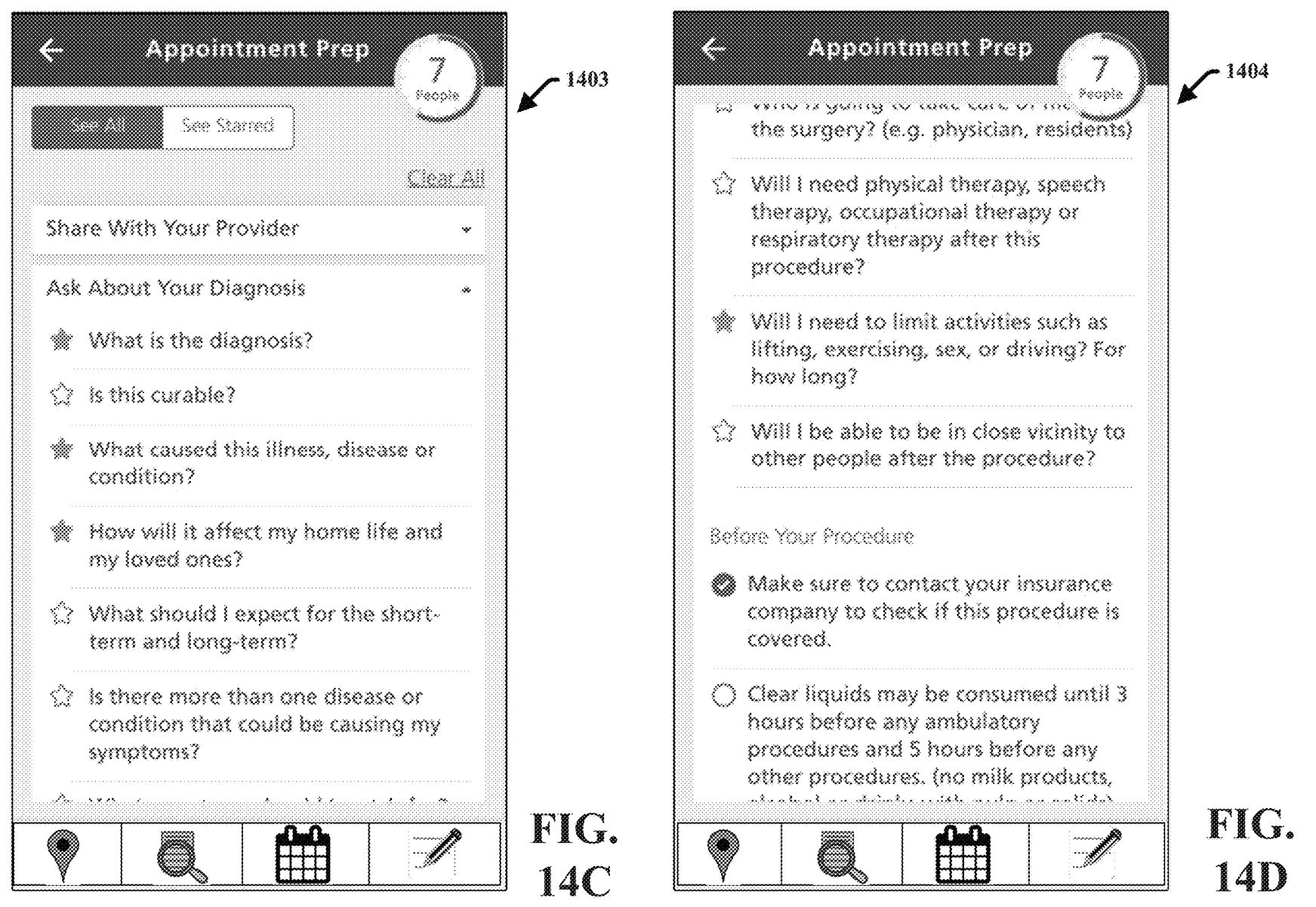

FIGS. 14A-14D present example GUIs that can be generated and presented by the POEM application 122 to facilitate preparing a user for an upcoming appointment (e.g., as facilitated by the preparation component 304). For example, FIG. 14A presents an example GUI 1401 asking the user if the user would like to prepare questions for the appointment. In some implementations, the POEM application 122 can be configured to generate and present GUI 1401 based on the user checking into the appointment. In other embodiments, the POEM application 122 can be configured to generate and present GUI 1401 in response to selection of the appointment preparation function (e.g., function 708). FIG. 14B presents an example GUI 1402 that can be generated by the POEM application 122 in response to selection of the "get started" option from GUI 1402. GUI 1402 provides instructions for an example question preparation processes that can be provided by the POEM application (e.g., using the features and functionalities of the preparation component 304). FIGS. 14C and 14D present example question preparation forms that can be provided to the user to facilitate preparing questions for the appointment in response to selection of the "begin" icon from GUI 1402. As shown in GUIs 1403 and 1404, the user can star or otherwise select questions that the user would like to ask the provider in during the appointment. Once the user has completed the question preparation form, in some implementations, the user can submit the starred questions to the clinician using the POEM application. In other implementations, the starred questions can be stored and retrieved later during the appointment by the user as need to remind the user regarding the questions the user wanted to ask the clinician.

Figure 15B:
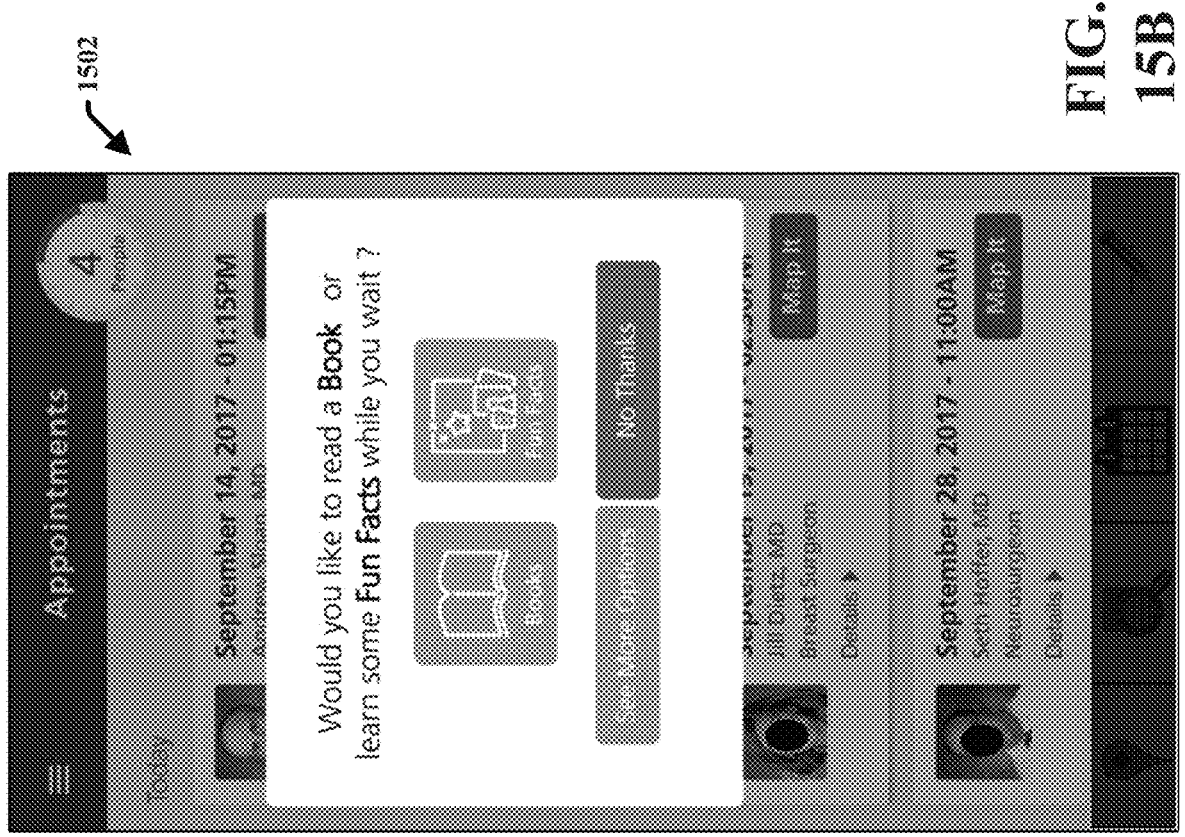
FIGS. 15A and 15B present example GUIs that can be generated and presented by the POEM application to facilitate optimizing a waiting period prior to initiation of an appointment in accordance with aspects and embodiments disclosed herein.
Figure 15A:
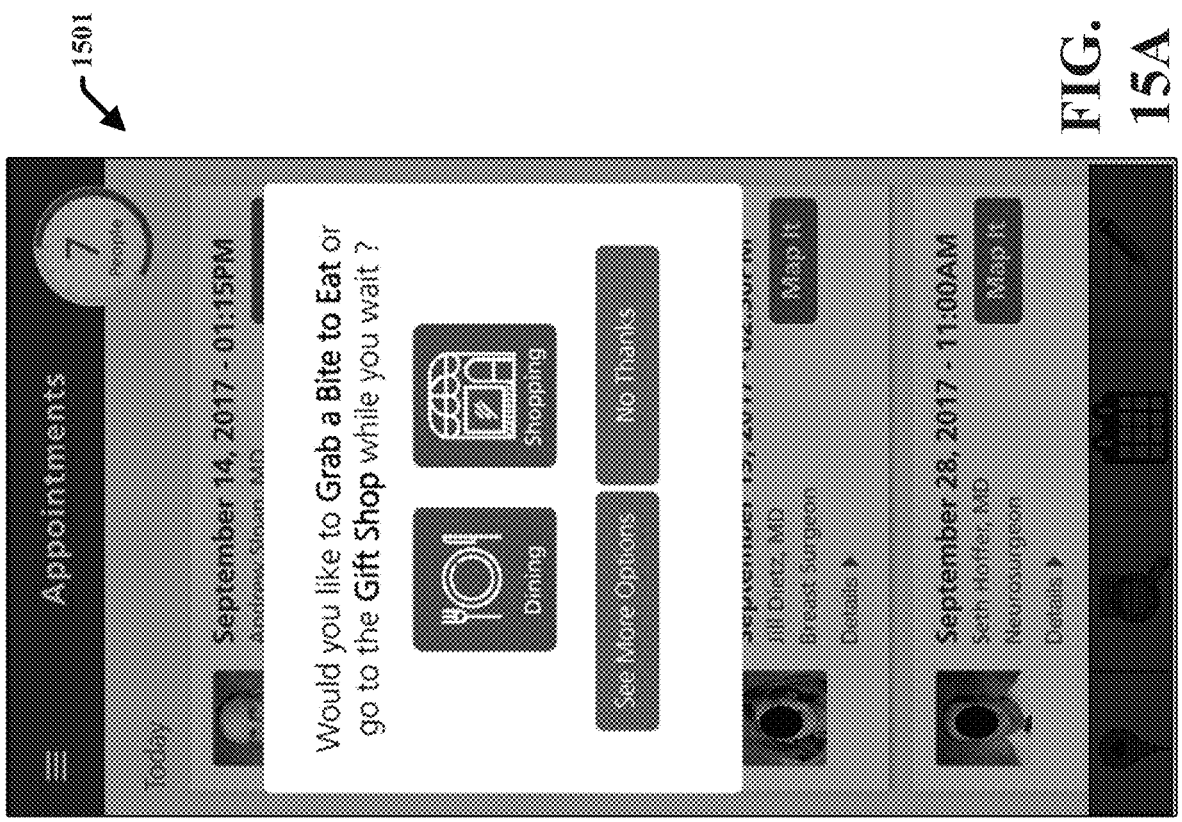

FIGS. 15A and 15B present example GUIs that can be generated and presented by the POEM application 122 to facilitate optimizing a waiting time period prior to initiation of an appointment. In particular, FIGS. 15A and 15B demonstrate some example general prompts that can be provided by the waiting time management component 306 providing suggested things for the user to do while waiting for the appointment to begin. For example, FIG. 15A presents an example GUI 1501 with a prompt asking the user if the user would like to grab a bite to eat or go to the gift shop. The prompt includes corresponding widgets which upon selection can facilitate finding a specific point of interests (e.g., a particular restaurant or store) and receiving navigation information to the respective points of interest. FIG. 15B presents an example GUI 1502 with a prompt asking the user if the user would like to read a book or learn some fun facts during the waiting period. Selection of the corresponding widgets can result in the provision of book choices and fun facts categories, respectively. Although the example prompts shown in FIGS. 15A and 15B are relatively general in nature, as described with reference to FIG. 3 and the waiting time management component 306, in various embodiments, the specific prompts and recommendations provided by the waiting time management component 306 can be based on the duration of the waiting period, other potential contextual factors, and one or more personalized factors associated with the user.

Figure 16B:
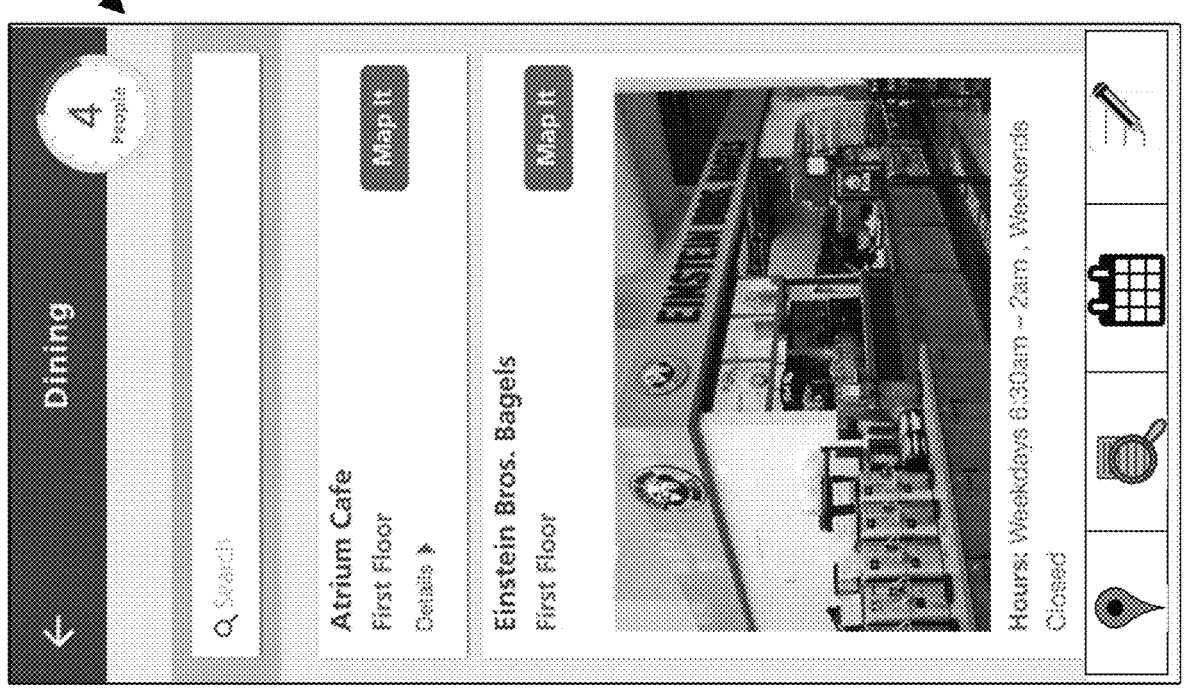
FIGS. 16A and 16B present some example GUIs that can be generated and presented by the POEM application in association with usage of the explore functionality in accordance with aspects and embodiments disclosed herein.
Figure 16A:
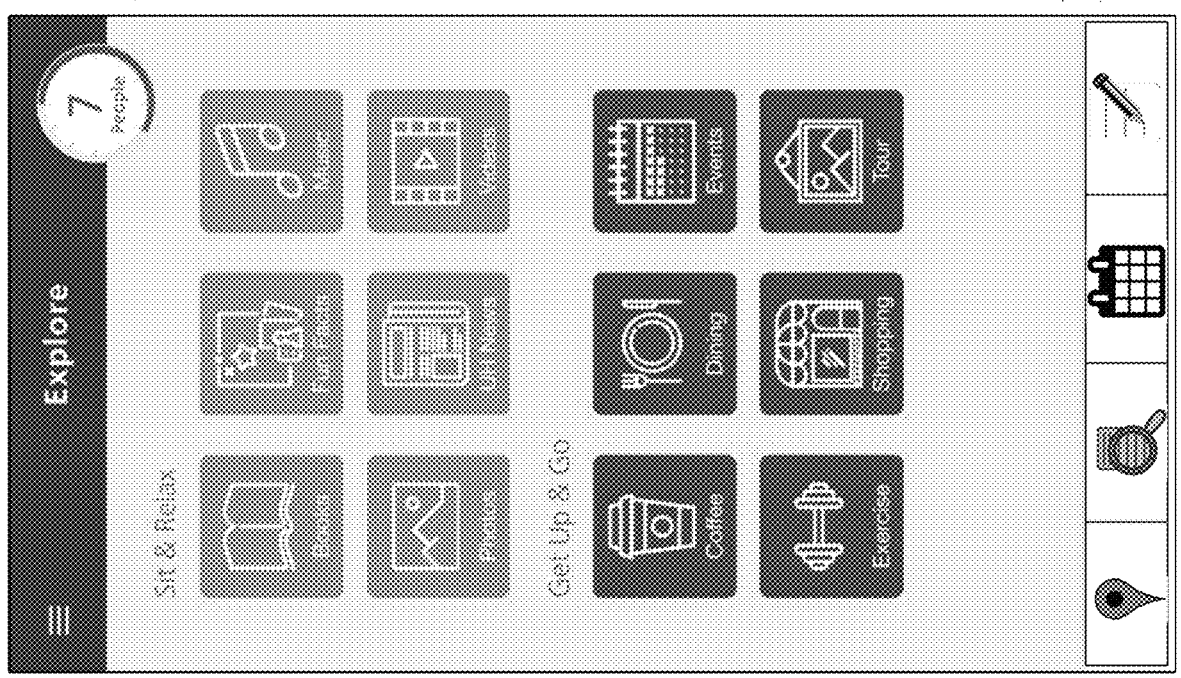

FIGS. 16A and 16B present some example GUIs that can be generated and presented by the POEM application 122 in association with usage of the explore functionality. In one or more embodiments, FIG. 16A presents an example menu GUI 1601 providing various interactive or selectable options provided by the explore functionality of the POEM application 122. Selection of the corresponding icons can result in provision of media (e.g., books, fun facts, music, photos, news, and videos), information and associated navigation functionality in implementations in which the icon is associated with point of interest. In one example implementation, the POEM application 122 can be configured to generate GUI 1601 in response to the explore functionality (e.g., using the explore function 704 from of GUI 700). FIG. 16B presents an example GUI 1601 including some dining options that can be presented in response to selection of the dining icon from GUI 1602. In this example, the details of the Einstein Bros. Bagels are expanded (e.g., in response to user input/selection) and provide information about the restaurant. Selection of the "map it" icon associated with a dining option can result in the provision of navigation information to the selected dining option, including real-time navigation information.

Figure 17B:
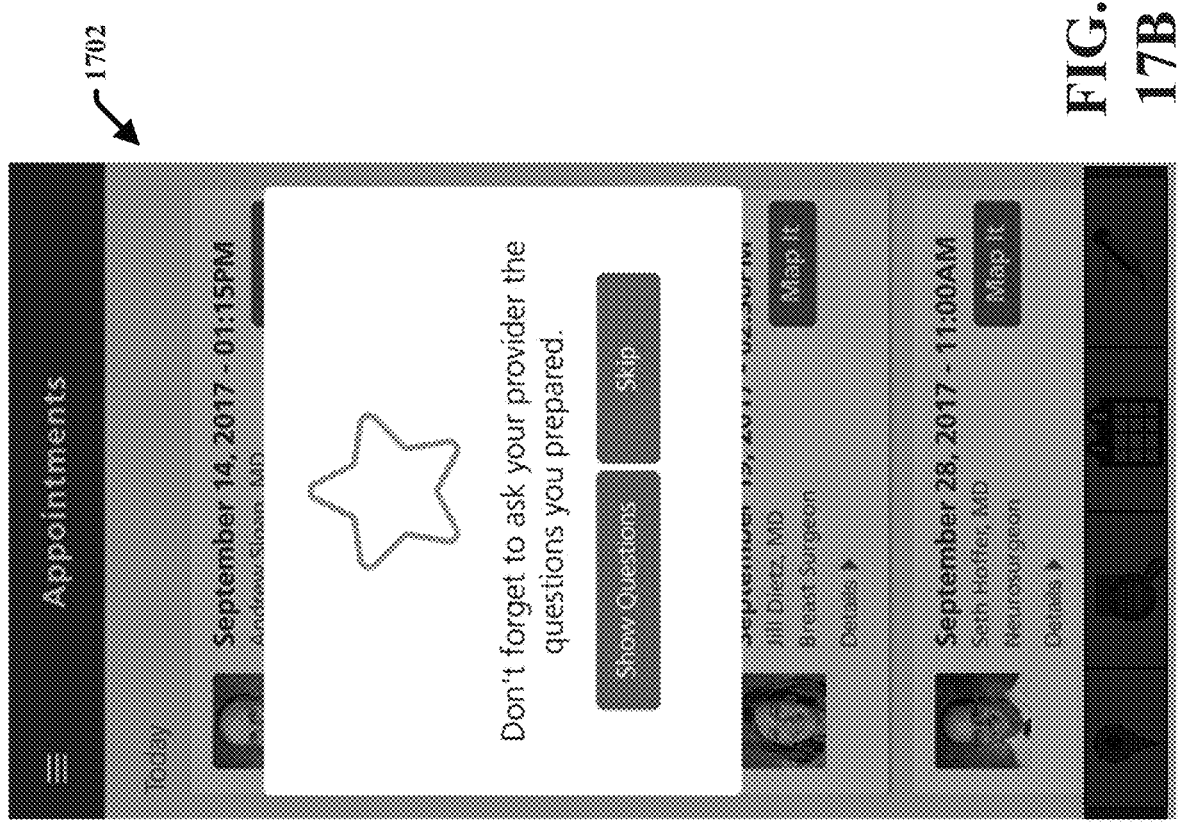
FIGS. 17A and 17B present example GUIs associated with the appointment functionality of the POEM application in accordance with aspects and embodiments disclosed herein.
Figure 17A:
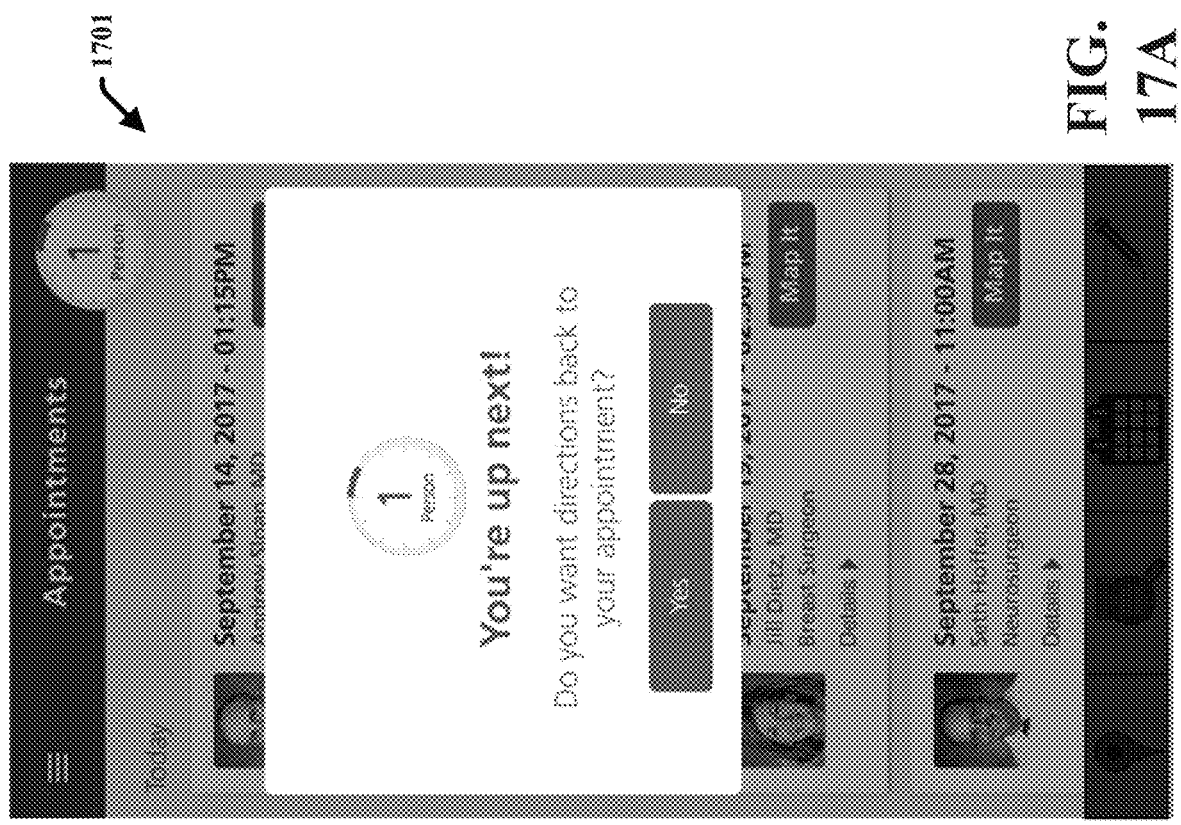

FIGS. 17A and 17B present example GUIs associated with the appointment functionality of the POEM application 122. For example, FIG. 17A presents an example GUI 1701 that can be generated and presented to the user (e.g., via the appointment notification component 308) when the user's appointment is about to begin. FIG. 17B presents an example GUI 1702 with another notification prompt that can be generated and presented to the user (e.g., by the preparation component 304) in association with initiation of the medical appointment if the user previously prepared questions to ask the provider during the appointment.

Figure 18B:
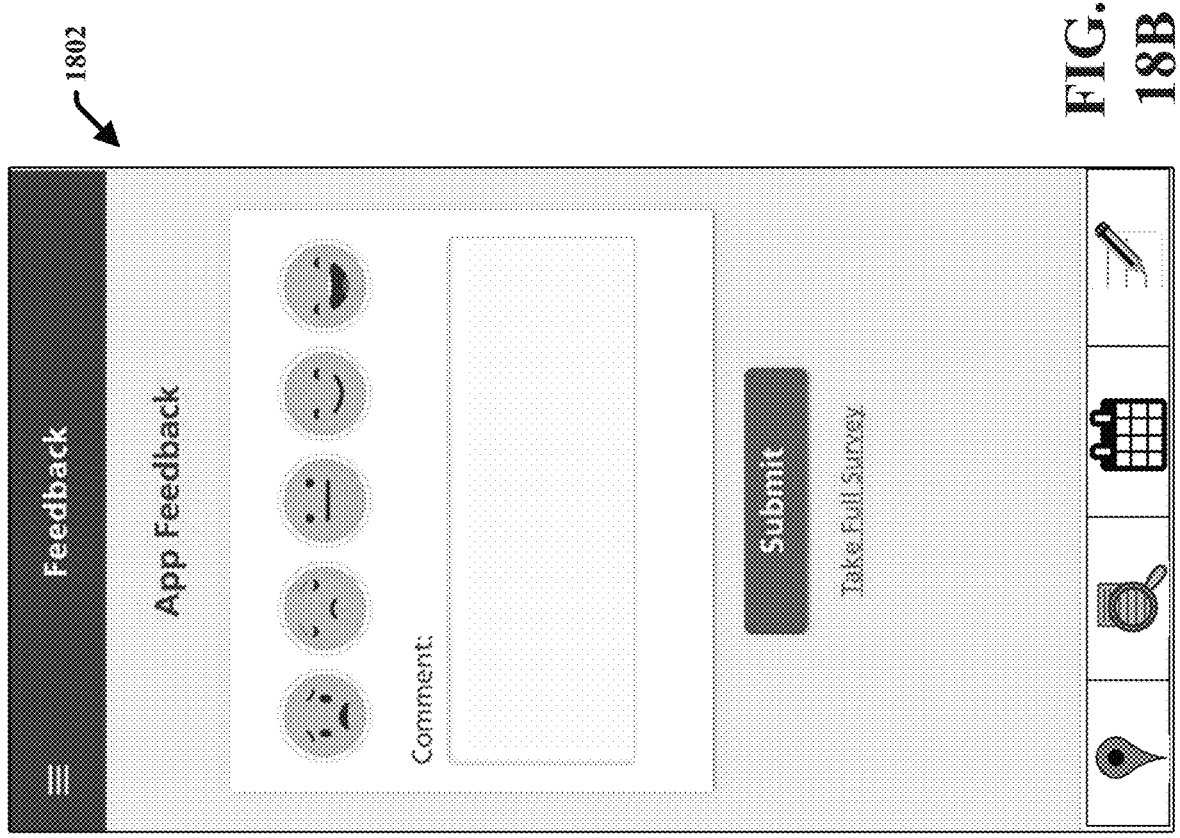
FIGS. 18A and 18B present example GUIs that can be generated and presented by the POEM application in association with completion of medical appointment and leaving of the medical facility in accordance with aspects and embodiments disclosed herein.
Figure 18A:
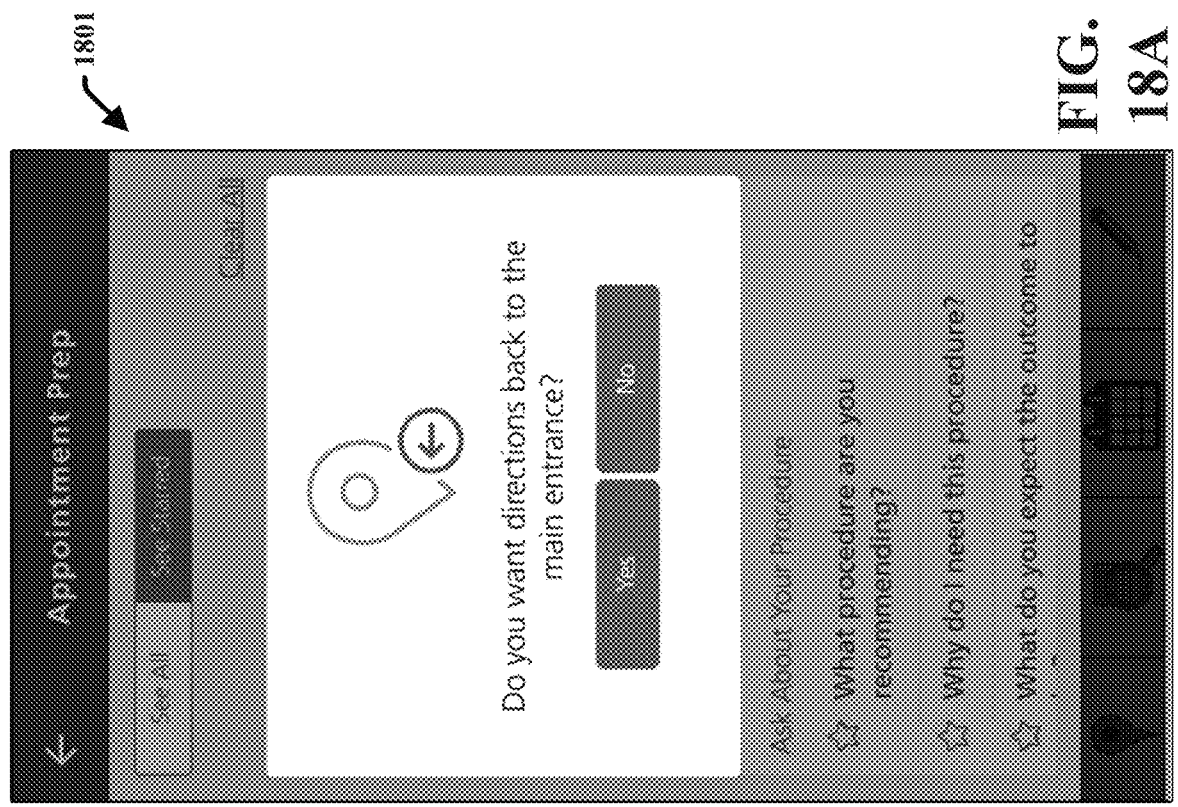

FIGS. 18A and 18B present example GUIs that can be generated and presented by the POEM application in association with completion of medical appointment and leaving of the medical facility. For example, FIG. 18A depicts an example GUI 1801 including a prompt asking the user if the user would like directions back to the main entrance. In one implementation, the wayfinding component 142 can be configured to provide such a prompt in response to checking out of an appointment. FIG. 18B presents an example GUI 1802 including a survey that can be presented to the user to gain feedback regarding the user's experience at the healthcare facility using the POEM application 122. In one implementation, GUI 1802 can be generated and presented to the user in association with closing the application or leaving of the healthcare facility.

FIG. 19 presents an example GUI 1900 associated with an appointment scheduling system, such as appointment scheduling system 116. GUI 1900 demonstrates some example information that can be tracked by the appointment scheduling system 116. For example, in the embodiment shown, the appointment scheduling system 116 can track information regarding appointment times for patients scheduled with different physicians, the current patient, the number of checked in patients in the queue, and average appointment duration for the current patient, and the status of the current patient (e.g., check in, in exam room, or checked-out). In one or more embodiments, GUI 1900 can be generated and presented to administrative personnel to facilitate managing and tracking appointment scheduling. The GUI can include interactive features that allows an administrator to change the status of the patient, delete an appointment, edit an appointment, add a new appointment and the like. With this implementation, the scheduling information can be manually controlled based on user input. However, in other implementation, the scheduling information can be automatically generated and updated using the feature and functionalities described with respect to the check-in component 302.

Figure 20:
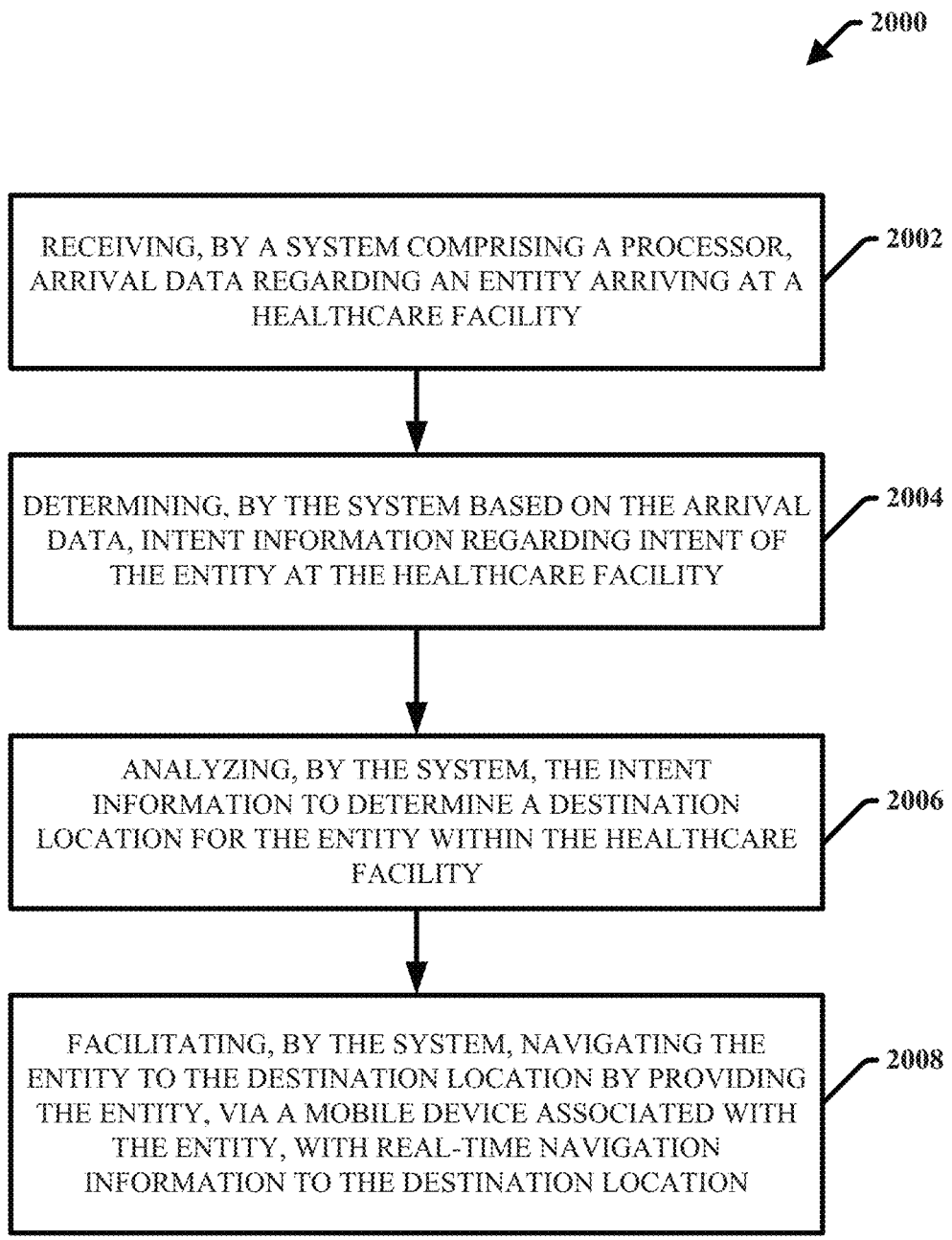
FIG. 20 illustrates an example method that facilitates managing and optimizing the experience of patients and visitors in association with visiting a healthcare facility in accordance with various aspects and embodiments described herein.
Figure 21:
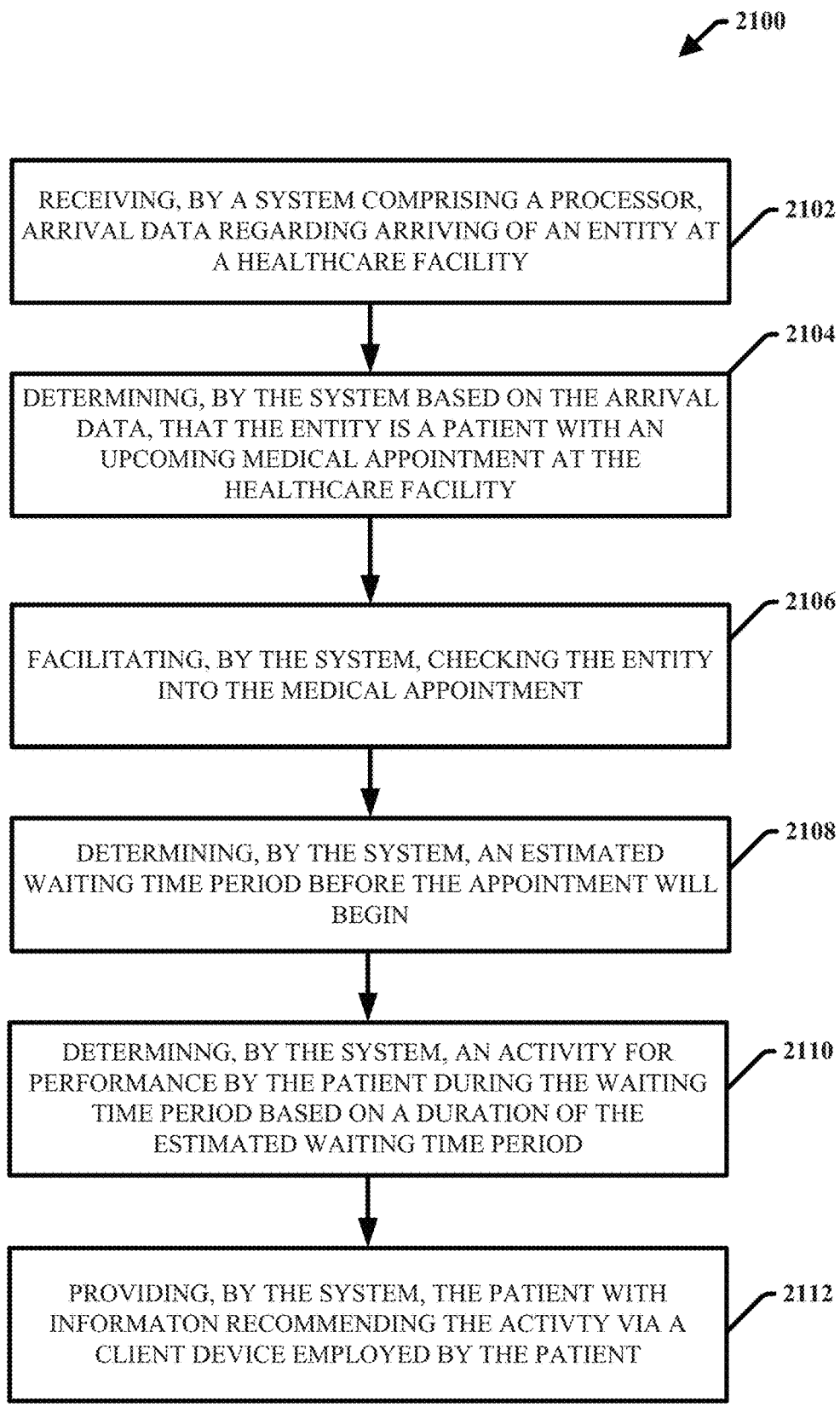
FIG. 21 illustrates another example method that facilitates managing and optimizing the experience of patients and visitors in association with visiting a healthcare facility in accordance with various aspects and embodiments described herein.

In view of the example system(s) described above, example method(s) that can be implemented in accordance with the disclosed subject matter can be better appreciated with reference to flowcharts in FIGS. 20-21. For purposes of simplicity of explanation, example methods disclosed herein are presented and described as a series of acts; however, it is to be understood and appreciated that the claimed subject matter is not limited by the order of acts, as some acts may occur in different orders and/or concurrently with other acts from that shown and described herein. For example, one or more example methods disclosed herein could alternatively be represented as a series of interrelated states or events, such as in a state diagram. Moreover, interaction diagram(s) may represent methods in accordance with the disclosed subject matter when disparate entities enact disparate portions of the methods. Furthermore, not all illustrated acts may be required to implement a described example method in accordance with the subject specification. Further yet, two or more of the disclosed example methods can be implemented in combination with each other, to accomplish one or more aspects herein described. It should be further appreciated that the example methods disclosed throughout the subject specification are capable of being stored on an article of manufacture (e.g., a computer-readable medium) to allow transporting and transferring such methods to computers for execution, and thus implementation, by a processor or for storage in a memory.

FIG. 20 illustrates an example method 2000 that facilitates managing and optimizing the experience of patients and visitors in association with visiting a healthcare facility in accordance with various aspects and embodiments described herein. Repetitive description of like elements employed in respective embodiments is omitted for sake of brevity.

At 2002, a system comprising a processor (e.g., system 100), receives arrival data regarding an entity arriving at a healthcare facility (e.g., via the receiving component 136). For example, the arrival data can be based on the detection of the location of the entity at the healthcare facility. In another example, the arrival data can be based on login or activation of the POEM application 122. At 2004, the system determines, based on the arrival data, intent information regarding intent of the entity at the healthcare facility (e.g., via the discovery component 138). At 2006, the system analyzes the intent information to determine a destination location for the entity within the healthcare facility (e.g., via the discovery component 138). At 2008, the system facilitates navigating the entity to the destination location by providing the entity, via a mobile device associated with the entity (e.g., client device 120), with real-time navigation information to the destination location (e.g., via the wayfinding component 142).

FIG. 21 illustrates another example method 2100 that facilitates managing and optimizing the experience of patients and visitors in association with visiting a healthcare facility in accordance with various aspects and embodiments described herein. Repetitive description of like elements employed in respective embodiments is omitted for sake of brevity.

At 2102, a system comprising a processor (e.g., system 100), receives arrival data regarding an entity arriving at a healthcare facility (e.g., via the receiving component 136). At 2104, the system determines, based on the arrival data, that the entity is a patient with an upcoming appointment at the healthcare facility (e.g., via discovery component 138 and/or appointment component 140). At 2106, the system facilitates checking the patient into the medical appointment (e.g., via the check-in component 302). At 2108, the system determines an estimated waiting time period before the appointment will begin (e.g., via the waiting time management component 306). At 2110, the system determines an activity for performance by the patient during the waiting time period based on a duration of the estimated waiting time period (e.g., via the waiting time management component 306). At 2112, the system provides the patient with information recommending the activity via a client device (e.g., client device 120) employed by the patient.

Example Operating Environments

The systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which may be explicitly illustrated in this disclosure.

Figure 22:
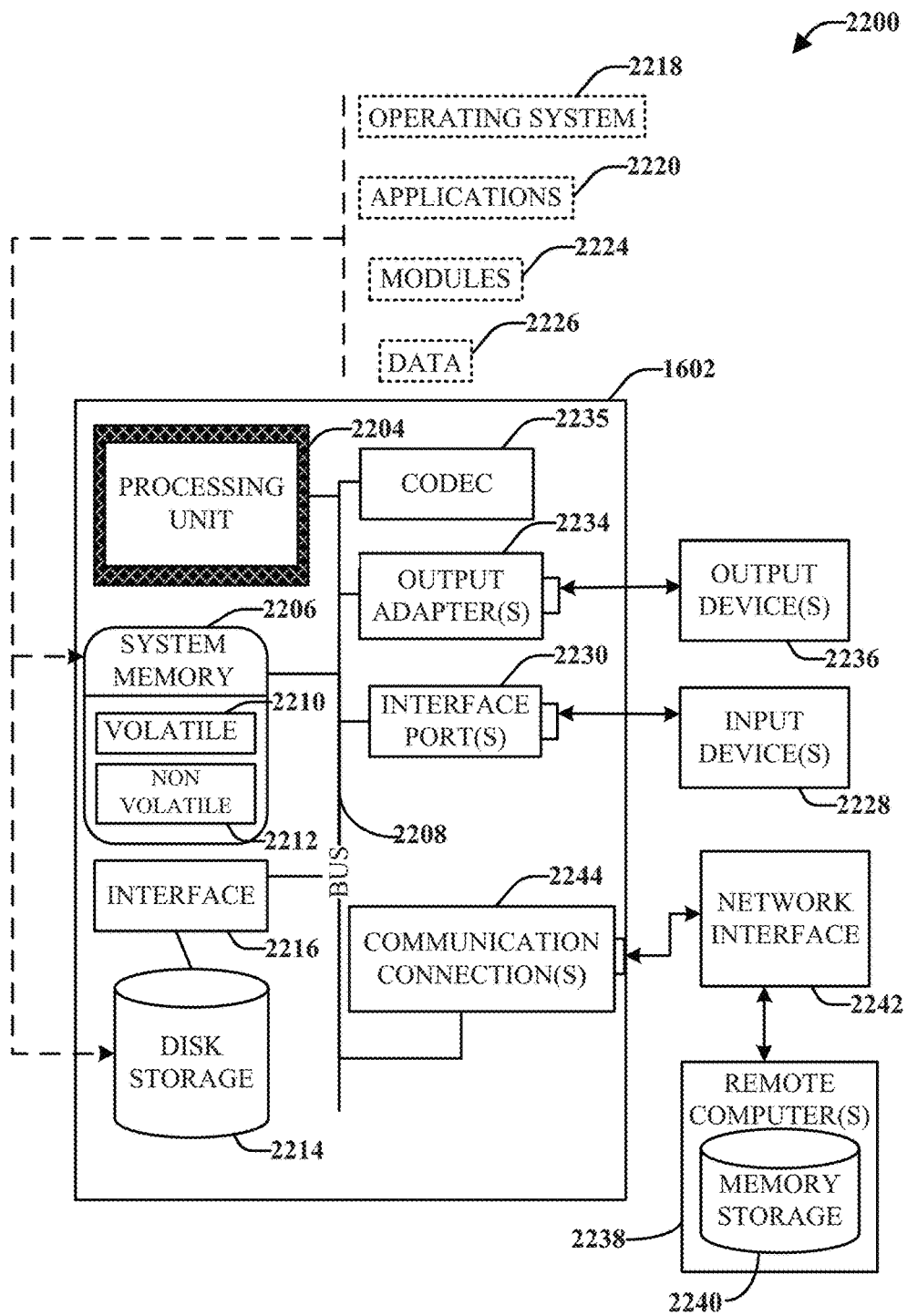
FIG. 22 is a schematic block diagram illustrating a suitable operating environment in accordance with various aspects and embodiments.

With reference to FIG. 22, a suitable environment 2200 for implementing various aspects of the claimed subject matter includes a computer 2202. The computer 2202 includes a processing unit 2204, a system memory 2206, a codec 2205, and a system bus 2208. The system bus 2208 couples system components including, but not limited to, the system memory 2206 to the processing unit 2204. The processing unit 2204 can be any of various available suitable processors. Dual microprocessors and other multiprocessor architectures also can be employed as the processing unit 2204.

The system bus 2208 can be any of several types of suitable bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 22104), and Small Computer Systems Interface (SCSI).

The system memory 2206 includes volatile memory 2210 and non-volatile memory 2212. The basic input/output system (BIOS), containing the basic routines to transfer information between elements within the computer 2202, such as during start-up, is stored in non-volatile memory 2212. In addition, according to present innovations, codec 2205 may include at least one of an encoder or decoder, wherein the at least one of an encoder or decoder may consist of hardware, a combination of hardware and software, or software. Although, codec 2205 is depicted as a separate component, codec 2205 may be contained within non-volatile memory 2212. By way of illustration, and not limitation, non-volatile memory 2212 can include read only memory (ROM), programmable ROM (PROM), electrically programmable ROM (EPROM), electrically erasable programmable ROM (EEPROM), or flash memory. Volatile memory 2210 includes random access memory (RAM), which acts as external cache memory. According to present aspects, the volatile memory may store the write operation retry logic (not shown in FIG. 22) and the like. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM).

Computer 2202 may also include removable/non-removable, volatile/non-volatile computer storage medium. FIG. 22 illustrates, for example, disk storage 2214. Disk storage 2214 includes, but is not limited to, devices like a magnetic disk drive, solid state disk (SSD) floppy disk drive, tape drive, Jaz drive, Zip drive, LS-70 drive, flash memory card, or memory stick. In addition, disk storage 2214 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 2214 to the system bus 2208, a removable or non-removable interface is typically used, such as interface 2216.

It is to be appreciated that FIG. 22 describes software that acts as an intermediary between users and the basic computer resources described in the suitable operating environment 2200. Such software includes an operating system 2218. Operating system 2218, which can be stored on disk storage 2214, acts to control and allocate resources of the computer system 2202. Applications 2220 take advantage of the management of resources by operating system 2218 through program modules 2224, and program data 2226, such as the boot/shutdown transaction table and the like, stored either in system memory 2206 or on disk storage 2214. It is to be appreciated that the claimed subject matter can be implemented with various operating systems or combinations of operating systems.

A user enters commands or information into the computer 2202 through input device(s) 2228. Input devices 2228 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 2204 through the system bus 2208 via interface port(s) 2230. Interface port(s) 2230 include, for example, a serial port, a parallel port, a game port, and a universal serial bus (USB). Output device(s) 2236 use some of the same type of ports as input device(s). Thus, for example, a USB port may be used to provide input to computer 2202, and to output information from computer 2202 to an output device 2236. Output adapter 2234 is provided to illustrate that there are some output devices 2236 like monitors, speakers, and printers, among other output devices 2236, which require special adapters. The output adapters 2234 include, by way of illustration and not limitation, video and sound cards that provide a means of connection between the output device 2236 and the system bus 2208. It should be noted that other devices and/or systems of devices provide both input and output capabilities such as remote computer(s) 2238.

Computer 2202 can operate in a networked environment using logical connections to one or more remote computers, such as remote computer(s) 2238. The remote computer(s) 2238 can be a personal computer, a server, a router, a network PC, a workstation, a microprocessor based appliance, a peer device, a smart phone, a tablet, or other network node, and typically includes many of the elements described relative to computer 2202. For purposes of brevity, only a memory storage device 2240 is illustrated with remote computer(s) 2238. Remote computer(s) 2238 is logically connected to computer 2202 through a network interface 2242 and then connected via communication connection(s) 2244. Network interface 2242 encompasses wire and/or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 2244 refers to the hardware/software employed to connect the network interface 2242 to the bus 2208. While communication connection 2244 is shown for illustrative clarity inside computer 2202, it can also be external to computer 2202. The hardware/software necessary for connection to the network interface 2242 includes, for exemplary purposes only, internal and external technologies such as, modems including regular telephone grade modems, cable modems and DSL modems, ISDN adapters, and wired and wireless Ethernet cards, hubs, and routers.

Figure 23:
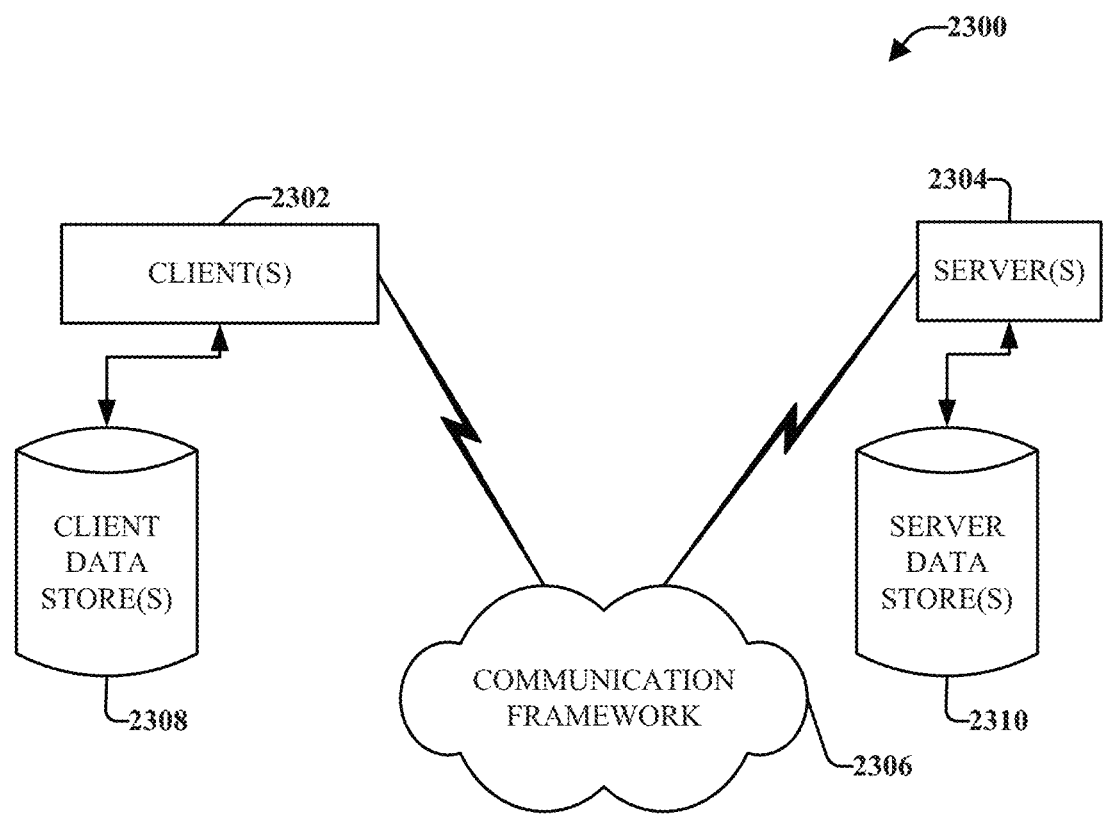
FIG. 23 is a schematic block diagram of a sample-computing environment in accordance with various aspects and embodiments.

Referring now to FIG. 23, there is illustrated a schematic block diagram of a computing environment 2360 in accordance with this disclosure. The system 2360 includes one or more client(s) 2362 (e.g., laptops, smart phones, PDAs, media players, computers, portable electronic devices, tablets, and the like). The client(s) 2362 can be hardware and/or software (e.g., threads, processes, computing devices). The system 2360 also includes one or more server(s) 2364. The server(s) 2364 can also be hardware or hardware in combination with software (e.g., threads, processes, computing devices). The servers 2364 can house threads to perform transformations by employing aspects of this disclosure, for example. One possible communication between a client 2362 and a server 2364 can be in the form of a data packet transmitted between two or more computer processes wherein the data packet may include video data. The data packet can include a metadata, e.g., associated contextual information, for example. The system 2360 includes a communication framework 2366 (e.g., a global communication network such as the Internet, or mobile network(s)) that can be employed to facilitate communications between the client(s) 2362 and the server(s) 2364.

Communications can be facilitated via a wired (including optical fiber) and/or wireless technology. The client(s) 2362 include or are operatively connected to one or more client data store(s) 2368 that can be employed to store information local to the client(s) 2362 (e.g., associated contextual information). Similarly, the server(s) 2364 are operatively include or are operatively connected to one or more server data store(s) 2316 that can be employed to store information local to the servers 2364.

In one embodiment, a client 2362 can transfer an encoded file, in accordance with the disclosed subject matter, to server 2364. Server 2364 can store the file, decode the file, or transmit the file to another client 2362. It is to be appreciated, that a client 2362 can also transfer uncompressed file to a server 2364 and server 2364 can compress the file in accordance with the disclosed subject matter. Likewise, server 2364 can encode video information and transmit the information via communication framework 2366 to one or more clients 2362.

The illustrated aspects of the disclosure may also be practiced in distributed computing environments where certain tasks are performed by remote processing devices that are linked through a communications network. In a distributed computing environment, program modules can be located in both local and remote memory storage devices.

Moreover, it is to be appreciated that various components described in this description can include electrical circuit(s) that can include components and circuitry elements of suitable value in order to implement the embodiments of the subject innovation(s). Furthermore, it can be appreciated that many of the various components can be implemented on one or more integrated circuit (IC) chips. For example, in one embodiment, a set of components can be implemented in a single IC chip. In other embodiments, one or more of respective components are fabricated or implemented on separate IC chips.

What has been described above includes examples of the embodiments of the present invention. It is, of course, not possible to describe every conceivable combination of components or methodologies for purposes of describing the claimed subject matter, but it is to be appreciated that many further combinations and permutations of the subject innovation are possible. Accordingly, the claimed subject matter is intended to embrace all such alterations, modifications, and variations that fall within the spirit and scope of the appended claims. Moreover, the above description of illustrated embodiments of the subject disclosure, including what is described in the Abstract, is not intended to be exhaustive or to limit the disclosed embodiments to the precise forms disclosed. While specific embodiments and examples are described in this disclosure for illustrative purposes, various modifications are possible that are considered within the scope of such embodiments and examples, as those skilled in the relevant art can recognize.

In particular and in regard to the various functions performed by the above described components, devices, circuits, systems and the like, the terms used to describe such components are intended to correspond, unless otherwise indicated, to any component which performs the specified function of the described component (e.g., a functional equivalent), even though not structurally equivalent to the disclosed structure, which performs the function in the disclosure illustrated exemplary aspects of the claimed subject matter. In this regard, it will also be recognized that the innovation includes a system as well as a computer-readable storage medium having computer-executable instructions for performing the acts and/or events of the various methods of the claimed subject matter.

The aforementioned systems/circuits/modules have been described with respect to interaction between several components/blocks. It can be appreciated that such systems/circuits and components/blocks can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components, and any one or more middle layers, such as a management layer, may be provided to communicatively couple to such sub-components in order to provide integrated functionality. Any components described in this disclosure may also interact with one or more other components not specifically described in this disclosure but known by those of skill in the art.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

As used in this application, the terms "component," "module," "system," or the like are generally intended to refer to a computer-related entity, either hardware (e.g., a circuit), a combination of hardware and software, software, or an entity related to an operational machine with one or more specific functionalities. For example, a component may be, but is not limited to being, a process running on a processor (e.g., digital signal processor), a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers. Further, a "device" can come in the form of specially designed hardware; generalized hardware made specialized by the execution of software thereon that enables the hardware to perform specific function; software stored on a computer readable storage medium; software transmitted on a computer readable transmission medium; or a combination thereof.

Moreover, the words "example" or "exemplary" are used in this disclosure to mean serving as an example, instance, or illustration. Any aspect or design described in this disclosure as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Computing devices typically include a variety of media, which can include computer-readable storage media and/or communications media, in which these two terms are used in this description differently from one another as follows. Computer-readable storage media can be any available storage media that can be accessed by the computer, is typically of a non-transitory nature, and can include both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium.

On the other hand, communications media typically embody computer-readable instructions, data structures, program modules or other structured or unstructured data in a data signal that can be transitory such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

In view of the exemplary systems described above, methodologies that may be implemented in accordance with the described subject matter will be better appreciated with reference to the flowcharts of the various figures. For simplicity of explanation, the methodologies are depicted and described as a series of acts. However, acts in accordance with this disclosure can occur in various orders and/or concurrently, and with other acts not presented and described in this disclosure. Furthermore, not all illustrated acts may be required to implement the methodologies in accordance with certain aspects of this disclosure. In addition, those skilled in the art will understand and appreciate that the methodologies could alternatively be represented as a series of interrelated states via a state diagram or events. Additionally, it should be appreciated that the methodologies disclosed in this disclosure are capable of being stored on an article of manufacture to facilitate transporting and transferring such methodologies to computing devices. The term article of manufacture, as used in this disclosure, is intended to encompass a computer program accessible from a computer-readable device or storage media.

What is claimed is:

1. A system, comprising:
   a memory that stores computer executable components;
   a processor that executes computer executable components stored in the memory, wherein the computer executable components comprise:
   a receiving component that receives arrival data regarding an entity arriving at a healthcare facility;
   a discovery component that determines intent information regarding an intent of the entity at the healthcare facility, and analyzes the intent information to determine a destination location for the entity within the healthcare facility;
   a wayfinding component that facilitates navigating the entity to the destination location by providing the entity, via a mobile device associated with the entity, with real-time navigation information to the destination location; and
   an assistance component that determines whether a mental or physical condition of the entity indicates a need for physical assistance in association with the navigating and schedules appropriate medical personal or equipment to a current location of the entity accordingly.

2. The system of claim 1, wherein the wayfinding component determines position, orientation and elevation information in association with providing the entity with the real-time navigation information.

3. The system of claim 2, wherein the wayfinding component determines the elevation information based on electromagnetic information associated with a ground upon which one or more buildings of the healthcare facility are established.

4. The system of claim 1, wherein the wayfinding component determines a route for the entity from a current location of the entity at a time off arrival of the entity at the healthcare facility to the destination location based on one or more preferences of the entity and one or more points of interest within the healthcare facility.

5. The system of claim 1, wherein the wayfinding component determines a route for the entity from a current location of the entity at a time off arrival of the entity at the healthcare facility to the destination location based a physical limitation of the entity.

6. The system of claim 1, wherein the computer executable components further comprise:
an appointment component that interfaces with an appointment scheduling system associated with the healthcare facility and determines appointment information regarding one or more medical appointments scheduled for the entity at the healthcare facility based on the arrival data, and wherein the discovery component determines the intent information based on the appointment information.

7. The system of claim 1, wherein the entity comprises a patient, wherein the intent of the entity at the healthcare facility comprises attending a medical appointment, and wherein the destination location comprises an appointment location at the healthcare facility where the medical appointment is scheduled.

8. The system of claim 7, wherein the computer executable components further comprise:
a waiting time management component that determines an estimated time at which the medical appointment will commence based on a current schedule of a clinician with whom the appointment is scheduled, and wherein the wayfinding component determines a route for the entity from a current location of the entity to the destination location based on the estimated time at which the medical appointment will commence, one or more preferences of the entity, and one or more points of interest within the healthcare facility.

9. The system of claim 7, wherein the computer executable components further comprise:
an appointment preparation component that facilitates generating, prior to initiation of the medical appointment, one or more questions the entity has regarding the medical appointment for providing to a clinician involved with performing the medical appointment.

10. The system of claim 7, wherein the computer executable components further comprise:
a check-in component that facilities checking the patient into the medical appointment via the mobile device in response to a determination that the patient has arrived at the appointment location.

11. The system of claim 7, wherein the computer executable components further comprise:
a waiting time management component that determines and provides the patient, via the mobile device, with real-time updates regarding an estimated duration of a waiting time period before the medical appointment will begin.

12. The system of claim 11, wherein the waiting time management component further provides the patient, via the mobile device, with relevant informative information associated with the medical appointment for viewing during the waiting time period.

13. The system of claim 12, wherein the waiting time management component determines the relevant informative information based on the estimated duration of the waiting time period.

14. The system of claim 12, wherein the waiting time management component determines the relevant informative information based on one or more of: a purpose of the appointment, a preference of the patient, or a current mental state of the patient.

15. The system of claim 11, wherein the waiting time management component further suggests, via the mobile device, one or more points of interest within the healthcare facility for visiting by the patient during the waiting time period based in part on the estimated duration of the waiting time period.

16. A method, comprising:
receiving, by a system comprising a processor, arrival data regarding an entity arriving at a healthcare facility;
determining, by the system based on the arrival data, intent information regarding an intent of the entity at the healthcare facility;
analyzing, by the system, the intent information to determine a destination location for the entity within the healthcare facility;
facilitating, by the system, navigating the entity to the destination location by providing the entity, via a mobile device associated with the entity, with real-time navigation information to the destination location;
determining, by the system, whether a mental or physical condition of the entity indicates a need for physical assistance in association with the navigating; and
providing, by the system, appropriate medical personal or equipment to a current location of the entity based on a determination that the mental of physical condition of the entity indicates the physical assistance is needed.

17. The method of claim 16, wherein the facilitating comprises determining position information for the entity, including determining elevation information regarding a current elevation of the entity based on electromagnetic information associated with a ground upon which one or more buildings of the healthcare facility are established.

18. The method of claim 16, wherein the facilitating comprises determining a route for the entity from a current location of the entity at a time off arrival of the entity at the healthcare facility to the destination location based on one or more preferences of the entity and one or more points of interest within the healthcare facility.

19. The method of claim 16, further comprising:
interfacing, by the system, with an appointment scheduling system associated with the healthcare facility; and
determining, by the system, appointment information regarding one or more medical appointments scheduled for the entity at the healthcare facility based on the arrival data, and wherein determining the intent information comprises determining the intent information based on the appointment information.

20. The method of claim 16, wherein the entity comprises a patient, wherein the intent of the entity at the healthcare facility comprises attending a medical appointment, and wherein the destination location comprises an appointment location at the healthcare facility where the medical appointment is scheduled.

21. The method of claim 20, further comprising:
determining, by the system, an estimated time at which the medical appointment will commence based on a current schedule of a clinician with whom the appointment is scheduled; and determining, by the system, a route for the entity from a current location of the entity to the destination location based on the estimated time at which the medical appointment will commence, one or more preferences of the entity, and one or more points of interest within the healthcare facility.

22. The method of claim 16, wherein the entity comprises a patient, wherein the intent of the entity at the healthcare facility comprises attending a medical appointment, and wherein the destination location comprises an appointment location at the healthcare facility where the medical appointment is scheduled, wherein the method further comprises:
- determining, by the system, an estimated duration of a waiting time period before the medical appointment will begin;
- determining, by the system, relevant informative information associated with the medical appointment for viewing during the waiting time period based on the estimated duration of the waiting time period; and
- providing, by the system, the relevant information to the patient via the mobile device.

23. A non-transitory machine-readable storage medium, comprising executable instructions that, when executed by a processor of a device, facilitate performance of operations, comprising:
- receiving arrival data regarding a patient arriving at a healthcare facility;
- determining, based on the arrival data, intent information regarding an intent of the patient at the healthcare facility;
- analyzing the intent information to determine a destination location for the patient within the healthcare facility;
- facilitating navigating the patient to the destination location by providing the patient, via a mobile device associated with the patient, with real-time navigation information to the destination location;
- determining, by the system, whether a mental or physical condition of the patient indicates a need for physical assistance in association with the navigating; and
- providing, by the system, appropriate medical personal or equipment to a current location of the patient based on a determination that the mental of physical condition of the patient indicates the physical assistance is needed.

24. The non-transitory machine-readable storage medium of claim 23, wherein the determining the intent information comprises determining the patient has an upcoming appointment scheduled at the healthcare facility, and wherein the analyzing comprises determining the destination location is an appointment location where the appointment is scheduled based on the current time and a time at which the appointment is scheduled.

25. The non-transitory machine-readable storage medium of claim 23, wherein intent of the patient comprises attending a medical appointment, and wherein the destination location comprises an appointment location at the healthcare facility where the medical appointment is scheduled, and wherein the operations further comprises:
- determining an estimated duration of a waiting time period before the medical appointment will begin;
- determining relevant informative information associated with the medical appointment for viewing during the waiting time period based on the estimated duration of the waiting time period; and
- providing the relevant information to the patient via the mobile device.

* * * * *